United States Patent [19]

Niman

[11] Patent Number: 5,733,738
[45] Date of Patent: Mar. 31, 1998

[54] POLYPEPTIDE-INDUCED MONOCLONAL RECEPTORS TO PROTEIN LIGANDS

[75] Inventor: Henry L. Niman, Carlsbad, Calif.

[73] Assignee: Ligand Pharmaceuticals, San Diego, Calif.

[21] Appl. No.: 418,898

[22] Filed: Apr. 7, 1995

Related U.S. Application Data

[63] Continuation of Ser. No. 925,815, Aug. 4, 1992, abandoned, which is a continuation of Ser. No. 779,143, Oct. 21, 1991, abandoned, which is a continuation of Ser. No. 393,267, Aug. 12, 1989, abandoned, which is a continuation-in-part of Ser. No. 232,395, Aug. 12, 1988, abandoned, which is a continuation-in-part of Ser. No. 118,823, Nov. 9, 1987, abandoned, which is a continuation-in-part of Ser. No. 39,534, Apr. 16, 1987, Pat. No. 5,015,571, which is a continuation-in-part of Ser. No. 736,545, May 21, 1985, abandoned, which is a continuation-in-part of Ser. No. 701,954, Feb. 15, 1985, Pat. No. 5,030,565, which is a continuation-in-part of PCT/US84/01304 Aug. 17, 1984, abandoned, which is a continuation-in-part of Ser. No. 524,804, Aug. 17, 1983, abandoned.

[51] Int. Cl.$^6$ .................................................. G01N 33/574
[52] U.S. Cl. ........................ 435/7.23; 436/503; 436/548; 436/813
[58] Field of Search .......................... 424/138.1, 155.1, 424/174.1; 435/7.23, 240.27; 436/503, 548, 64, 813; 530/324, 325, 326, 327, 328, 329, 387.7, 388.8, 389.7, 808, 828

[56] References Cited

U.S. PATENT DOCUMENTS

| 4,452,901 | 6/1984 | Gordon et al. ................................. 435/7 |
| 4,532,220 | 7/1985 | Lavi ........................................ 436/813 X |
| 4,535,058 | 8/1985 | Weinberg ................................. 436/813 X |
| 4,786,718 | 11/1988 | Weinberg et al. ..................... 436/813 X |
| 5,030,563 | 7/1991 | Niman et al. ............................. 435/70.21 |
| 5,081,230 | 1/1992 | Carney ........................................... 530/387 |

FOREIGN PATENT DOCUMENTS

| 0108564 | 10/1983 | European Pat. Off. ............. G01N 33/54 |
| 0177814 | 9/1985 | European Pat. Off. ............. A61K 39/395 |
| 0203587 | 5/1986 | European Pat. Off. ............. C07K 7/08 |
| 0318179 | 11/1988 | European Pat. Off. ............. G01N 33/574 |
| 8403087 | 2/1984 | WIPO ................................. C07C 103/52 |

OTHER PUBLICATIONS

"Oncogenes and oncagene proteins", Brandt–Ravt et al. Occupational Medicine: State of the Art Reviews 2(1) pp. 27–38 (1987).
"Activation of H ras Oncogene in Rat Bladder Tumors induced by N-Betyl-N-(4 Hydroxybutyl) Nitrosamine" Fujita et al., J. Natl. Cancer Inst. 80(1): 37–43, 1988.
Brandt–Rauf, et al. "Serum Oncogene Proteins in Foundry Workers," J. Soc. Occup. Med. (1980), vol. 40, pp. 11–14.
Brandt–Rauf, et al. "Serum Oncoproteins and Growth Factors in Asbestosis and Silicosis Patients," Int. J. Cancer, (1992) vol. 50, pp. 881–885.
Forth et al. Monoclonal Antibodies to the p 21 Products of the Transforming Gene of Harvey Murine Sarcoma Virus and of the Cellular rasGene Family. J. Vrol. 43:294–304.
Brandt–Rauf, P., Occupational Medicine: State of the Reviews 5:59–65 (1990).
Brandt–Rauf, P. and Niman, H.L., British J. Indus. Med. 45(10): 689–693 (Oct. 1988).
Brandt–Rauf, P., J. Occup. Med. 30: 399–404 (May 1988).
Brandt–Rauf, P., et al., J. Soc. Occup. Med. 39: 141–143 (1989).
Green, et al., Cell 28: 477–487 (Mar. 1982).
Sutcliffe, et al., Science 219: 660–666 (Feb. 1983).
Wilson, et al., Cell 37: 767–778 (1984).
Bizub, et al.Oncogene 1: 131–142 (1987.
Niman, et al.PNAS–USA 82: 7924–7928 (Dec. 1985).

*Primary Examiner*—David Saunders
*Attorney, Agent, or Firm*—Lyon & Lyon LLP

[57] ABSTRACT

The present invention relates to immunological receptors and ligands, and more particularly to monoclonal receptors raised to peptides whose amino acid residue sequences correspond to sequences of retroviral ligands. The receptors are used to assay body samples from a host to indicate exposure of the host to a carcinogen.

6 Claims, 48 Drawing Sheets

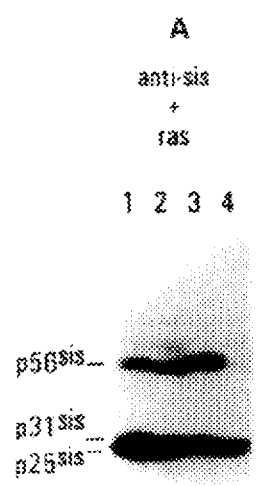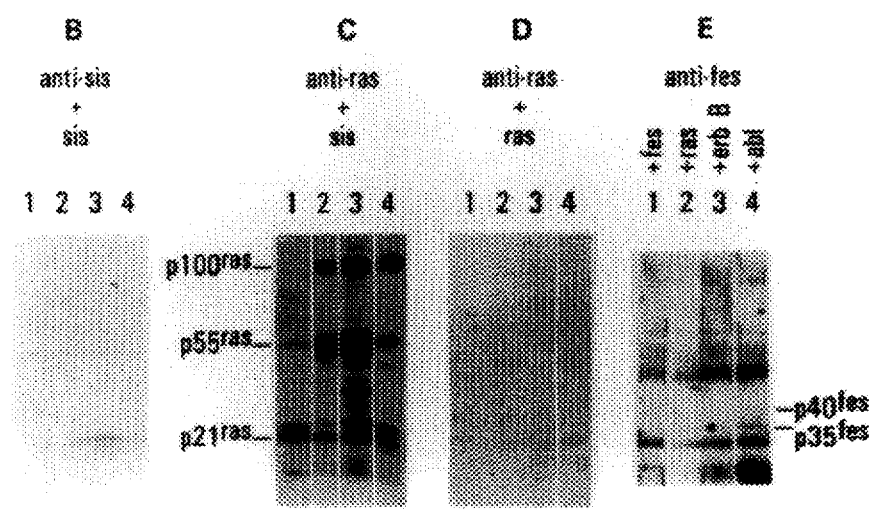
FIG. 15a. FIG. 15b. FIG. 15c. FIG. 15d. FIG. 15e.

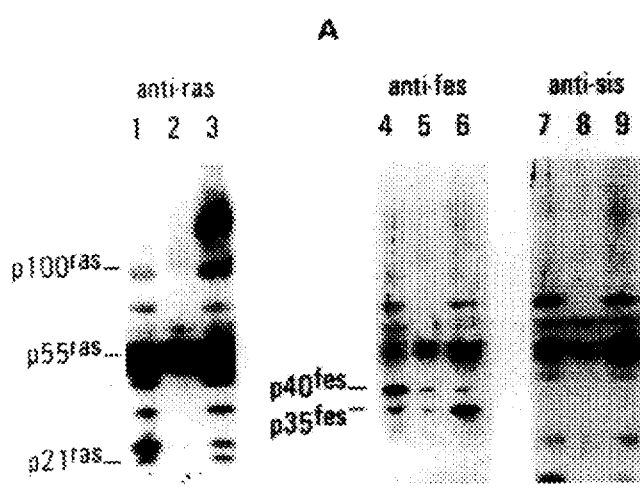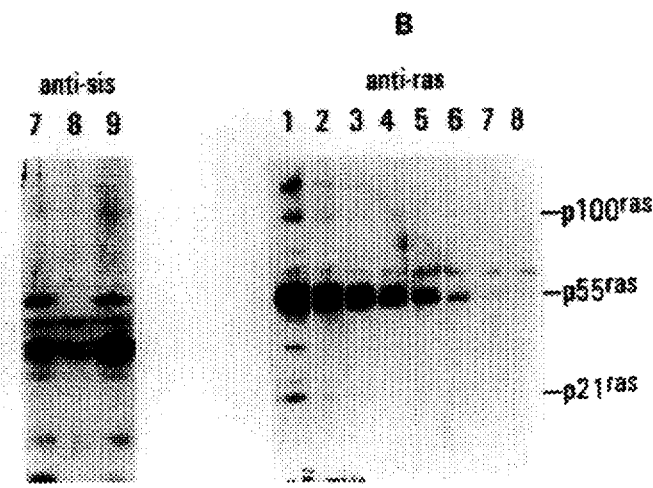

FIG. 17a.  A   anti-ras
1 2 3 4 5 6 7 8 p55$^{ras}$—
p21$^{ras}$—

FIG. 17b.  B   anti-fes
1 2 3 4 5 6 7 8 p40$^{fes}$—
p35$^{fes}$—

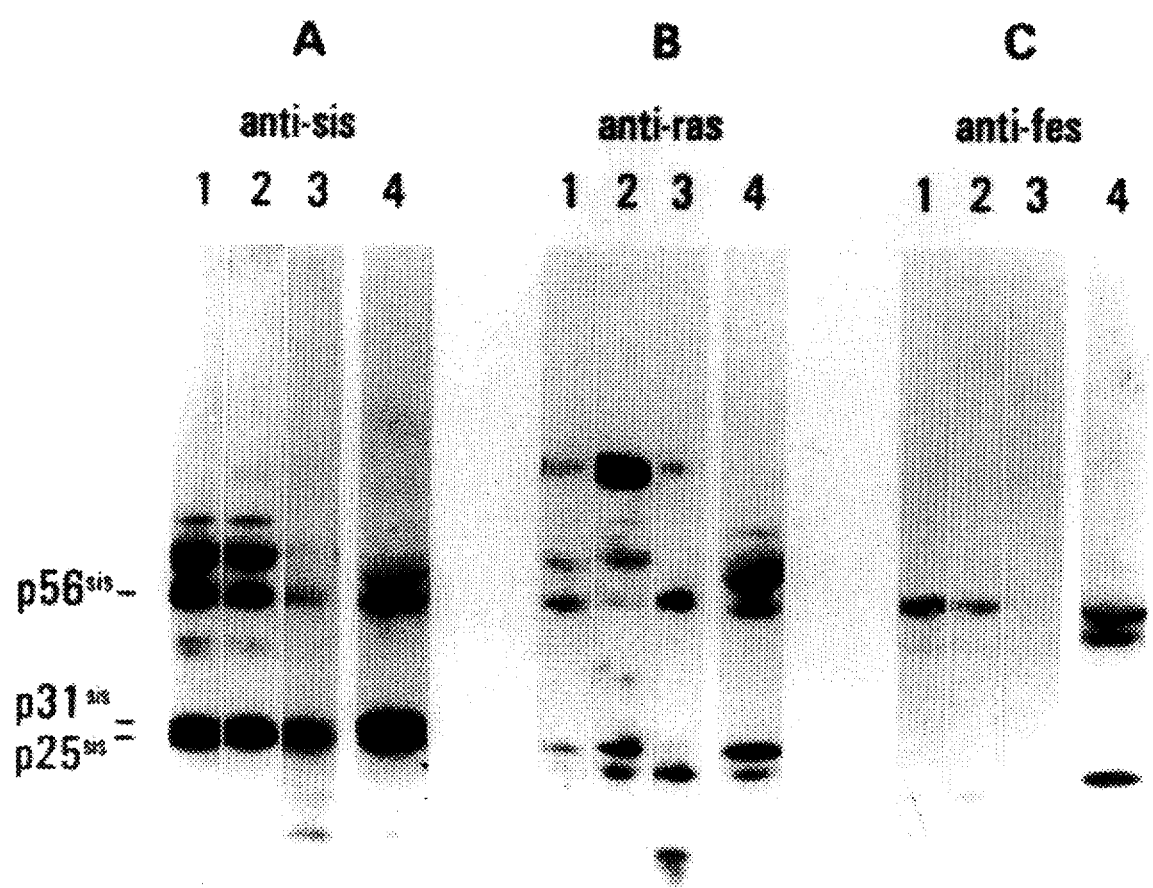

CONSERVED KINASE REGION 1

| Oncogene | Residue Positions | Polypeptide Sequence |
|---|---|---|
| fes$^{ST}$ | 519-530 | IGRGNFGEVFSG |
| fes$^{GA}$ | 702-713 | IGRGNFGEVFSG |
| fps | 927-938 | IGRGNFGEVFSG |
| src | 273-284 | LGQGCFGEVWMG |
| yes | 557-568 | LGQGCFGEVWMG |
| fgr | 310-321 | LGQGCFGEVWLG |
| fms | 618-629 | LGTGAFGKVYEA |
| erb B | 138-149 | LGTGAFGTIYKG |
| mht | 91-102 | IGSGSFGTVYGK |
| raf | 30-41 | IGSGSFGTVYGK |
| abl | 368-379 | LGGGQYGEVYEG |
| mos | 100-111 | LGSGGFGSVYKA |

FIG. 20.

CONSERVED KINASE REGION 2

| Oncogene | Residue Positions | Polypeptide Sequence |
|---|---|---|
| fes$^{ST}$ | 674-688 | VPVKWTAPEALNYGR |
| fes$^{GA}$ | 857-871 | VPVKWTAPEALNYGR |
| fps | 1082-1096 | IPVKWTAPEALNYGW |
| src | 424-438 | FPIKWTAPEAALYGR |
| yes | 708-722 | FPIKWTAPEAALYGR |
| fgr | 461-475 | FPIKWTAPEAALYGR |
| fms | 847-862 | LPVKWMAPESIFOCV |
| erb B | 296-310 | VPIKWMALESILHRI |
| mht | 238-253 | GSVLWMAPEVIRMQD |
| raf | 177-192 | GSVLWMAPEVIRMQD |
| abl | 521-535 | FPIKWRAPESLAYNK |
| mos | 269-284 | GTYTHQAPEILKGEI |

FIG. 21.

CONSERVED KINASE REGION 3

| Oncogene | Residue Positions | Polypeptide Sequence |
|---|---|---|
| fes$^{ST}$ | 744-759 | LMEQCWAYEPGQRPSF |
| fes$^{GA}$ | 927-942 | LMEQCWAYEPGQRPSF |
| fps | 1152-1167 | LMQRCWEYDPHRRPSF |
| src | 494-509 | LMCQCWRKDPEERPTF |
| yes | 770-793 | LMKLCWKKDPDERPTF |
| fgr | 531-546 | AMEQTWRLDPEERPTF |
| fms | 910-933 | FMQACWALEPTRRPTF |
| erb B | 366-381 | IMVKCWMIDADSRPKF |
| mht | 316-331 | LVADCLKKVREERPLE |
| raf | 255-270 | LVADCVKKVKEERPTF |
| abl | 591-606 | LMRACWQWNPSDRPSF |
| mos | 344-359 | IIQSCWEARGLQRPTF |
| rel | 382-397 | TLHSCWQQLYSPSPSA |

FIG. 22.

DETECTION OF ONCOGENE-RELATED PROTEINS IN URINE FROM CANCER PATIENTS AND NORMAL INDIVIDUALS

FREQUENCY[1]

| DIAGNOSIS | NO. | p100$^{ras}$ | p55$^{ras}$ | p23$^{ras}$ | p56$^{sis}$ | p31$^{sis}$ | p25$^{sis}$ | p40$^{fes}$ | p35$^{fes}$ |
|---|---|---|---|---|---|---|---|---|---|
| BREAST | 58 | 9 14 16 | 12 1 16 | 5 22 29 | 0 5 9 | 7 7 29 | 10 17 40 | 7 5 3 | 10 10 10 |
| BLADDER | 21 | 10 5 19 | 5 0 5 | 5 29 43 | 5 29 14 | 10 14 19 | 5 29 29 | 0 0 5 | 0 0 14 |
| PROSTRATE | 16 | 13 19 31 | 0 0 0 | 6 6 63 | 6 25 19 | 19 6 25 | 12 25 25 | 0 0 0 | 0 0 12 |
| LUNG | 14 | 0 0 36 | 0 7 0 | 0 7 64 | 0 14 7 | 14 7 50 | 14 50 14 | 0 0 0 | 0 14 0 |
| LYMPHOMA | 14 | 21 7 14 | 0 7 0 | 0 36 43 | 0 0 29 | 14 21 14 | 7 36 36 | 0 0 0 | 0 0 0 |
| CERVIX | 11 | 9 27 9 | 9 9 18 | 9 27 36 | 0 9 9 | 16 18 9 | 27 18 18 | 0 0 9 | 0 0 18 |
| OTHER[2] | 55 | 9 15 22 | 2 4 9 | 24 26 26 | 2 11 20 | 9 22 24 | 13 31 26 | 0 0 0 | 2 4 0 |
| TOTAL | 189 | 10 13 20 | 5 3 9 | 9 23 37 | 2 12 14 | 11 14 25 | 12 28 29 | 3 2 2 | 3 4 7 |
| NORMAL | 51 | 10 16 20 | 2 6 12 | 2 27 33 | 2 6 10 | 2 10 14 | 6 14 24 | 2 2 4 | 0 6 6 |

[1] THREE NUMBERS ARE LISTED UNDER EACH ONCOGENE-RELATED PROTEIN. THE FIRST NUMBER REPRESENTS THE PERCENTAGE OF SAMPLES THAT CONTAINED 15 FOLD ELEVATIONS OVER DETECTABLE LEVELS. THE SECOND NUMBER REPRESENTS THE PERCENTAGE WITH 5-15 FOLD ELEVATIONS WHILE THE THIRD NUMBER REPRESENTS PERCENTAGE CONTAINING DETECTABLE LEVELS.

[2] URINE (AND NUMBER TESTED) ORIGINATED FROM DONORS WITH THE FOLLOWING NEOPLASTIC DIAGNOSIS: BASAL (2), LEUKEMIA (10), COLON (4), GASTRIC (5), HODGKINS (7), KIDNEY (4), MELANOMA (9), MOLAR PREGNANCY (2), MYELOMA (6), OVARIAN (3), TESTICULAR (3).

FIG. 23.

DETECTION OF ONCOGENE-RELATED PROTEINS IN URINE FROM PREGNANT WOMEN

FREQUENCY[1]

| WEEKS | NO. | p100^ros | p55^ros | p25^ros | p56^sis | p31^sis | p25^sis | p40^fes | p35^fes |
|---|---|---|---|---|---|---|---|---|---|
| 4-13 | 31 | 10 13 23 | 10 6 13 | 10 26 33 | 3 3 35 | 3 6 23 | 0 23 29 | 6 6 10 | 6 10 9 |
| 4-27 | 60 | 10 10 17 | 13 2 8 | 10 22 32 | 15 10 27 | 10 18 35 | 10 35 23 | 2 0 10 | 5 8 5 |
| 28-40 | 169 | 6 9 15 | 11 8 11 | 14 36 30 | 13 25 21 | 14 20 33 | 18 29 37 | 4 7 7 | 11 13 8 |
| TOTAL | 260 | 7 10 15 | 10 6 10 | 13 35 31 | 12 19 24 | 12 19 24 | 14 30 33 | 4 5 8 | 9 12 8 |
| TUMOR | 189 | 10 13 20 | 5 3 9 | 9 23 37 | 2 12 14 | 11 14 25 | 12 28 29 | 3 2 2 | 3 4 7 |
| NORMAL | 51 | 10 16 20 | 2 6 12 | 2 27 33 | 2 6 10 | 2 10 14 | 6 14 24 | 2 2 4 | 0 6 6 |

[1] THREE NUMBERS ARE LISTED UNDER EACH ONCOGENE-RELATED PROTEIN. THE FIRST NUMBER REPRESENTS THE PERCENTAGE OF SAMPLES THAT CONTAINED >15-FOLD ELEVATIONS OVER DETECTABLE LEVELS. THE SECOND NUMBER REPRESENTS THE PERCENTAGE WITH 5-15-FOLD ELEVATIONS, WHILE THE THIRD NUMBER REPRESENTS PERCENTAGE CONTAINING DETECTABLE LEVELS.

FIG. 24.

FIG. 41a.
TABLE 14

| PRIMARY | SEC. | DEG. | NO. | βTGF 100 30C5 (a) | (b) | sis 114 50D4 | | | | | fes 127 50D12 | | H-ras 146 3E4 | | | | src 202 9D10 | | int-1 222 2B2 | | | ros 360 27E6 | | ros 361 31C5 | | | erb A 462 11E4 |
|---|---|---|---|---|---|---|---|---|---|---|---|---|---|---|---|---|---|---|---|---|---|---|---|---|---|---|---|
| | | | | 45 | 29 25 | 55 | 48 | 22 | 18 | 16 | 45 | 200 | 52 | 48 | 27 | 21 | 60 | 48 | 27 | 15 | 13 | 125 | 15 | 150 | 120 | 40 | 22 |
| BREAST | ADE | MIN | 021-20093-1 | 0 | 5 | 0 | 0 | 0 | 3 | 0 | | 0 | 2 | 3 | 0 | 2 | 0 | 0 | 0 | 0 | 0 | 2 | 2 | 2 | 2 | 2 | 0 |
| | ADE | MOD | 021-20093-2 | 1 | 2 5 | 0 | 0 | 0 | 2 | 0 | | 0 | 0 | 2 | 2 | 2 | 0 | 0 | 0 | 0 | 0 | 2 | 2 | 2 | 2 | 0 | 0 |
| | ADE | MOD | 021-20631X2 | 0 | 0 3 | 0 | 0 | 1 | 1 | 3 | 1 | 1 | 0 | 2 | 0 | 0 | 0 | 0 | 0 | 0 | 2 | 0 | 1 | 0 | 0 | 0 | 3 |
| | | MIN | 031-12319-1 | 0 | 0 5 | 0 | 0 | 1 | 0 | 2 | 1 | 0 | 1 | 2 | 0 | 2 | 0 | 0 | 0 | 0 | 0 | 2 | 2 | 0 | 0 | 0 | 0 |
| | | MOD | 021-12347-1 | 2 | 1 3 | 0 | 0 | 0 | 0 | 2 | 0 | 3 | 3 | 3 | 2 | 3 | 0 | 0 | 0 | 0 | 0 | 0 | 0 | 2 | 0 | 0 | 3 |
| | | MOD | 031-12366-1 | 0 | 2 5 | 0 | 0 | 0 | 0 | 0 | 0 | 0 | 0 | 2 | 0 | 1 | 0 | 0 | 0 | 0 | 0 | 2 | 3 | 0 | 0 | 3 | 0 |
| | | MOD | 031-12797-1 | 0 | 0 3 | 1 | 0 | 2 | 2 | 3 | 0 | 2 | 0 | 2 | 0 | 3 | 0 | 0 | 0 | 0 | 0 | 2 | 2 | 0 | 0 | 0 | 2 |
| | | MOD | 031-14459-1 | 0 | 0 4 | 0 | 0 | 0 | 0 | 0 | 1 | 0 | 0 | 2 | 0 | 1 | 0 | 0 | 0 | 0 | 0 | 0 | 3 | 0 | 0 | 0 | 0 |
| | | ADV | 021-504 | 0 | 0 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | | ADV | 021-512 | 0 | 0 1 | 0 | 1 | 0 | 1 | 0 | 0 | 0 | 0 | 0 | 0 | 0 | 0 | 0 | 0 | 0 | 0 | 0 | 0 | 0 | 0 | 0 | 0 |
| | | ADV | 021-516 | 0 | 0 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | | ADV | 021-517 | 0 | 0 4 | 0 | 0 | 2 | 0 | 2 | 0 | 3 | 4 | 4 | 3 | 3 | 0 | 0 | 0 | 0 | 0 | 2 | 4 | 3 | 0 | 0 | 0 |
| | LN | ADV | 121-960-1 | 2 | 0 3 | 0 | 0 | 2 | 1 | 2 | 1 | 3 | 0 | 0 | 0 | 3 | 0 | 0 | 0 | 0 | 0 | 0 | 2 | 0 | 3 | 2 | 0 |
| OVARY | OM | MIN | 031-12877-1 | 2 | 1 5 | 0 | 0 | 0 | 2 | 2 | 0 | 0 | 3 | 3 | 2 | 2 | 0 | 0 | 0 | 2 | 2 | 2 | 3 | 0 | 0 | 3 | 1 |
| | OM | MOD | 031-15507 | 0 | 0 2 | 0 | 2 | 0 | 0 | 2 | 0 | 0 | 2 | 4 | 0 | 2 | 2 | 0 | 3 | 0 | 2 | 2 | 3 | 3 | 0 | 1 | 0 |
| | OM | MOD | 031-18265-1 | 2 | 0 4 | 2 | 0 | 2 | 0 | 2 | 2 | 3 | 3 | 5 | 2 | 2 | 0 | 0 | 0 | 0 | 3 | 3 | 4 | 3 | 0 | 4 | 0 |
| | OM | MOD | 031-10128-1 | 1 | 0 0 | 2 | 0 | 0 | 0 | 0 | 0 | 0 | 5 | 3 | 2 | 2 | 0 | 0 | 3 | 3 | 2 | 2 | 3 | 2 | 0 | 2 | 0 |
| | OM | ADV | 031-17431 | 0 | 0 4 | 0 | 0 | 0 | 0 | 3 | 0 | 0 | 2 | 3 | 1 | 1 | 2 | 2 | 3 | 0 | 1 | 1 | 2 | 2 | 0 | 1 | 0 |
| | OM | ADV | 031-18332 | 0 | 0 3 | 0 | 0 | 2 | 0 | 1 | 0 | 0 | 3 | 3 | 3 | 1 | 0 | 2 | 0 | 0 | 0 | 0 | 0 | 3 | 0 | 0 | 0 |
| | OM | ADV | 031-13530 | 0 | 0 4 | 0 | 0 | 0 | 0 | 2 | 0 | 0 | 2 | 3 | 2 | 2 | 2 | 0 | 0 | 0 | 2 | 2 | 3 | 3 | 0 | 0 | 0 |
| | OM | ADV | 031-13867 | 0 | 0 3 | 0 | 1 | 2 | 0 | 0 | 2 | 0 | 2 | 3 | 1 | 2 | 0 | 0 | 0 | 0 | 3 | 2 | 3 | 3 | 0 | 2 | 0 |
| | OM | ADV | 031-12757-1 | 1 | 1 5 | 1 | 0 | 0 | 0 | 0 | 1 | 0 | 1 | 3 | 2 | 1 | 2 | 0 | 0 | 0 | 3 | 2 | 2 | 2 | 0 | 0 | 1 |
| | OM | ADV | 031-15189 | 0 | 0 0 | 0 | 0 | 2 | 0 | 2 | 1 | 0 | 1 | 3 | 1 | 0 | 0 | 0 | 0 | 0 | 0 | 0 | 1 | 0 | 0 | 0 | 0 |
| | OM | ADV | 031-10214-1 | 0 | 0 3 | 0 | 0 | 0 | 0 | 0 | 1 | 0 | 1 | 3 | 0 | 0 | 2 | 0 | 0 | 0 | 2 | 2 | 2 | 2 | 0 | 0 | 0 |
| | IL | ADV | 031-19194 | 0 | 0 2 | 0 | 0 | 0 | 2 | 0 | 0 | 0 | 1 | 3 | 0 | 2 | 0 | 0 | 0 | 0 | 0 | 0 | 1 | 0 | 0 | 0 | 0 |
| | IA | ADV | 031-18550 | 0 | 0 2 | 0 | 0 | 2 | 2 | 2 | 1 | 0 | 1 | 3 | 0 | 1 | 2 | 0 | 0 | 0 | 2 | 2 | 2 | 0 | 1 | 0 | 0 |
| | RET | ADV | 031-18639 | 0 | 0 2 | 0 | 0 | 0 | 0 | 0 | 2 | 0 | 2 | 3 | 2 | 2 | 2 | 0 | 0 | 0 | 1 | 2 | 2 | 0 | 0 | 1 | 0 |

FIG. 41b.

(a) APPROXIMATE MOLECULAR WEIGHT OF ONCOGENE-RELATED PROTEIN (k DALTONS)
(b) 2ⁿ OVER DETECTABLE LEVELS

FIG. 42a.

TABLE 15

| BREAST | SEC. | DEG. | NO. | FES 121 363 (a) 60 | FES 121 363 40 | FES 121 9610 60 | FES 121 9610 18 | FES 121 9610 15 (b) | FES 121 15B10 70 | FES 121 15B10 35 | FES 121 15B10 30 | FES 121 19B10 30 | FES 121 19B10 100 | FES 125 10F03 48 | FES 125 10F03 35 | MOS 165 34E4 20 | MOS 165 34E4 18 | ERB B 171 11B9 55 | ERB B 171 11B9 50 | ERB B 171 19B10 18 | ERB B 171 19B10 130 | ERB B 173 4C11 40 | ERB B 173 4C11 35 |
|---|---|---|---|---|---|---|---|---|---|---|---|---|---|---|---|---|---|---|---|---|---|---|---|
| BREAST | ADE | MIN | 02I-20093-1 | 0 | 0 | 0 | 0 | 3 | 0 | 0 | 0 | 0 | 0 | 0 | 0 | 2 | 0 | 0 | 0 | 0 | 0 | 0 | 0 |
| | ADE | MOD | 02I-20093-3 | 0 | 0 | 0 | 0 | 3 | 0 | 0 | 0 | 0 | 0 | 0 | 0 | 2 | — | 0 | 0 | 0 | 0 | 0 | 0 |
| | ADE | MOD | 02I-20099-1 | 0 | 0 | 0 | 0 | 4 | — | 0 | — | 0 | 0 | 0 | 0 | 2 | — | 0 | 0 | 0 | 0 | 0 | 0 |
| | ADE | MOD | 02I-2063IX2 | — | 0 | 0 | — | 5 | 2 | 0 | — | 0 | 0 | 0 | 0 | 2 | — | 0 | 0 | 0 | 0 | 0 | 0 |
| | ADV | MIN | 03I-12391-1 | 0 | 0 | 0 | — | 3 | 0 | 0 | 0 | 0 | 0 | 0 | 0 | — | — | 0 | 0 | 0 | 0 | 0 | 0 |
| | ADV | MOD | 03I-12347-1 | 0 | 0 | 0 | — | 5 | — | 0 | 0 | 0 | — | 0 | — | 0 | — | — | 0 | — | 0 | 0 | 0 |
| | ADV | MOD | 03I-11748-1 | 0 | 0 | 0 | — | 4 | — | 0 | 0 | 0 | 0 | 0 | 0 | 0 | 0 | 0 | 0 | — | 0 | 2 | 0 |
| | ADV | MOD | 03I-14459 | 0 | 0 | 5 | 2 | 2 | 0 | 0 | 0 | 0 | 0 | 0 | 0 | 0 | 0 | 0 | 0 | — | 0 | 0 | 0 |
| | ADV | ADV | 02I-504 | 0 | 0 | 0 | 0 | 2 | — | 0 | 0 | 0 | 0 | 0 | 0 | 0 | 0 | 0 | 0 | 0 | 0 | 2 | 0 |
| | ADV | ADV | 02I-512 | 2 | 0 | 0 | 0 | — | 0 | 0 | 0 | 0 | 0 | 0 | 0 | 0 | 0 | 0 | 0 | 0 | 0 | 0 | 0 |
| | ADV | ADV | 02I-516 | 0 | 0 | 0 | 0 | 0 | 0 | 0 | 0 | 0 | 0 | 0 | 0 | 0 | 0 | 0 | 0 | 0 | 0 | 0 | 0 |
| | ADV | ADV | 02I-517 | 0 | 0 | 0 | 0 | 0 | 0 | 0 | 0 | 0 | 0 | 0 | 0 | 0 | 0 | 0 | 0 | 2 | 0 | 2 | 0 |
| | ADV | ADV | 02I-947 | 0 | 0 | 0 | 0 | 3 | 0 | 0 | 0 | 0 | 0 | 0 | 0 | 0 | 0 | 0 | 0 | 0 | 0 | 0 | 0 |
| | ADV | ADV | 02I-20078 | — | 0 | 0 | 0 | 3 | 0 | 0 | 0 | 0 | 0 | 0 | 0 | 0 | 0 | 0 | 0 | 0 | 0 | 0 | 0 |
| | ADV | ADV | 02I-2832 | 0 | 0 | — | — | 4 | — | 0 | 0 | 0 | 0 | 0 | 0 | 2 | 0 | 0 | 0 | 0 | 0 | 0 | 0 |
| OVARY | CYST | MIN | 04I-7975-1 | 0 | 0 | 0 | — | 3 | 0 | 0 | 0 | 0 | 0 | 0 | 0 | 2 | 0 | 0 | 0 | 0 | 0 | 0 | 0 |
| | OM | MOD | 03I-15517 | 0 | — | — | — | 4 | 2 | — | 0 | 0 | — | — | 0 | — | 0 | — | 0 | 2 | — | 0 | 0 |
| | OM | MOD | 03I-18265 | 0 | 2 | 0 | 2 | 4 | 2 | 2 | 0 | 2 | — | — | 0 | — | 0 | 2 | 3 | 2 | 2 | 2 | 2 |
| | OM | ADV | 03I-12770-1 | — | 0 | 2 | — | 5 | 3 | 2 | — | 0 | 0 | 0 | 0 | 2 | — | — | 0 | 2 | 0 | 3 | — |
| | OM | ADV | 03I-17431 | 0 | 2 | 0 | 2 | 4 | 2 | — | — | 2 | 2 | 2 | 0 | 2 | — | — | 2 | 2 | 2 | 0 | 0 |
| | OM | ADV | 03I-18332 | — | 0 | 0 | — | 4 | 2 | 0 | 0 | 0 | 0 | 0 | 0 | — | 2 | 0 | 0 | 2 | 0 | — | — |
| | OM | ADV | 03I-13530 | — | 0 | 0 | 0 | 5 | 3 | 0 | 0 | 0 | 0 | 0 | 0 | 0 | 2 | 0 | 0 | 2 | 0 | 0 | 2 |
| | OM | ADV | 03I-13867 | 0 | 0 | 0 | — | 4 | 2 | 0 | 0 | 0 | 0 | 0 | 0 | — | 0 | 0 | 0 | 0 | 0 | 0 | 0 |
| | OM | ADV | 03I-15189 | — | 0 | 0 | 0 | 4 | 2 | 0 | 0 | 0 | 0 | 0 | 0 | 0 | 0 | 0 | 0 | 0 | 0 | 0 | 0 |
| | IL | ADV | 03I-19194 | 0 | — | 0 | — | 4 | 0 | 0 | 0 | 0 | 0 | 0 | 0 | 2 | 0 | — | 0 | 0 | 0 | 0 | 0 |
| | IA | ADV | 03I-18550 | — | 0 | — | — | 3 | 0 | 0 | 0 | — | 0 | 0 | 0 | — | 0 | 0 | 0 | 0 | 0 | 0 | 0 |
| | RET | ADV | 03I-18639 | 0 | 0 | 0 | 0 | 0 | 2 | 0 | — | 0 | 0 | — | 0 | — | 0 | — | 2 | — | 2 | 0 | 0 |

| | | | | | | | | | | | | | | | | | | | | | |
|---|---|---|---|---|---|---|---|---|---|---|---|---|---|---|---|---|---|---|---|---|---|
| ENDOME- ON MOD | 031-12328-1 | — | 0 | 0 | — | 4 | — | 3 | 0 | 0 | 0 | 0 | 2 | 0 | 0 | 0 | 0 | 0 | 0 | 0 | 0 |
| TRIUM CORP | 017-731473-1 | 2 | — | — | 0 | 5 | 3 | 2 | 0 | 0 | 0 | 0 | 2 | 0 | 0 | 0 | 0 | 0 | 0 | 0 | 0 |
| CORP | 031-15378 | 0 | 0 | 0 | 0 | 3 | 2 | 2 | 0 | 0 | 0 | 0 | 2 | 0 | 0 | 0 | 0 | 0 | 0 | 0 | 0 |
| PANCREAS LIV | 017-0047 | — | 0 | — | 0 | 4 | 0 | 0 | 0 | 0 | 0 | 0 | 2 | 0 | 0 | 0 | 3 | 0 | 0 | 0 | 0 |
| LIV | 071-791509 | 0 | 0 | — | 0 | 3 | 0 | 0 | 0 | 0 | 0 | 0 | — | 0 | 0 | 0 | 0 | 0 | 0 | — | — |
| LUNG LN | 041-78297-1 | 0 | 3 | 0 | 0 | 3 | 0 | 0 | 0 | 0 | 0 | — | 2 | 0 | — | 0 | — | 0 | 0 | 2 | 0 |
| RET | 041-78297-6 | 0 | 3 | 0 | 0 | 3 | 0 | 0 | 0 | 0 | 0 | 0 | — | 0 | 0 | 0 | — | 0 | 2 | 0 | 0 |
| RECTUM LN ADV | 017-7789-01 | — | 0 | 0 | 0 | 3 | 0 | — | 0 | 0 | 0 | 0 | 2 | 0 | 0 | 0 | 0 | 0 | 0 | 0 | 0 |
| STOMACH MOD | 031-13675 | 0 | 0 | 0 | 2 | 0 | 0 | — | 0 | 0 | 0 | 0 | — | 0 | 0 | 0 | 0 | — | 0 | 0 | 0 |
| HODGKINS SPL | 031-14719 | 0 | 0 | 0 | 0 | 0 | 0 | 0 | 0 | 0 | 0 | 0 | 0 | 0 | 0 | 0 | 0 | 0 | 0 | 0 | 0 |

(a) APPROXIMATE MOLECULAR WEIGHT OF ONCOGENE-RELATED PROTEIN (k DALTONS)

(b) $2^n$ OVER DETECTABLE LEVELS

FIG. 42b.

POLYPEPTIDE-INDUCED MONOCLONAL RECEPTORS TO PROTEIN LIGANDS

CROSS REFERENCE TO RELATED APPLICATION

This is a continuation of application Ser. No. 925,815, filed Aug. 4, 1992, abandoned, which is a continuation of application Ser. No. 779,143, filed Oct. 21, 1991, abandoned, which is a continuation of application Ser. No. 393,267, filed Aug. 12, 1989, abandoned, which is a continuation-in-part of application Ser. No. 232,395 filed on Aug. 12, 1988, abandoned, which is a continuation-in-part of application Ser. No. 118,823 filed on Nov. 9, 1987, abandoned which is a continuation-in-part of Ser. No. 039,534 filed on Apr. 16, 1987, U.S. Pat. No. 5,015,571, that is a continuation-in-part of application Ser. No. 736,545 filed on May 21, 1985, abandoned that is a continuation in part of application Ser. No. 701,954, filed Feb. 15, 1985, U.S. Pat. No. 5,030,565 that is a continuation in part of PCT application PCT/US84/01304 filed Aug. 17, 1984 wherein the U.S. National Phase was entered on Feb. 15, 1985 Ser. No. 713,410, abandoned that is a continuation-in-part application of U.S. application Ser. No. 524,084, filed Aug. 17, 1983, abandoned.

TECHNICAL FIELD

The present invention relates to immunological receptors and ligands, and more particularly to monoclonal receptors raised to polypeptides who whose amino acid residue sequences correspond to sequences of retroviral oncoprotein ligands.

BACKGROUND

Retroviruses are viruses that contain a single strand of RNA as the genetic material rather than DNA. The single-stranded RNA genome of each of these viruses gives rise to a double-stranded DNA molecule after the virus infects a susceptible host. This DNA replica of the viral genome then introduces itself permanently into a chromosome of the successfully infected cell and replicates in that host chromosome.

The retroviruses discussed hereinafter and in the claims may be further defined as being replication-defective retroviruses. Thus, these viruses do not themselves contain a gene encoding the reverse transcriptase usually required to permit the viral RNA genome to be translated into a DNA that can be introduced into a chromosome of the infected host. Rather, the retroviruses discussed hereinafter typically must be complimented in their infection by a so-called helper virus that is replication-competent. That second virus contains the gene that encodes the reverse transcriptase enzyme that incorporates the genomic materials from both viruses into the successfully infected host cells to transform those cells.

For ease in understanding, the replication-defective retroviruses will be discussed hereinafter and in the claims merely as retroviruses with the understanding that they are replication-defective and require the assistance of a helper virus for successful infection and transformation of host cells. This usage of the term retrovirus is known in the art and has been used in the art as such without further explanation.

Some members of the retrovirus family are highly oncogenic as judged by their ability to cause the formation of solid tumors within a short period of time after being inoculated into the host. These viruses can also cause "cancerous" changes in cells grown and cultured in the laboratory; such changes are called "transformations" and provide a reliable in vitro biological assay for oncogenic viruses. Several such viruses have been isolated from chickens, turkeys, mice, rats, cats and monkeys.

A single gene, the oncogene, located on the genome of these highly oncogenic viruses is responsible for the tumorigenic potential of the virus. In the case of several viruses, the protein products of their oncogenes, referred to herein as oncoproteins, have been immunologically identified by taking advantage of the fact that serum from an animal bearing a virus-induced tumor contains antibodies directed against those oncoproteins.

A rapidly growing body of evidence indicates that the oncogenes of retroviruses are closely related to and are derived from specific genetic loci in the normal cellular genetic information of all vertebrates.

Interest in oncogenes has steadily risen in the last decade. Although RNA tumor viruses have been implicated as the causative agents of experimentally induced neoplasia in chickens for over 50 years, it was not until the mid 1970s that mechanisms of virally induced neoplasia began to emerge [Bishop (1983) *Ann. Rev. Biochem.* 52:301–54]. According to one such mechanism, replication-competent arian viruses and defective mammalian viruses had captured cellular genes that provided the viruses with a transforming potential.

Molecular hybridization studies using specific nucleic acid probes, followed by genetic cloning of viral oncogenes and their cellular relatives by recombinant DNA technology, have established the kinship between retroviral oncogenes (v-onc) and cellular oncogenes (c-onc) found in all normal vertebrate cells. Molecular analysis of the several retroviruses thus far isolated has revealed more than two dozen different oncogenes. In most cases, a corresponding cellular to the retroviral oncogene or oncoprotein has been isolated.

For example, the human EJ or T24 bladder carcinoma oncogene was identified as the homolog of the transforming gene of Harvey murine sarcoma virus ($ras^{Ha}$) and also of the BALB sarcoma virus (bas) [Parada et al., *Nature*, 297, 474–478 (1982); Der et al., *Proc. Natl. Acad. Sci USA*, 79, 3627–3634 (1982); and Santos et al., *Nature*, 298, 343–347 (1982)]. In addition, the oncogene of the human carcinoma cell line LX-1 was found to be homologous to the transforming gene of Kirsten strain of murine sarcoma virus ($ras^{Ki}$) [Der et al., above]. Still further, the v-onc for a c-onc designated fps of avian origin is represented at least twice among a limited number of avian retrovirus isolates; its mammalian cognate designated fes in feline species is found in two different strains of feline sarcoma viruses.

The homology [Doolittle et al., (1983) *Science* 221:275–277; Waterfield et al., (1983) *Nature* 304:35–39] between the gene product of the sis oncogene and one of the chains of platelet-derived growth factor provided the most solid link between malignant transformation by oncogenes and stimulation of normal cell division by growth factors. This identity between oncogene products and growth factors and cellular receptors was further substantiated with sequence analysis of the epidermal growth factor cellular receptor [Downward et al., (1984) *Nature* 307, 521–527; Ullrich et al., (1984) *Nature* 309:418–425] that was found to be the normal homologue of erb B. Furthermore, immunological cross-reactivity of fms antibodies with colony stimulating factor-1 receptor [Sherr et al., (1985) *Cell:* 665–676] as well as protein kinase homology with the insulin receptor

[Ullrich et al., (1985) *Nature* 313, 756–761] and platelet derived growth factor receptor [Yarden et al., (1986) *Nature* 323; 226–232] indicated the kinase activity of many of the sequenced oncogenes would be important in the signal transduction of several growth factors.

Sequencing of oncogenes captured by retroviruses or identified via transfection experiments greatly extended the number of kinase family members. [Hunter et al., (1985) *Ann. Rev. Biochem.* 54:897–930.] This sequence analysis suggested the number of kinase-related proteins would be large and the family members could be divided into subgroups based upon sequence homology and overall structural similarities. The kinase family can be conveniently divided into gene products that do or do not have extracellular (hormone/growth factor) binding domains.

The close similarity between the kinase portion of src and yes has been apparent for several years. [Kitamura et al., (1982) *Nature* 297:205–208.] Recently, sequencing of additional genes has extended this homology to fgr, [Naharro et al., (1984) *Science* 222;63–66] lck, [Marth et al., (1985) *Cell* 43:393–404. syn, [Semba et al., (1986) *Proc. Natl. Acad. Sci. USA* 83:5459–5463] and lyn [Yamanashi et al., (1987) *Mol. and Cell Biol.* 1:237–243]. All six of these genes encode proteins of approximately the same size 55–65 kd, and the genes share intron/exon borders indicating they evolved from the same ancestral proto-oncogene. However, each gene is located on a separate chromosome and expresses different proteins in different tissues.

Many additional kinase family members can also be placed into subgroups. Mos [Van Beveran et al., (1981) *Nature* 289:258–262] is closely related to pim-1 [Selten et al., (1986) *Cell* 46:603–611], one of the preferred integration sites of Moloney leukemia virus. Abl [Reddy et al., (1983) *Proc. Natl. Acad. Sci. USA* 80:3623–3627] is closely related to arg [Kruh et al., (1986) *Science* 234:1545–1547]. Fes [Hampe et al., (1982) *Cell* 30:775–785] and fps [Shibuya et al., (1982) *Cell* 30:787–795]. represent the mammalian and avian counterparts of the same gene. Similarly, raf [Sutrave et al., (1984) *Nature* 309:85–88] and mil [Mark et al., (1984) *Science* 224:285–289] are mammalian and avian homologues of the same gene. They are closely related to A-raf/pks [Huleihel et al., (1986) *Mol. and Cell Biol.* 6:2655–2662; Mark et al., (1986) *Proc. Natl. Acad. Sci. USA* 83:6312–6316].

A subgroup that does not have a viral counterpart contains genes that encode protein kinase C, the receptor for phorbal esters. There are at least three closely related genes comprising this subgroup [Coussens et al., (1986) *Science* 233:859–866; Knopf et al., (1986) *Cell* 46:491–502]. Moreover, one of the genes can encode two proteins via alternative exon usage [Ohno et al., (1987) *Nature* 325:161–166]. Other more distantly related cytoplasmic kinases include cAMP- and cGMP-dependent protein kinase [Shoji et al., (1981) *Proc. Natl. Acad. Sci USA* 78:848–851; Takio et al., (1984) *Biochemistry* 23:4207–4218], as well as myosin light chain kinase [Takio et al., (1985) *Biochemistry* 24:6028–6037]. Several transmembrane kinases have also been sequenced in the past few years.

A gene closely related to the human epidermal growth factor receptor (HER) has also been found in humans (HER-2) [Coussens et al. (1985) *Science* 230:1132–1139] and rats (neu) [Bargmann et al., (1986) *Nature* 319:226–230]. The growth factor that binds to ros [Neckameyer et al., (1985) *J Virol.* 53:879–884] is not known although the sequence is most closely related to the insulin receptor (HIR) [Ullrich et al., (1985) Nature: 313, 756–761]. The colony stimulating factor 1 receptor, FMS [Hampe et al., (1984) *Proc. Natl. Acad. Sci. USA* 81:85–89], forms a subgroup with kit [Besmer et al., (1986) *Nature* 320:415–421] and the receptor for platelet-derived growth factor, PDGF-R [Yarden et al., (1986) *Nature* 323:226–232]. In addition, sequences for the trk [Martin-Zanca et al., (1986) *Nature* 319:743–748] and met-8 [Dean et al., (1985) *Nature* 318:385] oncogeneses have been published, although the corresponding growth factors are not known.

A similar although not as extensive expansion has also been seen for the nucleotide binding proteins represented by the ras oncogene family. Sequence data indicate bas [Reddy et al., (1985) *J. Virol.* 53:984–987] is the mouse form of H-ras [Dhar et al., (1982) *Science* 217:934–937], and that the H- and K-ras products differ principally at the carboxyl region [Tsuchida et al., (1982) *Science* 217:937–939]. Through alternative exons K-ras can encode 2 proteins (4A and 4B) [McGrath et al., (1983) *Nature* 310:501–506]. A third member, N-ras, also diverges from H- and K-ras in this region [Taparowsky et al., (1983) *Cell* 34:581–586]. Another closely related gene is R-ras [Lowe et al., (1987) *Cell* 48:137–146], although this gene is closely related to the three ras genes that have evolved from the same ancestral gene, R-ras has different intron/exon boarder. Another gene, rho 7[Madule et al., (1985) *Cell* 41:31–40], has scattered regions of homology with ras. Furthermore, a third group, ral, also has similar regions of homology [Chardin et al., (1986) *EMBO J.* 5:2203–2208]. Moreover, a yeast gene ypt [Gallwitz et al., (1983) *Nature* 306:704–707] has regions of homology with ras and this gene is distinct from the two yeast genes that have extensive homology with ras; i.e., they are more like R-RAS.

Other genes that also have homology with ras include the G proteins [Itoh et al., (1986) *Proc. Natl. Acad. Sci. USA* 83:3776–3780] as well as transduction and elongation factor, Tu (Lochrie et al., (1985) *Science* 228:96–99]. The G proteins are composed of subunits that stimulate $(G_s)$ and inhibit $(G_i)$ adenylate cyclase. Another related protein $(G_o)$, has an unknown function. These proteins exists in a variety of different forms that have closely related sequences.

The nuclear proteins myb [Rushlow et al., (1982) *Science* 216,1421–1423], myc [Colby et al., (1983) *Nature* 301:722–725] and fos [van Straaten et al., (1983) *Proc. Natl. Acad. Sci. USA* 80:3183–3187] comprise another family of oncogenes that are related more by cellular location than sequence. However, additional genes related to these oncogenes have been identified. N-myc [Stanton (1986) *Proc. Natl. Acad. Sci. USA* 83:1772–1776] and L-myc [Nau et al., (1985) *Nature* 318:69–73] sequences have been published, and unpublished related sequences have been identified. Moreover, the sequences are distantly related to fos. A related fos (r-fos) [Cochran et al., (1984) *Science* 226:1080–1082] sequence has been published, and unpublished data indicate a phosphorylase inhibitor has limited homology as does the jun oncogene.

Another group of nuclear oncogene-related proteins include steroid and thyroid hormone receptors. Although only one sequence related to erb A has been published [Sap et al., (1986) *Nature* 324:635–640; Weinberger et al., (1986) *Nature* 324:641–646], hybridization studies indicate at least two related sequences are present in the human genome [Weinberger et al., (1986) *Nature* 324:641–646]. Steroid receptor sequences indicate erb A (the thyroid hormone receptor) is part of a superfamily that includes several receptors (estrogen, glucocorticoid, progesterone, aldosterone) [Greene et al., (1986) *Science* 231:1150–1153; Hollenberg et al., (1985) *Nature* 318:635–641; and Connelly et al., (1986) *Science* 233:767–770].

In the growth factor group only the PDGF-1 chain [Doolittle et al., (1983) Science 221:275–277 and Waterfield et al., (1983) Nature 304:35–39] has sequence homology to sis (PDGF-2). However, other growth factors [Gregory (1975) Nature 257:325–327; Marguardt et al., (1983) Proc. Natl. Acad. Sci. USA 80:4684–4688] (EGF and TGF) bind to the product of the erb B protooncogene, and CSF-1 [Kawasaki et al., (1985) Science 230:291–296] binds to the fms protooncogene. Moreover, TGF [Derynk et al., (1985) Nature 316:701–705], forms another subgroup by virtue of homologies with Mullerian inhibitory substance [Cate et al., (1986) Cell 45:685–698], and the three chains that are found in the various forms of inhibition [Mason et al., (1985) Nature 318:659–663 and Vale et al., (1986) Nature 321:776–779].

Finally, sequences representing two of the preferred integration sites of MMTV have been published [Van Ooyen et al., (1984) Cell 39:233–240 and Moore et al., (1986) EMBO J. 5:919–924].

Thus, in the past few years, the number of related published sequences has increased dramatically. These sequences suggest that a limited number of pathways controlling cell division and differentiation exist but that many different members may participate in this control.

An example of transduction of only a portion of a cellular gene by a retrovirus is the erb B oncogene. The erb B oncogene is highly homologous to a portion of the ECG receptor [Ullrich et al., Nature 309:418 (1984)], as already noted. Sequence analysis of the entire receptor gene demonstrates the relatedness of erb B with the entire intracellular domain, the transmembrane domain, and a portion of the extracellular domain.

The protein encoded by the viral oncogene and the corresponding, homologous protein within the host cell are both referred to herein as oncoproteins, although the cellular oncoprotein is typically larger and is present in small quantities in normal cells, and thus need not only be associated with neo-plastic states. In addition, oncoproteins encoded by related oncogenes can have different molecular weights, e.g., the p85 and p108 oncoproteins encoded by v-fes$^{ST}$ and v-fes$^{GA}$, respectively, and the 100–105 kilodalton (also kd or K dalton) protein of normal mink cells thought to be encoded by the c-fes gene. [Sen et al., Proc. Natl Acad. Sci. USA, 80, 1246–1250 (1983).] The term oncoprotein is thus used generally herein for proteins whose genes and amino acid residue sequences are homologous, at least in part, as discussed hereinafter.

The oncoprotein is generally not present in the virus particle that infects the cell, but is only expressed after infection and transformation. The corresponding cellular oncoprotein is expressed at most minimally in normal cells and to a greater extent in neoplastic cells. Thus, the oncoprotein cannot typically be obtained from the virus. In addition, isolation of oncoproteins from cells is made difficult because of small amount present, the complex mixture of proteins found in normal cells, and the relatively small amount of such proteins present even in transformed cells.

Oncoproteins encoded by v-onc and c-onc genes thus typically contain large sequences of amino acid residues that are homologous, but nevertheless are not usually identical. In addition, oncoproteins encoded by genes of different viral strains, each of which contains ostensibly the same oncogene, have been found to have slight variations in their amino acid residue sequences as exemplified above, and by the four published sequences of the ras gene which differ at the position of the twelfth amino acid residue. Thus, even when oncoproteins are in hand, it may be difficult to distinguish among them.

Immunologically induced receptor molecules such as monoclonal and polyclonal antibodies or the idiotype-containing portions of those antibodies are useful in purifying protein ligands to which they bind, as diagnostic reagents for assaying the presence and quantity of the protein ligands, as well as for distinguishing among homologous protein ligands.

The difficulties associated with obtaining quantities of oncoproteins typically militate against the preparation of receptors to those oncoproteins, although whole cell-induced monoclonal antibodies to v-fes and v-fps encoded oncoprotein have been reported by Veronese et al., J. Virol., 43, 896–904 (1982). In addition, even were whole proteins available for use as immunogens for inducing the production of such receptors, the use of large protein molecules as immunogens produces antisera containing polyclonal antibodies to the numerous epitopes of the large protein molecules.

Hybridoma and monoclonal antibody techniques utilizing whole proteins or large protein fragments as immunogens have been useful in narrowing the immunological response to such immunogens. However, such technology as heretofore practiced has been extremely time consuming and has provided only a relatively small number of hybridomas that secrete useful antibodies that recognize the immunogen. Moreover, even when successful, such techniques cannot be predictive of the chemical identity of epitope to which the receptor molecules are raised. Consequently, even after immunogen-recognizing receptors are produced, the obtaining of receptors to specific, chemically identified epitopic portions of the protein ligand has been a hit or miss operation that still further reduces the number of useful hybridomas that are ultimately produced.

Arnheiter et al., Nature, 294, 278–280 (1981) reported on the production of monoclonal antibodies that were raised to a polypeptide that contained 56 amino acid residues and corresponded in amino acid residue sequence to the carboxyterminal portion of an intact interferon molecule. The 56-mer polypeptide thus corresponded to approximately one-third of the sequence of the intact molecule.

Arnheiter et al. reported on the production of eleven monoclonal antibodies. However, only one of those eleven monoclonal antibodies bound both to the polypeptide immunogen and also to the intact interferon molecule. In addition, that binding was not very strong as judged by the 3000-fold excess of intact interferon required to compete the antibody away from the synthetic polypeptide. None of the other monoclonal antibodies bound to the intact molecule.

In addition, the production of the hybridomas secreting those monoclonal antibodies required the spleens from three immunized mice. The low yield of the desired interferon-binding monoclonal antibodies, and the fact that three mouse spleens were needed for the preparation of those hybridoma cell lines indicates that those workers were relatively unsuccessful in their efforts.

Lerner et al. have been successful in obtaining protection of animals by the use of vaccines against pathogens by utilizing synthetic amino acid residue sequences of short to moderate length as immunogens. See Sutcliffe et al., Science, 219, 495–497 (1983).

However, it must be understood that until the present invention, successful preparation of hybridomas and their secreted monoclonal receptors differs from the successful preparation of a vaccine containing oligoclonal receptors.

Thus, for a high yield monoclonal antibody preparation, it is necessary to stimulate B-cells to secrete large amounts of avid antibodies. On the other hand, for a synthetic vaccine, a wider spectrum of oligoclonal antibodies may be produced in smaller amounts and with lower avidities. In addition, protection of an animal against a pathogen typically requires both T-cell and B-cell activations so that a cellular response and a humoral response, respectively, can be induced in the animal.

A popular explanation for the success of synthetic polypeptide-containing vaccines in generating antibodies that recognize intact proteins and protect animal hosts involves a stochastic model in which the diversity of the immune response allows the observation of an infrequent event; i.e., the polypeptide adopting the confirmation of its corresponding sequence in the native molecule. The concept that moderate-length polypeptides can frequently conform to native structures is contrary to theoretical and experimental studies. Rather, such polypeptides are thought to exist as an ensemble of a large number of transient conformational states that are in dynamic equilibrium. T-Cell activation by, and B-cell production of antibodies raised to, some of that conformational ensemble have been believed sufficient to provide protection upon vaccination.

BRIEF SUMMARY OF THE INVENTION

The present invention contemplates a monoclonal receptor molecule that binds both (a) to a protein ligand encoded by a retrovirus gene, and (b) to a polypeptide of moderate length, about 7 to about 40 residues, and preferably about 10 to about 30 amino acid residues, having an amino acid residue sequence corresponding to an amino acid residue sequence of a portion of the protein encoded by a gene of a retrovirus. The receptor molecule is raised to (induced by) an immunogen containing the polypeptide. Most preferably, the receptor molecule is a monoclonal receptor of the IgG class of immunoglobulins.

Specific, preferred monoclonal receptor molecules of this invention bind to protein encoded by the oncogenes listed below, and also to the polypeptide(s) listed opposite those oncogenes:

| Oncogene | Polypeptide Sequence |
|---|---|
| fes | SDVWSFGILLWETFSLGASPYPNLSNQQTR; SPYPNLSNQQTR; IGRGNFGEVFSG; LMEQCWAYEPGQRPSF; and VPVKWTAPEALNYGR; |
| myb | RRKVEQEGYPQESSKAG; RHYTDEDPEKEKRIKELEL; and LGEHHCTPSPPVDHG; |
| fos | SGFNADYEASSRC; LSPEEEEKRRIRRERNIKMAAAKC; and RKGSSSNEPSSDSLSSPTLL; |
| sis | RKIEIVRKKPIFKKATV; RVTIRTVRVRRPPKGKHRKC; and |
| ras | YREQIKRVKDSDDVPMVLVGNKC; YTLVREIRQHKLRKLNPPDESGPGC; YTLVREIRQYRLKKISKEEKTPGC; KLVVVGARGVGK; KLVVVGASGVGK; and KLVVVGAGGVGK; |
| myc | CDEEENFYQQQQQSEL; PAPSEDIWKKFEL; LPTPPLSPSRRSGLC; CSTSSLYLQDLSAAASEC; and CTSPRSSDTEENVKRRT; |

| Oncogene | Polypeptide Sequence |
|---|---|
| mos | LPRELSPSVDSR; IIQSCWEARGLQRPSA; LGSGGFGSVYKA; RQASPPHIGGTY; and TTREVPYSGEPQ; |
| erb-A | KSFFRRTIQKNLHPTYSC; VDFAKNLPMFSELPCEDQ; and CYGHFTKIITPAITRVVDFA; |
| erb-B | ENDTLVRKYADANAVCQ; LGSGAFGTIYKG; and IMVKCWMIDADSRPKF; |
| PDGF-2 | SLGSLTIAEPAMIAECK; RKIEIVRKKPIFKKATV; and RVTIRTVRVRRPPKGKHRKC; |
| PDGF-1 | SIEEAVPAECKTR; |
| EGF | CLHDGVCMYIEALDKYAC; |
| abl | LMRACWQWNPSDRPSF; LGGGQYGEVYEG; and LWEIATYGMSPYPGIDLSQVY; |
| fms | FMQACWALEPTRRPTF; and LGTGAFGLVVEA |
| src | LMCQCWRKDPEERPTF; LGQGCFGEVWMG; and CGSSKSKPKDPSQRRRS; |
| yes | LMKLCWKKDPDERPTC; and LTELVTKGRVPYPGMVNREVL; |
| fgr | LTELTTKGRVPYPGMGNGEVL; |
| bas | KLVVVGAKGVGK; |
| int-1 | LHNNEAGRTTVFS; |
| mil/raf | LVADCLKKVREERPLF; and IGSGSFGTVYRG; |
| ros | LGSGAFGEVYEG; VWETLTLGQQPYPGLSNIEVL; and LMTRCWAQDPHNRPTF. |

The present invention also contemplates a method of producing monoclonal receptor molecules to a protein molecule ligand. In this method, an immunogenic polypeptide of moderate length (about 7 to about 40 residues), preferably synthetically produced, or a conjugate of that polypeptide bound to a carrier is provided. The amino acid residue sequence of that polypeptide corresponds to a portion of the amino acid residue sequence of a protein ligand. That immunogenic polypeptide, when bound as a conjugate to a carrier of keyhole limpet hemocyanin and used to immunize a mouse, is sufficiently immunogenic and antigenic to provide a 50 percent binding titer of the immunized mouse's serum to the polypeptide of at least about a 1:400 dilution after three immunizations, each containing at least 10 micrograms of polypeptide in the conjugate and using complete Freund's adjuvant for the first immunization and alum as adjuvant in the second and third immunizations.

A mammal is hyperimmunized with the immunogenic polypeptide or a conjugate of that polypeptide bound to a carrier to provide a hyperimmune serum that exhibits a 50 percent binding titer to the polypeptide of at least about a 1:400 dilution. The receptor molecules of that serum also bind to the protein molecule ligand to which the polypeptide corresponds in amino acid residue sequence.

The hyperimmunized mammal is maintained for a period of at least about 30 days after the administration of the immunization that produces a 50 percent binding titer of a dilution of at least about 1:400. A booster immunization, as by intravenous injection, is thereafter administered to the animal.

Antibody-producing cells such as spleen cells (splenocytes) of the boosted mammal are fused with myeloma cells within a period of about three to about five days from the day of booster administration to prepare hybridoma cells. The hybridoma cells so prepared are assayed for the production of monoclonal receptor molecules that bind to a protein molecule ligand to a portion of which the immunogenic polypeptide corresponds in amino acid residue sequence. Preferably, the hybridoma cells are also assayed for the production of monoclonal receptor molecules that bind to the polypeptide.

The hybridoma cells that produce monoclonal receptor molecules that bind to the protein molecule ligand are then cultured to prepare an additional quantity of such cells. In preferred practice, those hybridoma cells that are cultured are also those that produce monoclonal receptors that bind to the polypeptide.

Another embodiment of the present invention contemplates a diagnostic system such as a kit for assaying for the presence of an oncoprotein ligand. This system includes at least a first package containing monoclonal receptor molecules of this invention. Admixing a predetermined amount of those receptors with a predetermined amount of an aqueous composition to be assayed for the presence of an oncoprotein ligand forms a receptor-ligand complex by an immunological reaction when the oncoprotein ligand includes an amino acid residue sequence corresponding to the amino acid residue sequence of the polypeptide bound by the receptor molecule. The presence of the complex can be identified by a label that is preferably contained in a second package of the system. A preferred oncoprotein ligand-containing aqueous composition includes a cell extract, amniotic fluid, urine, and concentrated urine. The urine or urine concentrate is easily obtained by noninvasive means and is readily concentrated to allow the implementation of the diagnostic test set forth herein. Cell extracts and media conditioned by transformed cells are also suitable aqueous compositions containing oncoprotein ligands.

An assay method is another contemplated embodiment of this invention. Here, a body sample to be assayed for the presence of an oncoprotein ligand such as serum, a cell extract, amniotic fluid, urine or a urine concentrate is admixed in a liquid solution containing anti-oncoprotein receptor molecules. The admixture so formed is maintained for a period of time sufficient for a complex (immunocomplex; reaction product or immunoreactant) to form between an oncoprotein ligand and receptor molecule (antigen-antibody complex). The presence of a complex is thereafter determined.

Where urine, as obtained or in concentrated form, is the composition to be assayed, anti-oncoprotein receptors of any origin, e.g., polyclonal, oligoclonal or monoclonal, can be used in the instant invention. The monoclonal antibodies of this invention are utilized with other samples to be assayed. Determinations of the presence of an immunoreactant are typically carried out using a radioisotope- or enzyme-labeled antibody or *Staphylococcus aureus* protein A that binds to the receptor of the formed immunocomplex.

A particularly novel aspect of this invention is the use of urine as a body sample. The assays described herein may be performed using concentrated urine as described, or may be performed using urine as obtained. Oncogene-related proteins have not been heretofore identified in urine samples.

The assay aspects of this invention can be conducted using a plurality of oncoprotein-related polypeptide ligands to provide a pattern of immunological reactivity for a particular assayed sample. Patterns obtained are compared to patterns obtained from individuals having known disease states to provide a diagnosis.

A method for ascertaining the presence of a female fetus in utero is also contemplated. Here, a sample of boiled, reduced, and preferably concentrated urine from a pregnant mother is admixed with receptor molecules that immunoreact with a polypeptide that has a formula, written from right to left and in the direction from amino-terminus to carboxy-terminus, selected from the group consisting of:

(i) LMEQCWAYEPGQRPSF, and
(ii) YREQIKRVKDSDDVPMVLVGNKC, the urine sample being collected during the period about 16 through about 20 weeks into the pregnancy. The admixture is maintained for a time period sufficient for the receptor molecules to immunoreact with an oncoprotein ligand present in the urine sample. The presence of a particular immunoreactant is thereafter assayed for. The immunoreactant is that formed between the receptor molecules and an oncoprotein ligand that exhibits a relative molecular mass in a 5–17 percent polyacrylamide gel of about 40 kilodaltons for the receptor molecules that immunoreact with polypeptide (i), above, and about 55 kilodaltons for the receptors that immunoreact with polypeptide (ii), above. The presence of an immunoreactant with either of those receptor molecules indicates the presence of a female fetus in utero. The receptor molecules are preferably monoclonal.

In yet another embodiment of the invention, monoclonal receptor molecules form the active, binding portions of an affinity-sorbant useful for binding and purifying oncoprotein ligands. Here, the receptors are linked to a solid support that is chemically inert to the oncoprotein such as agarose or cross-linked agarose. The affinity sorbant so prepared may then be admixed with an aqueous composition containing a protein ligand to form a reversible receptor-ligand complex when the protein ligand has an amino acid residue sequence corresponding to the amino acid residue sequence of the polypeptide bound by the receptor. The complex so formed can be thereafter dissociated to provide the protein ligand in a purified form.

The present invention provides several benefits and advantages.

One benefit of the invention is monoclonal receptor molecules that bind to epitopes contained in polypeptides of known amino acid residue sequence.

Another benefit of the invention is that monoclonal receptor molecules can be raised that bind to epitopes contained in known amino acid residue sequences of, oncoprotein ligands where those protein ligands are not needed to induce the production of the receptor molecules.

One of the advantages of the present invention is the high yield method of producing monoclonal receptors that bind to both an immunogenic polypeptide of moderate length and to a protein ligand molecule to whose amino acid residue sequence the polypeptide corresponds in part.

Another advantage of this invention is the provision of a diagnostic system such as a kit containing monoclonal receptor molecules capable of assaying for the presence of an oncoprotein.

A further advantage of this invention is the provision of a diagnostic method that can be accomplished using body samples obtained by non-invasive means.

Another advantage of this invention is that proteins of differing molecular weights may be detected allowing a differential and highly accurate assessment of the precise oncogenes being expressed within the organism.

A further advantage of this invention is the provision of a diagnostic method that allows prognostication of fetal development, or other growth states including neoplasia that utilizes urine of the mother or individual, respectively, in a non-invasive assay.

Still further benefits and advantages of the present invention will be apparent to those skilled in the art from the description and claims that follow.

BRIEF DESCRIPTION OF THE DRAWINGS

In the drawings forming a part of this disclosure:

FIG. 1 is a photograph of an autoradiograph illustrating an immunological assay for detecting the presence of the ST-FeSV v-fes oncoprotein. Cell extracts from approximately $10^5$ MSTF cells, a productively transformed mink cell line infected with Snyder-Theilen strain of feline sarcoma virus (ST-FeSV) and feline leukemia virus-B (FeLV-B) [Sen et al., *Proc. Natl. Acad. Sci. USA*, 80,1246–1250 (1983)], were electrophoresed onto a 5–17 percent polyacrylamide gel and then transferred to nitrocellulose sheets. The transferred proteins were then reacted with supernatants from hybridoma tissue cultures denominated S10F03 (lane 1) or S22C06 (lane 2) (ATCC designations ATCC HB 8596 and ATCC HB 8595, respectively) or an anti-influenza hemagglutinin hybridoma used as a negative control. This procedure of polyacrylamide gel separation followed by transfer to nitrocellulose and visualization is referred to hereinafter as a Western blot procedure. Protein visualization was accomplished as described in the Materials and Methods section, hereinafter.

Figure 2:
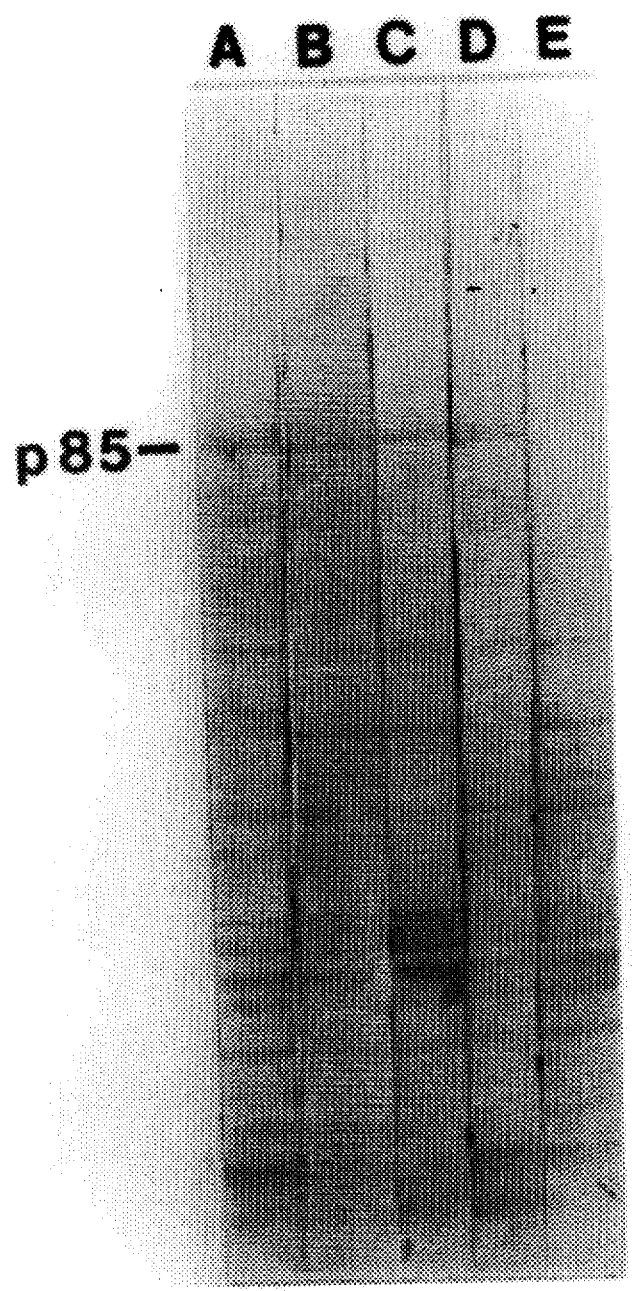
FIG. 2 is a photograph of an autoradiograph illustrating an immunological assay for detecting the presence of the FeSV fusion protein denominated p85 (85 kilodaltons; 85K daltons) by Western blot procedures similar to those of FIG. 1. Cell extracts of approximately $2 \times 10^6$ MSTF cells were electrophoresed into a 5–17 percent polyacrylamide gel, and then electrophoretically transferred to nitrocellulose strips. The strips of nitrocellulose were incubated with 5 milliliters each of hybridoma culture supernatant diluted 1:50 from hybridomas denominated S10F03 (lane A); P43D09 (lane B); P42C10 (lane C); P44E11 (lane D); or with $R_2O6B08$, an anti-Rauscher gp70 protein receptor-producing hybridoma [Niman and Elder, *Proc. Natl. Acad. Sci. USA*, 77, 4524–4528 (1980)], as a negative control (lane E).

Binding was visualized by addition of peroxidase labeled rabbit anti-mouse IgG as is discussed in the Materials and Methods section, hereinafter. The marker "p85–" at the left side of FIG. 2 illustrates the migration position of the 85k dalton ST-FeSV polyprotein encoded by the fes gene.

As can be seen from the proteins in lane E, this technique permits visualization of protein molecules that are not specifically bound by the monoclonal receptors of this invention. Subtraction of the non-specifically bound proteins visualized in lane E from the proteins visualized in lanes A–D illustrates that the only specifically bound protein is the p85 oncoprotein encoded by v-fes.

Figure 3:
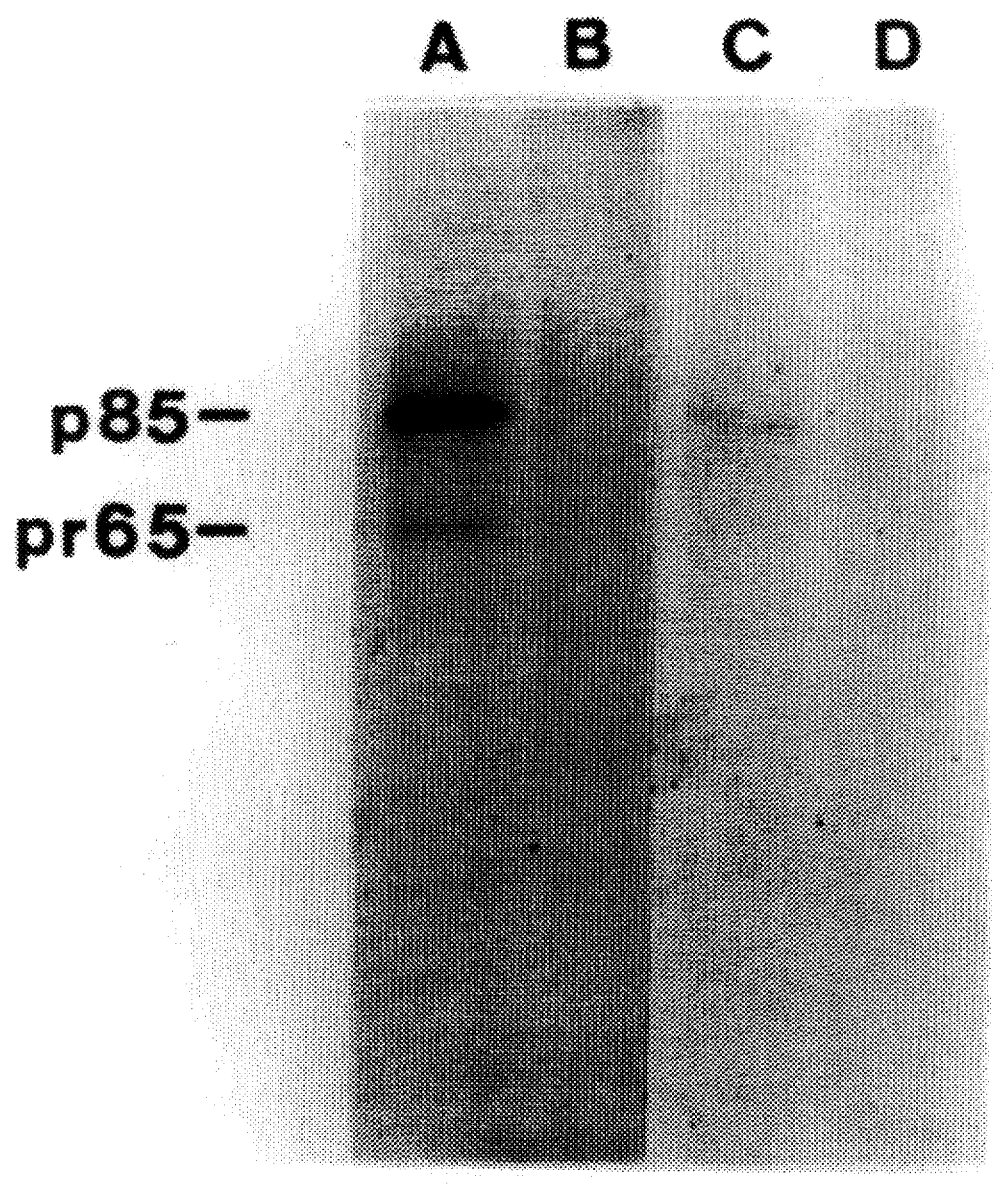

FIG. 3 is a photograph of an autoradiograph illustrating an immunoprecipitation assay for the presence of the $^{32}$P-labeled FeSV fusion protein denominated p85. CCL64 mink cells (MSTF cells; lanes B and D) or those infected with FeLV-B and FeSV (MSTF cells; lanes A and C) were each labeled for 2 hours with 1 microcurie of $^{32}$P. The labeled cell extracts were then incubated with 5 microliters of goat anti-FeLV p15 antibodies (lanes A and B) or with 50 microliters of supernatant from cultured hybridoma S10F03 (lanes C and D). Immune complexes so prepared were collected using *Staphylococcus aureus* bacteria expressing protein A. The precipitated complexes so collected were washed, and were then dissociated into their component parts. The proteins were thereafter analyzed under reducing denaturing electrophoresis using a 5–17 percent polyacrylamide gel.

The markers "p8P–" and "pr65–" at the left of FIG. 3 illustrate migration positions of the 85K dalton ST-FeSV fusion protein encoded by the fes gene, and the 65K dalton FeLV gag-precursor protein.

Figure 4:
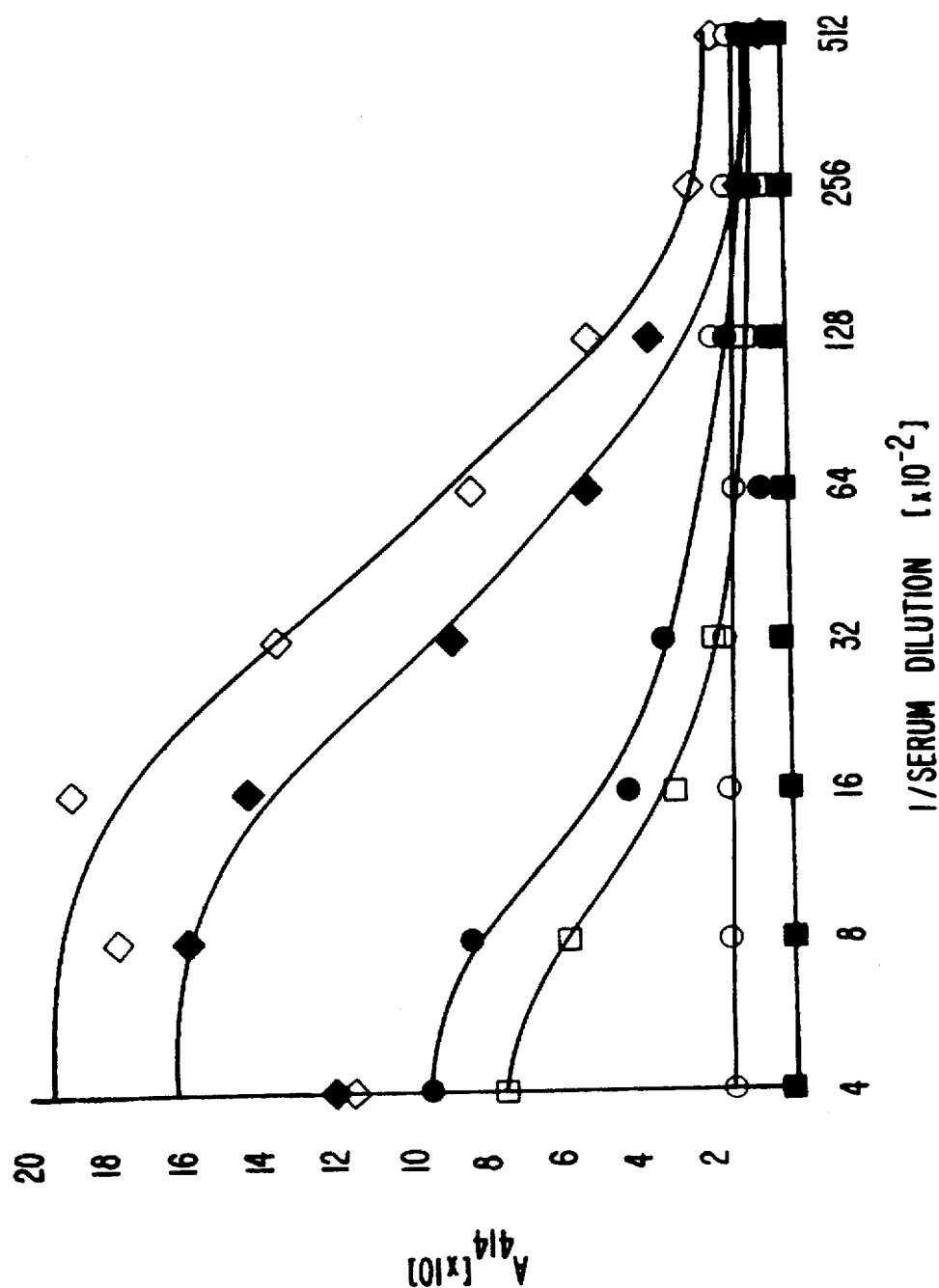

FIG. 4 is a graph illustrating immunoreactivities of oligoclonal antibodies raised to synthetic polypeptides corresponding in amino acid residue sequence (i) to positions 139 through 155 of the predicted sequence of the simian sarcoma virus transforming protein denominated p28$^{sis}$ [Devare et al., *Proc. Natl. Acad. Sci. USA*, 80, 731–735 (1983)] identified hereinafter as polypeptide (o) or number 113 and as PDGF 2(73–89), and (ii) to residues 2 through 18 of the predicted amino acid residue sequence of the avian myeloblastosis virus oncoprotein [Rushlow et al., *Science*, 216, 1421–1423 (1982)] identified hereinafter as polypeptide (d) or number 131. The synthetic polypeptides conjugated to keyhole limpet hemocyanin (KLH) were used to immunize mice as is discussed generally in the Materials and Methods section.

To test the specificity of oligoclonal antibody containing sera so prepared, 250 nanograms of unconjugated polypeptide or 500 nanograms of KLH were dried onto the bottoms of microliter wells and fixed with methanol as described by Niman and Elder, in *Monoclonal Antibodies and T Cell Products*, Katz ed., CRC Press, Boca Raton, Fla., pp. 23–51 (1982). The remaining portions of the wells were blocked against non-specific protein adsorption using 3% bovine serum albumin (BSA) and a 4 hour incubation period at 37 degrees C.

Into each well of the microliter plate was instilled 25 microliters each of two-fold dilutions of immunized mouse sera, starting with a dilution of 1:400, using tissue culture medium supplemented with 10% fetal calf serum and were incubated with the BSA-blocked polypeptide or KLH for 16 hours a 25 degrees C. After washing 10 times with distilled water, 25 microliters of rabbit anti-mouse kappa antibody (Libbon Bionics Inc., Kensington, Md.) diluted 1:500 with 1% BSA in phosphate-buffered saline (PBS) were added and incubated for 2 hours at 37 degrees C. After an additional 10 washings with distilled water, 25 microliters of goat anti-rabbit IgG conjugated to glucose oxidase and diluted 1:500 with 1% BSA in PBS were added and incubated for 1 hour at 37 degrees C.

The amount of glucose oxidase so bound was determined by addition of 50 microliters of a solution containing 100 micrograms/milliliter of ABTS dye (Boehringer-Mannheim) in the presence of 1.2% glucose and 10 micrograms/milliliter of horseradish peroxidase in 0.1 molar phosphate buffer having a pH value of 6.0. The optical densities of the solutions so prepared are read at 414 nanometers using a Titertech microscanner (Flow Laboratories Inc., Inglewood, Calif.).

Bindings exhibited by oligoclonal antibodies in sera raised to the sis-related and myd-related polypeptides are shown by open and closed symbols, respectively. The antibody antigens are: sis-related polypeptide (c) (●, ○); myb-related polypeptide (d) (■, □); and KLH (♦, ◊).

Figure 5:
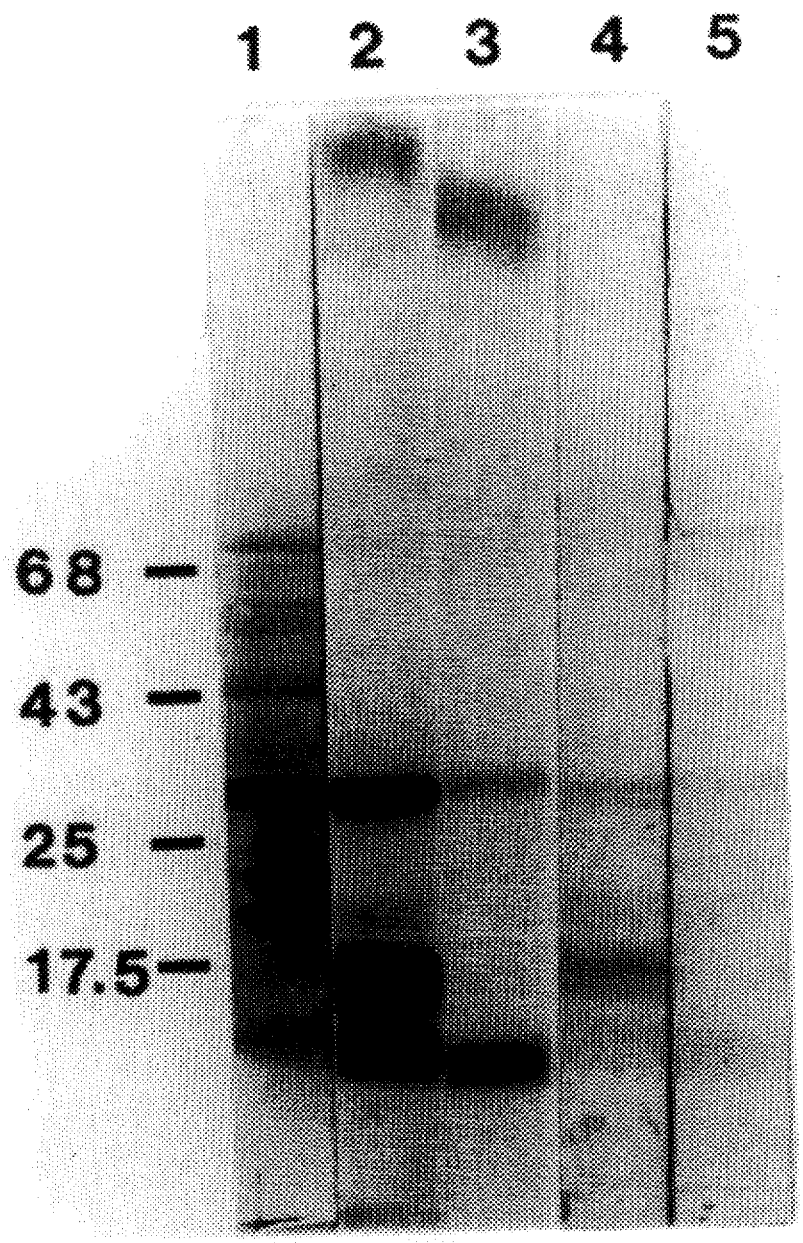

FIG. 5 is a photograph of an autoradiograph illustrating an immunological assay for detecting the presence of non-reduced and reduced platelet-derived growth factor (PDGF) using mouse anti-sera containing oligoclonal antibodies (receptors) induced by synthetic polypeptides (c) and (d) as probes. PDGF extract was purified from outdated platelets as described in the Materials and Methods section.

Purified PDGF extract from approximately 2.5 units of platelets were mixed with a minimal volume of solution containing 0.5% sodium dodecyl sulfate (SDS) and 5 percent of 2-mercaptoethanol. The resulting mixture was boiled for 2 minutes and then electrophoresed therethrough a 5-17 percent polyacrylamide gel. The protein was thereafter electrophoretically transferred to nitrocellulose [Niman and Elder, Virology, 123, 187-205 (1982)] that was thereafter cut into strips, following the Western blot procedure.

The nitrocellulose strips so prepared were then treated with a solution containing 3% BSA, 0.1% polyoxyethylene (9) octyl phenyl ether (Triton® X-100, Rohm and Haas Company, Philadelphia, Pa.) in PBS to inhibit non-specific protein binding. 4 Milliliters of mouse anti-serum diluted 1:200 were then incubated with the nitrocellulose strips.

After washing 3 times with a solution of 0.1% Triton® X-100 in PBS, the nitrocellulose strips were incubated either with $10^6$ counts per minute of $^{125}$I-labeled Staphylococcus aureus protein A (lanes 2 and 3), or a 1:1000 dilution of peroxidase-conjugated goat anti-mouse serum (Tago, Inc. Burlingame, Calif.), and again washed with 0.1% Triton® X-100 in PBS. The peroxidase conjugate was developed with a solution containing 0.009% $H_2O_2$, 0.0025% 3,3'-dimethoxybenzidine dihydrochloride (Eastman-Kodak Co., Rochester, N.Y.) in a 10 millimolar Tris buffer having a pH value of 7.4. The $^{125}$I labeled strips were developed by exposure on XRP-1 film (Eastman-Kodak Co., Rochester, N.Y.) using Cronex Hi-Plus (E.I. DuPont de Nemours & Co., Wilmington, Del.) intensifying screens at minus 70 degrees C. for 48 hours.

Lane 1 contains the total protein stained with amido black. The purified platelet extract is shown probed with anti-sera raised to the sis-related polypeptide (c) (lanes 2 and 4) or the myb-related polypeptide (d) (lane 3 and 5) as a negative control. External molecular weight standards based on BSA, ovalbumin, chymotrypsinogen and beta-lactoglobulin are shown on the left.

Figure 6:
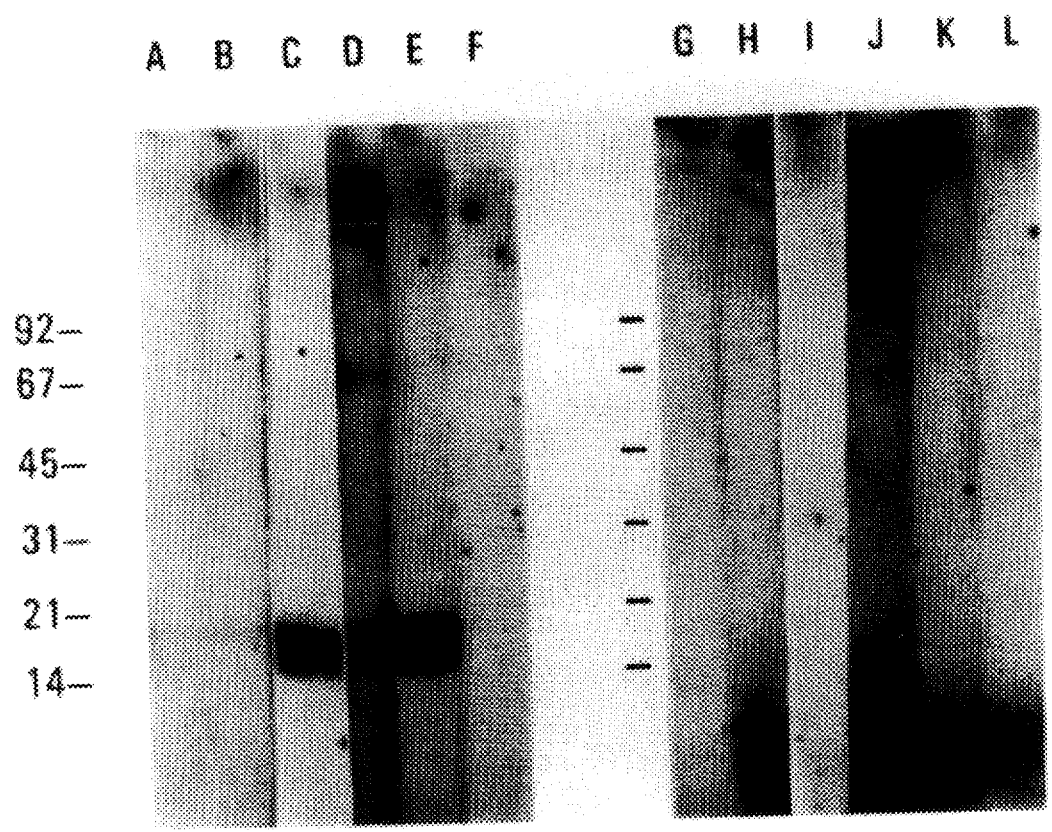

FIG. 6 is a photograph of an autoradiograph illustrating an immunological assay for the presence of PDGF following a Western blot procedure similar to that described hereinbefore. PDGF was boiled in the presence (lanes A-F) or absence (lanes G-L) of 10 percent 2-mercaptoethanol prior to electrophoretic protein separation, following the procedures described in Niman, Nature, 307, 180-183 (1984). Two oligoclonal antibody-containing antisera induced by the amino-terminal twelve amino acid residues of PDGF-1 [denominated PDGF-1(1-12)] were used in lanes A and G, and lanes B and H. Two oligoclonal antibody-containing antisera induced by a polypeptide from a central portion of PDGF-2 [denominated PDGF-2(73-89) and polypeptide (o)] that corresponds to the amino acid residue sequence at positions 139 through 155 of p28$^{sis}$ were used in lanes D and J, and in lanes E and K. Oligoclonal antibody-containing antisera induced by the amino-terminal eighteen residues of PDGF-2 [denominated PDGF-2(1-18)] and by the twenty residues of PDGF-2 located 36-16 residues from the carboxy terminus [denominated PDGF-2(126-145)], corresponding to the sequence at positions 191 through 210 of p28$^{sis}$, were used in lanes C Mnd I, and lanes F and L, respectively. Antibody binding to the proteins was visualized using rabbit anti-mouse IgG followed by $1.0^6$ cpm $^{125}$I-labeled Staphylococcus aureus protein A as described in Niman, supra, and in the Materials and Methods section hereinafter.

Figure 7:
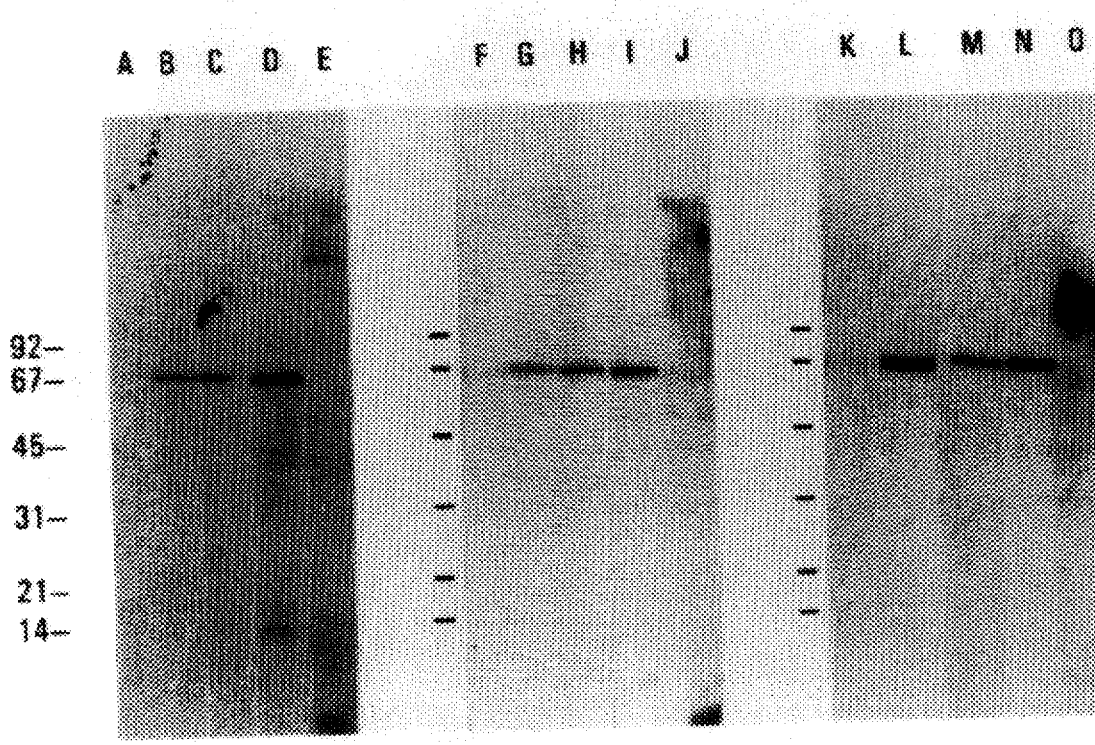

FIG. 7 is a photograph of an autoradiograph illustrating an immunological assay for the presence of a 70,000 dalton protein in three cell lines using a Western blot procedure. An extract from approximately $10^6$ cells per lane from each of SSV-transformed NIH 3T3 cells (lanes A-E), TRD1 cells (a spontaneously transformed Balb/3T3 cell line) (lanes F-J) and MSTF cells [a mink lung line (CCL64) productively infected with FeLV-B and the Snyder-Theilen strain of FeSV] (lanes K-O) was transferred to nitrocellulose sheets following a Western blot procedure. Oligoclonal antibody-containing antisera induced by PDGF-1(1-12) were used in lanes A-C, F-H and K-M. Oligoclonal antibody-containing antisera induced by PDGF-2(73-89) were used in lanes D,E,I,J,N and O. The antisera were incubated with 100 micrograms of polypeptides PDGF-1(1-12) (lanes A,D,F, I,K and N), PDGF-2(1-18) (lanes B,G and L) and PDGF-2(73-89) (lanes C,E,H,J,M and O) prior to being immunoreacted with the transferred cell extracts. Proteins were visualized as described for FIG. 6.

Figure 8:
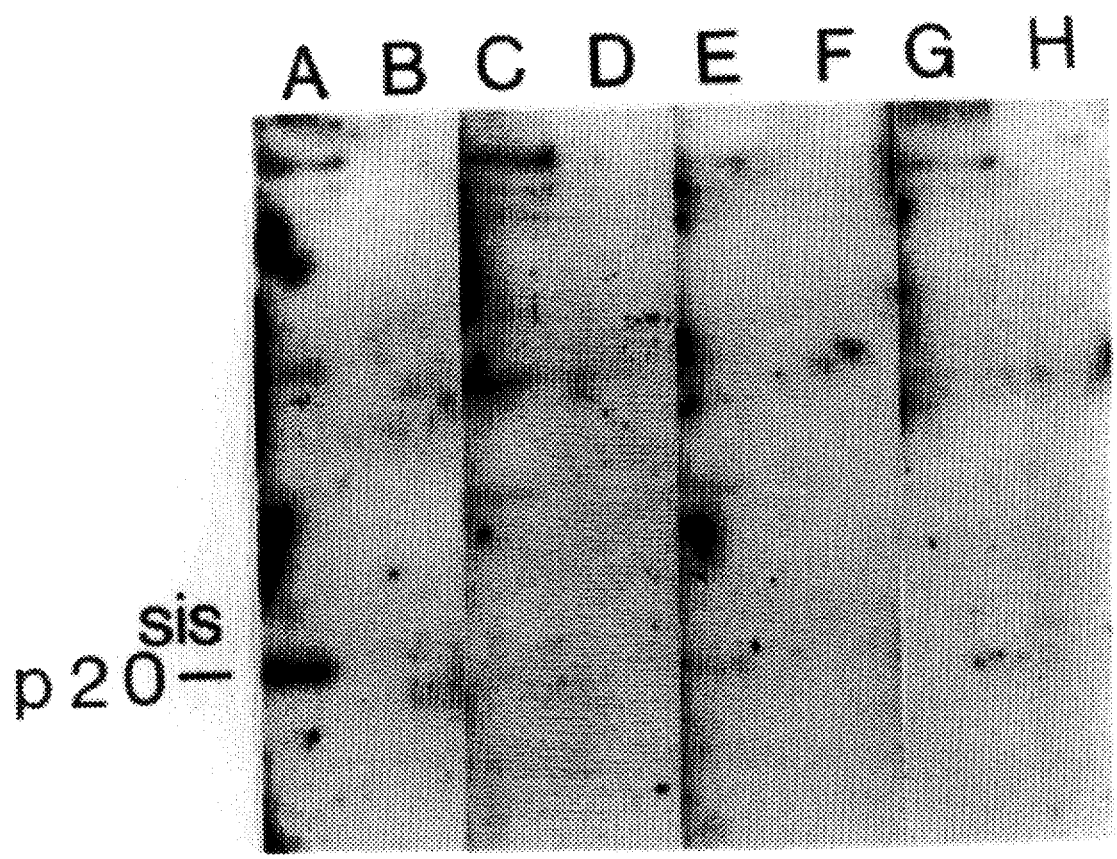

FIG. 8 is a photograph of an autoradiograph illustrating an immunological assay for the presence of p20$^{sis}$ in culture media separately conditioned by SSV-transformed normal rat kidney and normal rat kidney (NRK) cells.

Proteins from concentrated media, equivalent to 25 milliliters of non-concentrated media, conditioned by SSV transformed cells (lanes A,C,E and G) or NRK cells (lanes B,D,R and H) were separated and transferred to nitrocellulose following the Western blot procedure. The transferred proteins were then admixed with oligoclonal antibody-containing antisera induced by PDGF-2(1-18) (lanes A-D) and PDGF-2(73-89) (lanes E-H). Sera were incubated with 100 micrograms of polypeptides PDGF-2(73-89) (lanes A,B,G and H) and PDGF-2(1-18) (lanes C,D,E and F) prior to being immunoreacted with the transferred proteins. Immunoreactions were visualized as described for FIG. 6. The marker "p20$^{sis}$" at the left side of FIG. 8 indicates The position of p20$^{sis}$.

Figure 9:
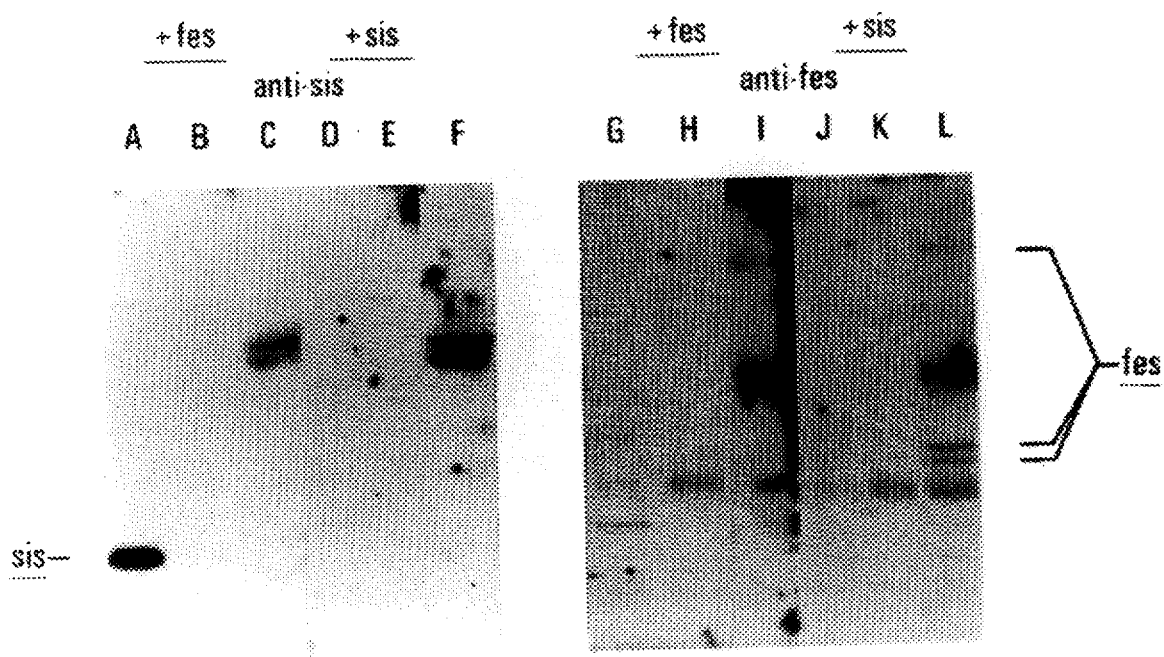

FIG. 9 is a photograph of an autoradiograph illustrating an immunological assay for the presence of proteins encoded by or related to sis and fes antisera in urine from human cancer patients. The liquid body sample in this assay was urine concentrate, obtained as described in the Materials and Methods section. The concentrated urine was electrophoresed into 5-17% polyacrylamide gel and then electrophoresed onto nitrocellulose.

Urine from three donors was concentrated 200-fold, dialyzed and 20 microliters of each concentrate were electrophoresed and the proteins therein transferred to nitrocellulose as described before. These three donors had a rectal tumor (lanes A,D,G and J), a liver tumor (lane B,E,H and K) and a Ewing's sarcoma (lanes C,F,I and L). An oligoclonal receptor-containing antiserum induced by the sis-related polypeptide PDGF-2(73-89) that had been preincubated with the immunizing polypeptide was used in lanes D-F, while the same antiserum that had been preincubated with the fes-related polypeptide corresponding to this sequence located at positions 744-759 of the v-fes$^{ST}$ oncoprotein was used in lanes A-C. Similarly, an oligoclonal receptor-containing antiserum induced by the above fes-related polypeptide that had been preincubated with the immunizing polypeptide was used in lanes G-I, while the same antiserum that had been preincubated with the above sis-related polypeptide was used in lanes J-L. Immunoreaction (binding) between the oligoclonal receptors and the proteins was visualized as described for FIG. 6. The positions of the sis- and fes-related proteins detected in the urine concentrates are indicated on the left and right margins by the markers "sis" and "fes", respectively.

Figure 10:
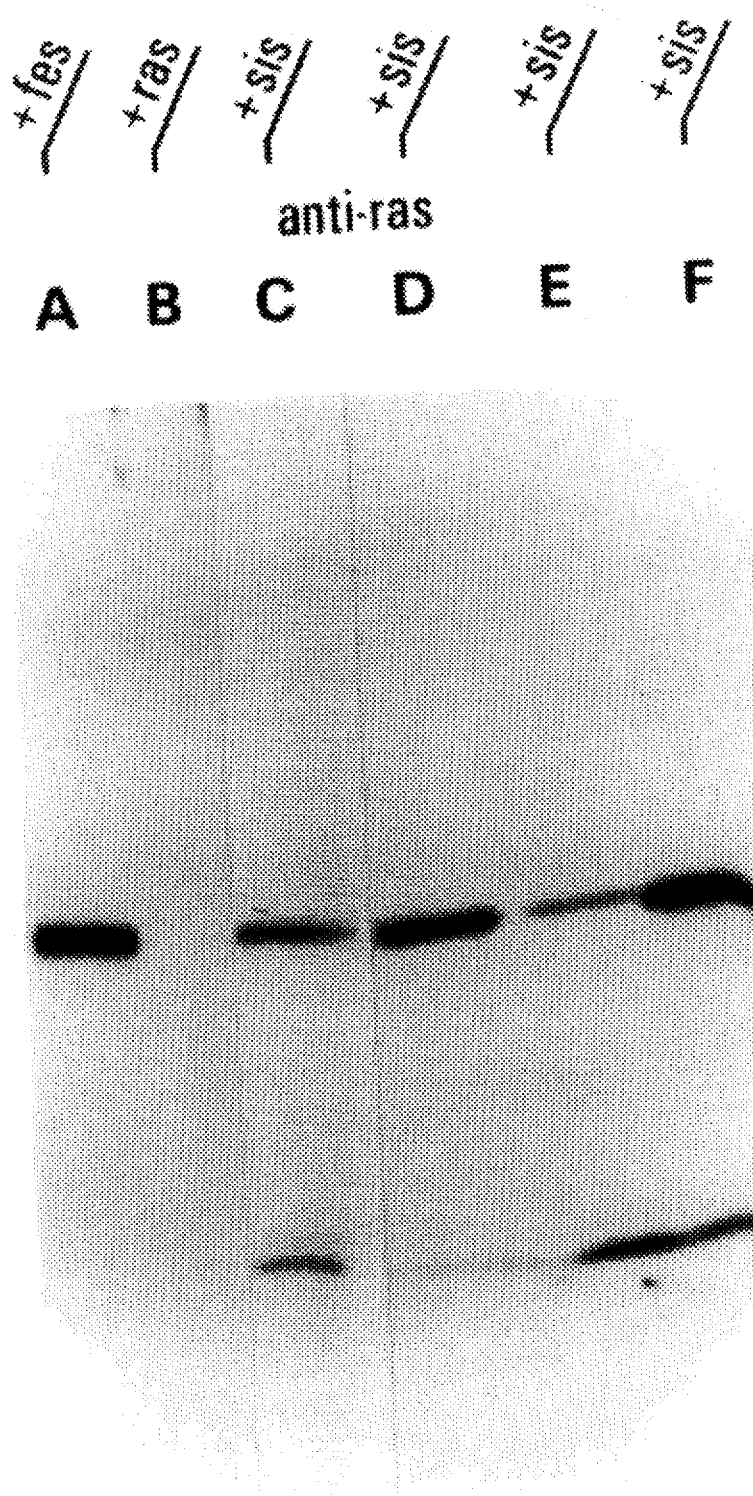

FIG. 10 is a photograph of an autoradiograph illustrating an immunological assay for the presence of ras-related proteins in urine.

Urine was concentrated 250-fold (lanes A and B), 35-fold (lane C), 70-fold (lane D), 75-fold (lane E) and 325-fold (lane F). The urine was dialyzed, 20 microliters of each concentrate were electrophoresed and the proteins therein were transferred to nitrocellulose as described before.

The donors had been diagnosed as normal (lanes A, B and F), or as having one of the following conditions: 38 weeks pregnant (lane C), lymphoma (lane D) and colon carcinoma (lane E). The same normal patient provided the urine samples that were collected 14 days apart and were used in lanes A, B and F.

All urine sample were assayed using 10 microliters of anti-ras ascites fluid induced with residues 96–118 of the p21$^{ras}$ (polypeptide 142) that had been preincubated with residues 744–759 of the polypeptide fes$^{ST}$ (lane A); residues 96–118 of the polypeptide ras$^{Ha}$ (lane B); or residues 138–154 of the polypeptide v-sis (lanes C–F). Immunoreaction (binding) between the oligoclonal receptors and the proteins was visualized as described for FIG. 6. The position of the ras-related proteins detected in the urine concentrates are indicated on the left margin by the marker "ras".

The protein detected that is related to the ras oncogene is detected by a monoclonal antibody secreted by the hybridoma denominated ATCC No. HB 8679 that was raised to ras-related polypeptide 142. This protein of approximately 55K daltons was detected in lane A and the activity was blocked by a preincubation with the immunizing peptide (lane B). Urine collected from the same normal individual contained the same protein two weeks later (lane F). This protein has been detected in the urine of a pregnant patient (lane C) and of a cancer patient (lane D and E).

Figure 11:
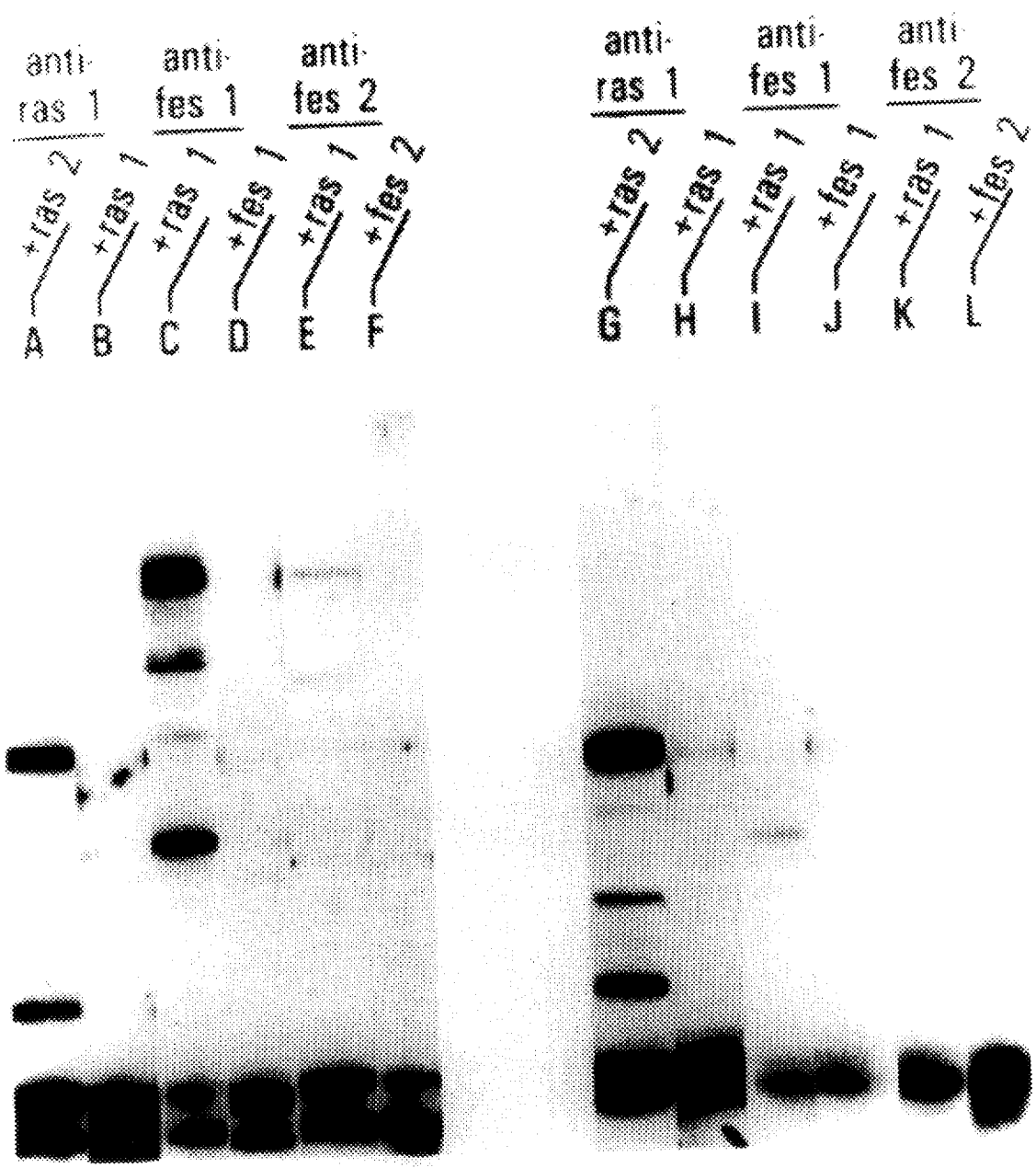

FIG. 11 is a photograph of an autoradiograph illustrating an immunological assay for the presence of a 23K dalton protein in three cell lines using a Western blot procedure. The lanes of the Figure each contained an extract from about 10$^6$ cells per lane from mink lung cell line transformed by the Snyder-Thielen strain of mink lung line sarcoma virus (MSTF) cells (lanes A–F) or from uninfected MSTF cell line CCL64 (lanes G–L). The respective cell extracts were transferred from polyacrylamide gel, onto nitrocellulose sheets, followed by a Western blot procedure.

The extracts were assayed using antisera raised to polypeptide 142 corresponding to residues 96–118 of p21$^{ras}$ ("ras-1"; lanes A, B, G, H) that had been preincubated with polypeptide 141 corresponding to residues 5–16 of v-ras$^{HA}$ ("ras-2"; lanes A, G) or with polypeptide 142 corresponding to residues 96–118 of p21$^{ras}$ ("ras 1"; lanes B,H).

The same cell extracts were assayed with antisera raised to polypeptide 121 corresponding to residues 519–530 of p85-fes ("fes-1"; lanes C,D,I,J) or to residues 744–759 of p85 fes ("fes-2; lanes E,F,K,L). The antisera were preincubated with the fes-1 polypeptide (lanes D,J), with fes-2 polypeptide 744–759 (lanes F,L), or with the ras-1 polypeptide (lanes C,E,I,K) prior to being immunoreacted with the transferred cell extracts. Proteins were visualized as described for FIG. 6.

Figure 12:
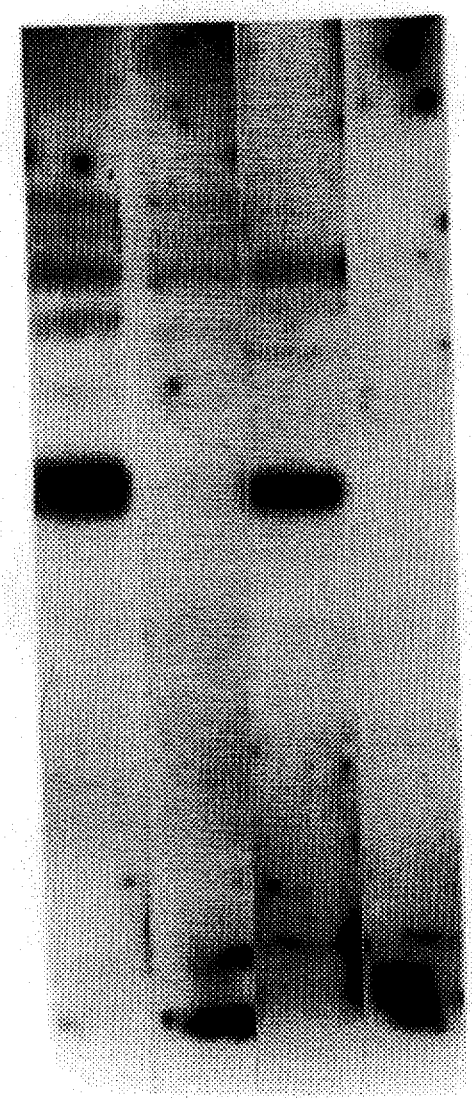

FIG. 12 is a photograph of an autoradiograph illustrating an immunological assay for the presence of a secreted protein in supernatants from spontaneously transformed mouse 3T3 cell line TRD-1 (lanes A,B) or a human T-24 bladder carcinoma line (lanes C,D). The supernatants were assayed for presence of secreted fes-related protein.

The cell lines were grown in the absence of serum and collected after 48 hours of growth. 35 Microliters of 1500:1 concentration of T-24 cell line supernatant or 1000:1 concentration of TRD-1 cells were electrophoresed into a polyacrylamide gel, and then transferred onto nitrocellulose.

Mouse antisera to v-fes$^{ST}$ synthetic polypeptide 127 corresponding to residues 744–759 of p85$^{fes}$ ("fes-2") were utilized for the assay. The antisera were preincubated with synthetic polypeptide 121 corresponding to residues 519–530 of v-fes$^{ST}$ ("fes-1"; lanes A and B), or with the fes-2 polypeptide used to raise the antisera (lanes B and D).

The antisera were then immunoreacted with the transferred cell supernatant. Proteins were visualized as described for FIG. 6.

Figure 13:
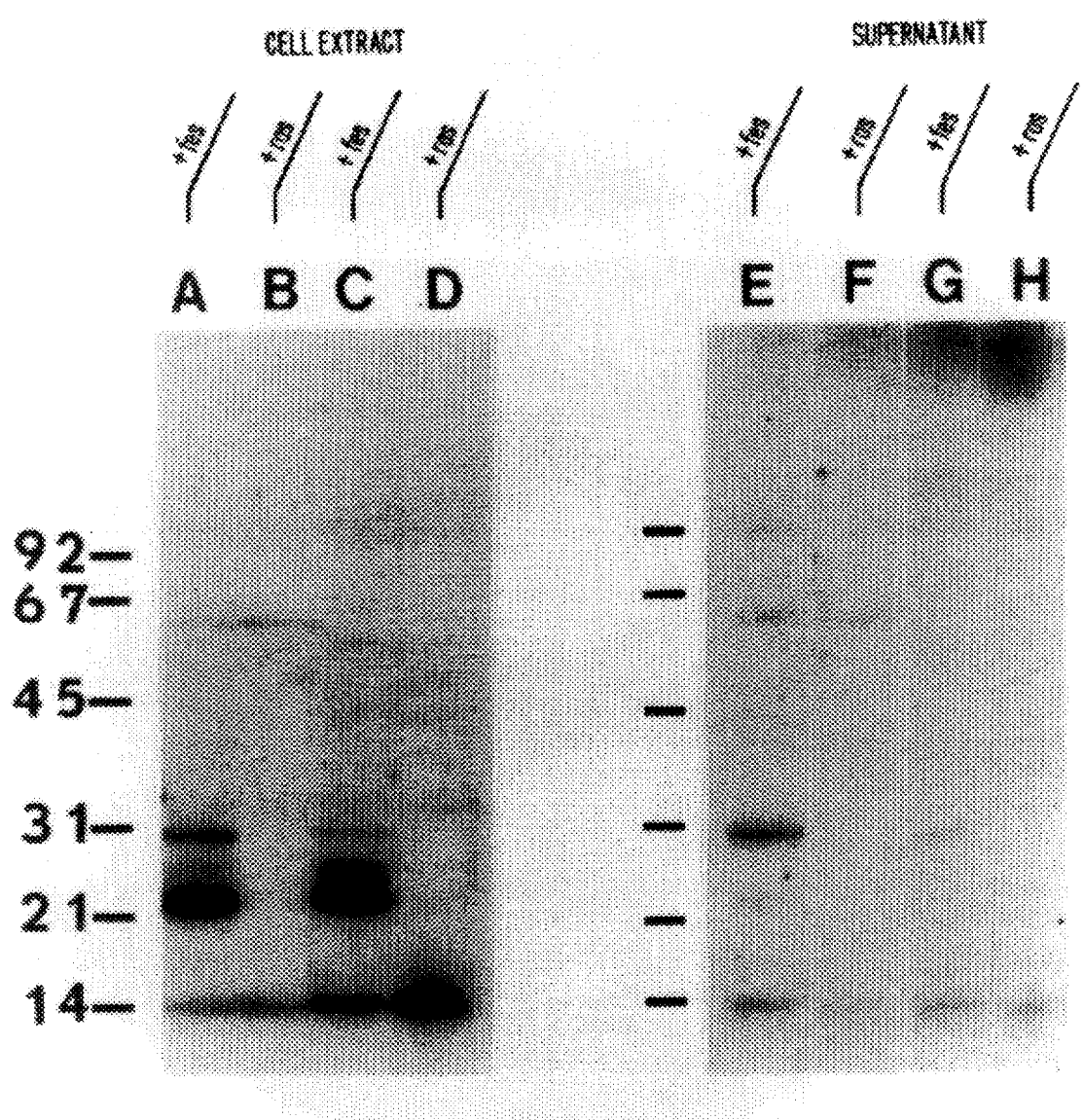

FIG. 13 is a photograph of an autoradiograph illustrating an immunological assay for the presence of a ras related protein in a cell extract using a Western blot procedure.

A cell extract of approximately 10 spontaneously transformed mouse 3T3 cells was used in lanes A–D. 35 Microliters of a 1500-fold concentration of 48 hour supernatants from mouse 3T3 TRD-1 cells were used in lanes E–H. The proteins of the supernatants were electrophoresed in a polyacrylamide gel, and then transferred onto nitrocellulose.

Oligoclonal antibody-containing antisera to polypeptide 142 corresponding to residues 98–118 of v-ras$^{HA}$ were preincubated with an unrelated fes polypeptide (lanes A,C, E,G) or the ras polypeptide used for the immunizations (lanes B,D,F,H). Proteins were visualized as described in FIG. 6.

Figure 14:
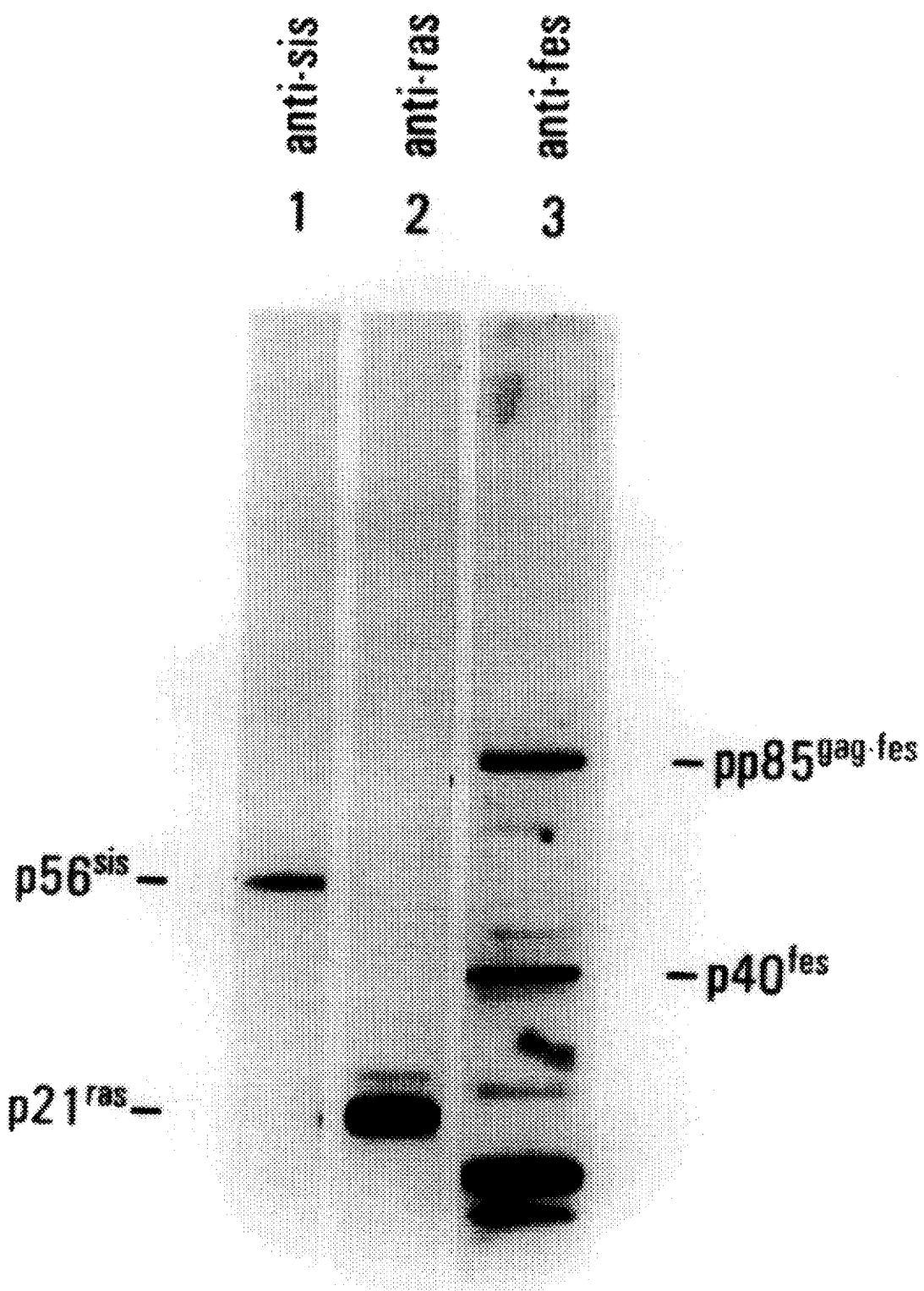

FIG. 14 is a photograph of an autoradiograph illustrating an immunological assay for the presence of ras-, sis- or fes-related proteins in a cell extract using a Western blot procedure. The lanes of the Figure each contained an extract from about 10$^6$ cells per lane of mink lung cells transformed with the Snyder-Thielen strain of feline sarcoma virus (MSTF cells).

The extracts were assayed using antisera raised to polypeptides corresponding to residues 96–118 of p21$^{ras}$ (polypeptide 142, lane 2) to residues 1–18 of PDGF-2 (polypeptide 112, lane 1) And to residues 744–759 of v-fes (polypeptide 127, lane 3). Proteins were visualized as described for FIG. 6.

FIG. 15 is a photograph of an autoradiograph illustrating an immunological assay for the presence of a variety of proteins encoded by or related to sis, fes and ras oncogenes in urine using a Western blot procedure similar to that described hereinbefore. The liquid body sample in this assay was urine concentrate, obtained as described in the Materials and Methods section. The concentrated urine was electrophoresed into 5–17% polyacrylamidize gel and then electrophoresed onto nitrocellulose.

Urine from 8 donors was concentrated 40-fold, dialyzed and 25 microliters (the equivalent of 1 ml of unconcentrated urine) was electrophoresed and the proteins therein transferred to nitrocellulose as described before. These donors had multiple myeloma (lane 1, FIGS. 15 and FIG. 15B), gastric cancer (lane 2, FIG. 15A and FIG. 15B; lane 1, FIG. 15C and FIG. 15D), 35 weeks pregnant (lane 3, FIG. 15A and FIG. 15B), lymphoma (lane 4, FIG. 15A and FIG. 15B), gastric cancer (lane 1, FIG. 15C and FIG. 15D), 36 weeks pregnant (lane 2, FIG. 15C and FIG. 15D), breast cancer (lane 3, FIGS. 15C and FIG. 15D) , 39 weeks pregnant (lane 4, FIG. 15C and FIG. 15D) and breast cancer (FIG. 15E).

Monoclonal or oligoclonal receptor-containing Antisera induced by sis- (FIG. 15A and FIG. 15B), ras- (FIG. 15C and FIG. 15D) or fes-related polypeptides (FIG. 15E) were used to probe each sample to assay for immunizing polypeptides. Twenty microliters of ascites fluid (induced by hybridoma ATCC HB 8679 and described hereinafter, and induced by a hybridoma raised to the sis related polypeptide 112 corresponding in sequence to positions 1–18 of PDGF-2; FIGS.

15C and 15D, and 15A and 15B, respectively) or mouse plasma (raised to a polypeptide corresponding in sequence to positions 744–759 of the fes oncoprotein; FIG. 15E) were preincubated for 30 minutes at 37 degrees C. with 100 micrograms of the immunizing ras polypeptide 142 (FIGS. 15A, 15D of FIG. 15E), sis polypeptide 112 (FIGS. 15B and 15C) or fes polypeptide (FIG. 15E, lane 3), with polypeptide 171 corresponding to positions 366–381 encoded by erb B (FIG. 15E, lane 3), or with polypeptide 312 corresponding to positions 590–605 of abl (FIG. 15E lane 4).

Following preincubation, the samples were diluted 1 to 1000 in 3 percent BSA, 0.1 percent Triton® X-100 in PBS at a pH value of 7.4. The antisera were then assayed as described hereinabove. Binding was visualized as described in FIG. 6.

FIG. 16 is a photograph of an autoradiograph illustrating an immunological assay for the presence of ras-, sis-, and fes-related proteins in urine.

Urine was collected at monthly intervals from a donor previously diagnosed as having active breast cancer (lanes 1, 4, 7, 2, 5, 8, 3, 6, 9, FIG. 16A). Urine was concentrated and dialyzed and an equivalent of 1 ml unconcentrated urine was applied to each lane of FIG. 16A.

In FIG. 16B, aliquots of the same sample used in Panel A, lanes 3, 6 or 9 were applied at the following equivalents of unconcentrated urine; 1000 microliters (lane 1); 500 microliters (lane 2); 250 microliters (lane 3); 125 microliters (lane 4); 60 microliters (lane 5); 30 microliters (lane 6); 15 microliters (lane 7); 7.5 microliters (lane 8).

The samples were prepared and probed with oligoclonal antisera to ras-(positions 96–118, polypeptide 142; FIG. 16A, lane 1–3; FIG. 16B), fes-(positions 744–759, polypeptide 127; FIG. 16A, lanes 4–6) or sis-polypeptide (PDGF-2 positions 1–18, polypeptide 112; FIG. 16A, lanes 7–9) as described for FIG. 15 except that no preincubation With synthetic peptides was performed.

FIG. 17 is a photograph of an autoradiograph illustrating an immunological assay for the presence of ras- And fes-related proteins in urine. The donors of the assayed urine samples had been diagnosed as having recurrent breast cancer (lanes 1, 2) or were normal individuals (lanes 3–8).

The assay for ras-related proteins (FIG. 17A) and fes-related proteins (FIG. 17B) was conducted as described for FIG. 16. The samples assayed were urine from a patient in clinical remission from breast cancer (lane 1), the same patient 3 months later when the breast cancer reappeared (lane 2), and normal female (lanes 3–5), wherein samples were collected 3 days apart, a normal female where samples were collected 12 hours apart (lanes 6–7) and a normal male (lane 8).

FIG. 18 is a photograph of an autoradiograph showing the detection of ras-, fes- and sis-related proteins in urine samples from donors having cancer. Urine from donors with bladder cancer (lane 1), prostate cancer (lane 2), prostate nodule (lane 3), or lymphoma (lane 4) were prepared and probed with antisera to sis (FIG. 18A), ras (FIG. 18B) or fes (FIG. 18C) as described in FIG. 16. The bands migrating slightly slower than p56$^s$ is in lanes 1,2 represents excessive amounts of albumin in these samples. Although the increased levels of p56$^{sis}$, p31$^{sis}$, and p25$^{sis}$, correlate with the increased albumin levels in FIG. 18A, lanes 1,2, other urine, samples from donors with bladder or prostate cancer contained increased levels of sis-related proteins in the absence of elevated albumin levels (data not shown). The slowest migrating bands in FIG. 18B, lanes 1–3 identify p100$^{ras}$ while the bands slightly faster than light chain in FIG. 18B lanes 1–4 identify p21$^{ras}$.

FIG. 19 is a photograph of an autoradiograph illustrating the detection of oncogene-related proteins in urine from a pregnant donor.

Figure 19A:
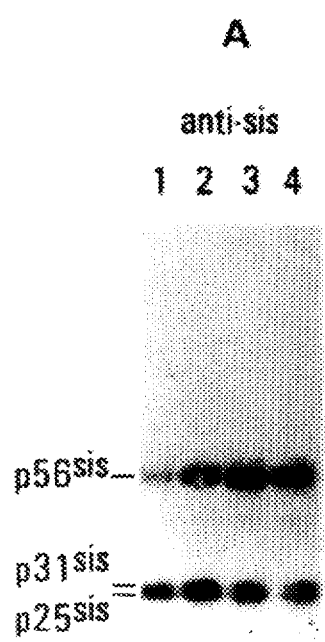
Figure 19B:
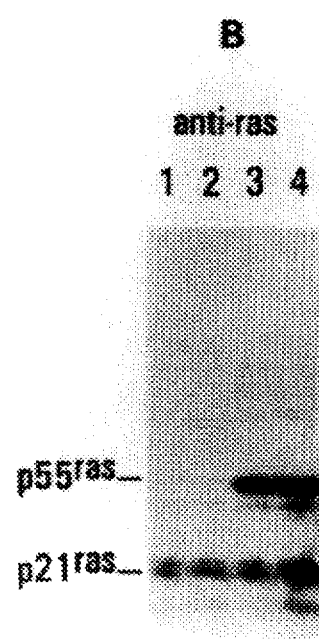
Figure 19C:
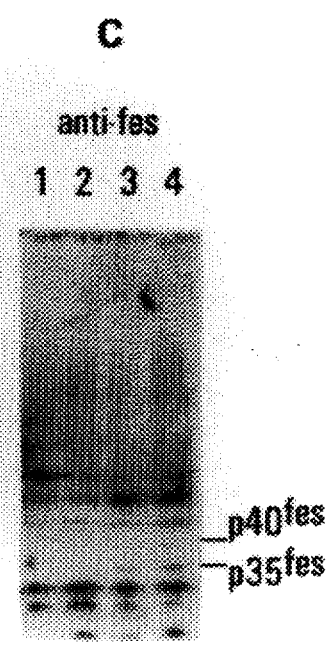

Four urine samples from the same individual collected at one week intervals during the final month of pregnancy were probed with antisera to sis-related polypeptide 112 (PDGF-2 position 1–18; FIG. 19A), ras polypeptide 142 (positions 96–118; FIG. 19B), or fes polypeptide 127 (positions 744–759; FIG. 19C). Overexposure of FIG. 19C demonstrates the presence of p35$^{fes}$ lanes 3 and 4) and p40$^{fes}$ (lane 4). The protein migrating slightly faster than the light chain band (FIG. 19C, lanes 1–4) or at the bottom of the gel (FIG. 19C, lanes 2–4) was detected with the mouse antisera to the fes peptide. In addition, a protein of 150,000 daltons was also detected with the mouse antisera to the fes peptide. Urine samples were collected at one week intervals.

FIGS. 20, 21, and 22 are tables showing amino acid sequences of three conserved regions of oncoproteins that have protein kinase activity. Those regions are denominated as "CONSERVED KINASE REGION" 1, 2 and 3, respectively, in FIGS. 20, 21 and 22. The oncogene encoding an oncoprotein having protein kinase activity is designated by its usual symbol in the left-hand column. The middle column identifies the location in the oncoprotein polypeptide sequence, from the amino-terminus, of the conserved amino acid residue sequence. The right-hand column shows the amino-acid residue sequences, from left to right and in the direction from amino-terminus to carboxy terminus, of those conserved regions. The amino acid residue sequences are also the sequence of polypeptides useful as immunogens for inducing production of the monoclonal receptors of this invention.

FIG. 23 is a table showing the frequency of detection of oncogene-related proteins in urine samples of 51 control (normal donors) and 189 urine samples from donors with a variety of malignancies. The amount of oncogene-related proteins in the urine was estimated using immunoblots, and placed into one of four categories: undetectable, detectable, 5- to 15-fold elevated and greater than 15-fold elevated. The remaining types are listed as composite.

p21$^{ras}$ was detected in approximately 70 percent of all samples from donors having neoplastic tumor disease. However, similar frequencies were found in apparently normal individuals. The most striking elevation of p21$^{ras}$ was detected in samples from donors having ovarian and gastric cancer as well as myeloma and molar pregnancies, all of which had greater than 15-fold elevations of this protein in at least 30 percent of the samples.

FIG. 24 is a table of data reflecting the detection of various levels of the oncogene-related proteins in 260 urine samples from pregnant donors. The samples were grouped according to the trimester of pregnancy. Multiple urine collections were obtained from many of the donors. Assays were performed in accordance with the procedures and methods set from hereinafter in the Materials and Methods section. As with the subset of donors having breast cancer, discussed hereinafter, very high levels of p55$^{ras}$ were detected in a group of pregnant donors throughout the course of pregnancy. sis- and fes-related proteins increased as the pregnancy proceeded.

The levels of p55$^{ras}$ changed dramatically in the course of several of the pregnancies. In contrast, levels of p55$^{ras}$ detected in multiple samples from normal or breast cancer donors, the concentration of ras-related proteins increased greater than 15-fold in one week in certain donors.

The concentration of the three sis-related proteins was approximately the same throughout the last month of pregnancy. p35$^{ras}$ was detected in the final two weeks of pregnancy while p40$^{ras}$ was detected only in the final week.

Urine samples taken six weeks postpartum continued to contain elevated concentrations of these sis-related proteins although the ras- and fes-related proteins returned to normal (data not shown).

Figure 25:
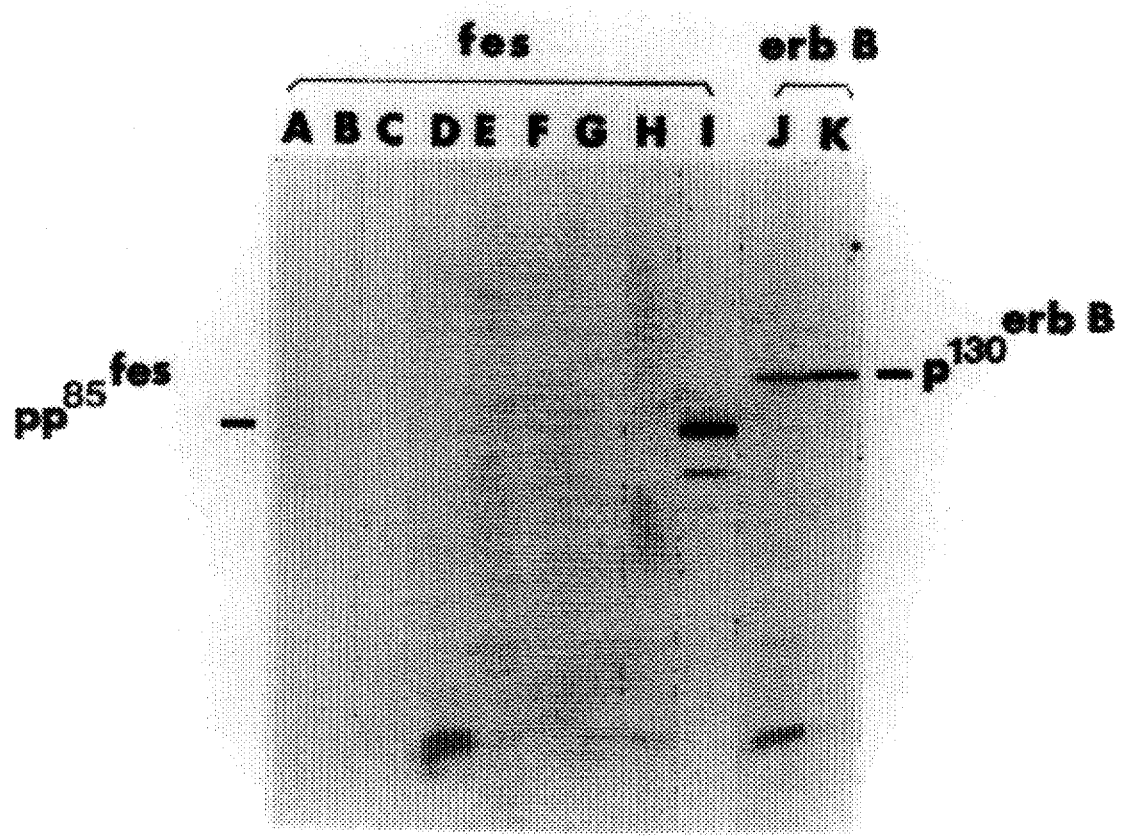

FIG. 25 shows an immunoblot of mink lung cells transformed by fes. A mink cell extract was probed with various antibodies to fes (lanes A–I) or erb B (lanes J,K).

Figure 26:
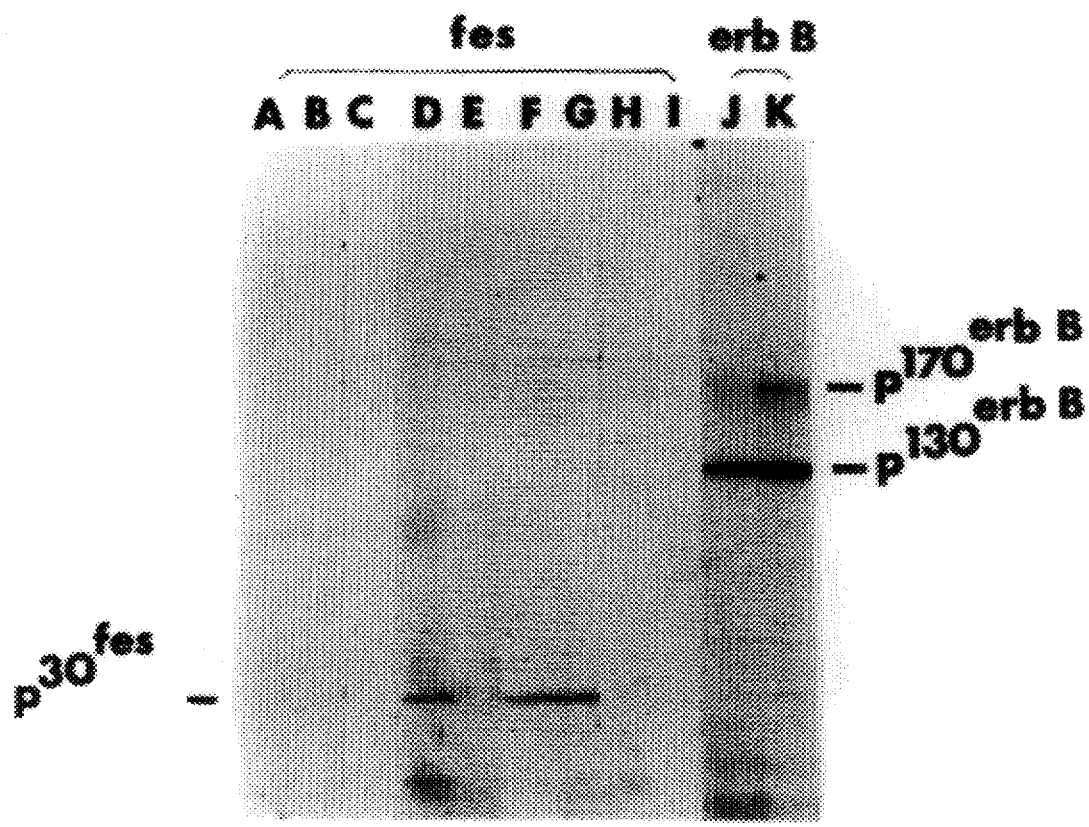

FIG. 26 shows an immunoblot of human epidermoid carcinoma cells. An extract of a human epidermoid carcinomal cell line was probed with antibodies as used in FIG. 1.

Figure 27:
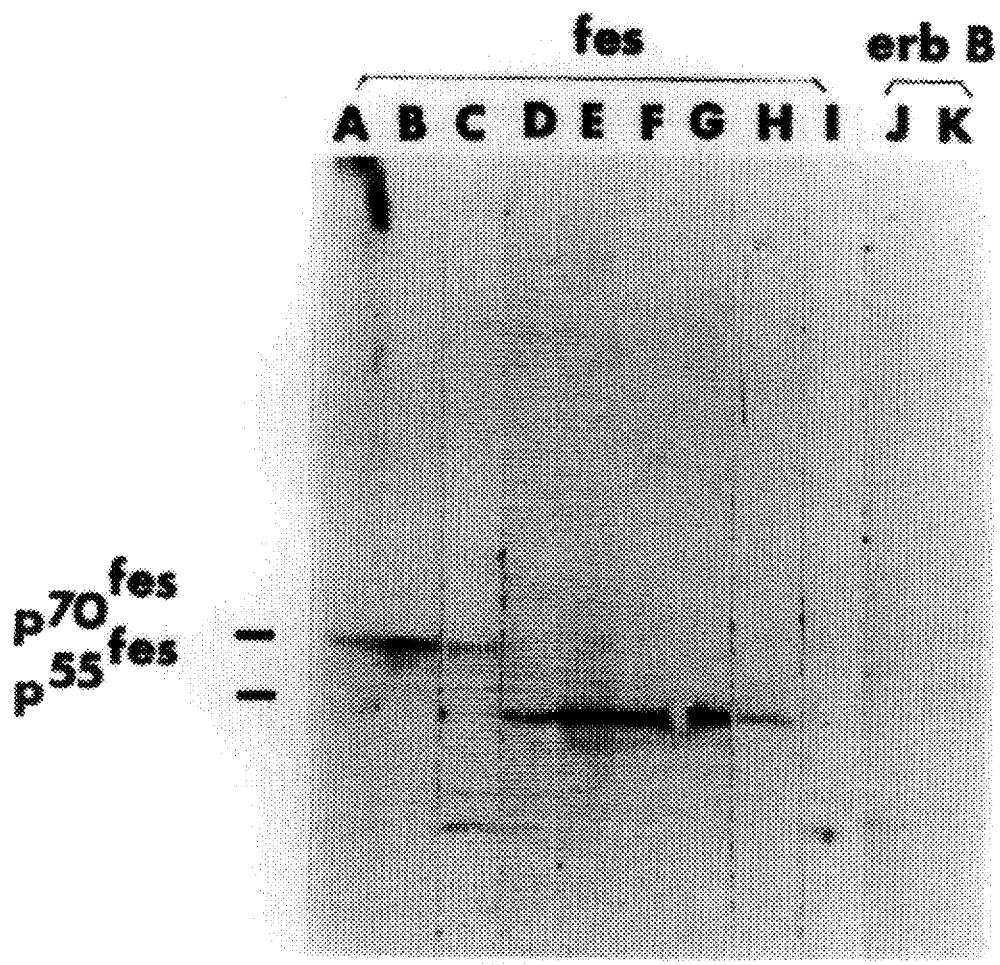

FIG. 27 shows an immunoblot of a concentrated urine sample from a pregnant diabetic patient. A concentrated urine sample from a pregnant diabetic patient was probed with antibodies used in FIG. 1.

Figure 28:
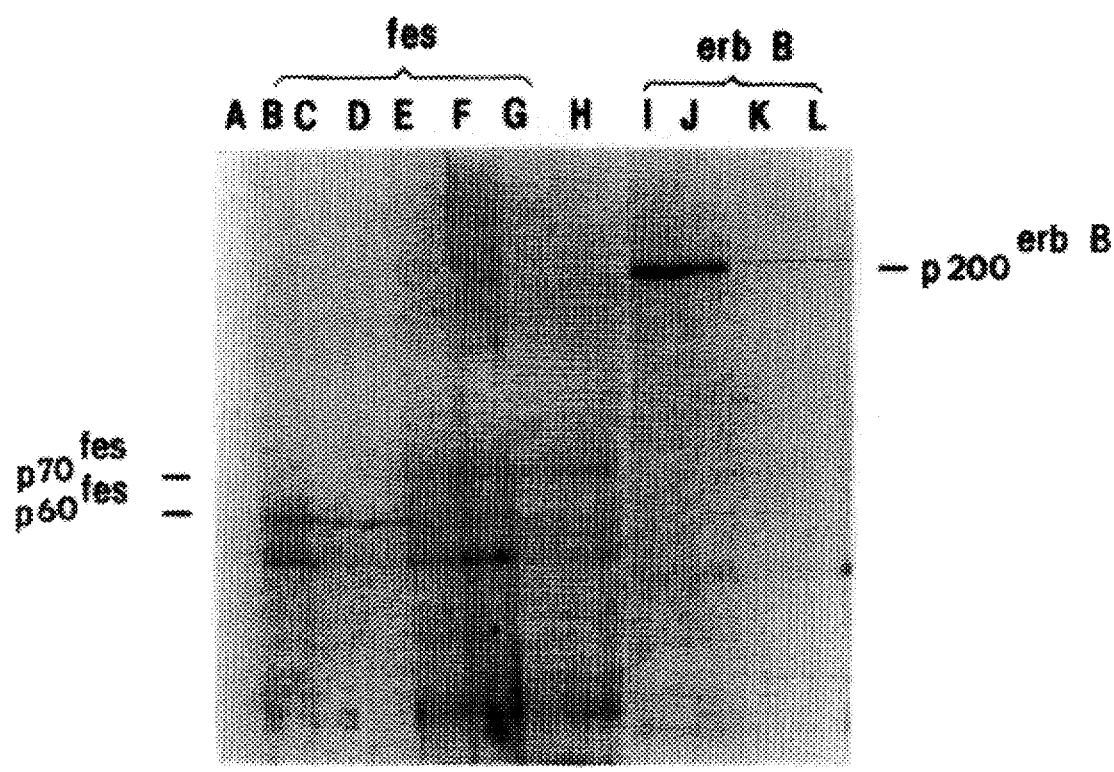

FIG. 28 shows an immunoblot of an endometrial tumor extract. An extract of an endometrial tumor, (NIH Accession No. 071-781473-1), was probed with antibodies to fes (lanes A–H) or erb B (lanes I–L). Antibodies in lanes A–D give reactivity patterns in ELISA assays different from those of lanes E–H. Lanes I and J are directed against domains of v-erb B, and lanes K and L produce a different reactivity pattern against the same oncoprotein.

Figure 29:
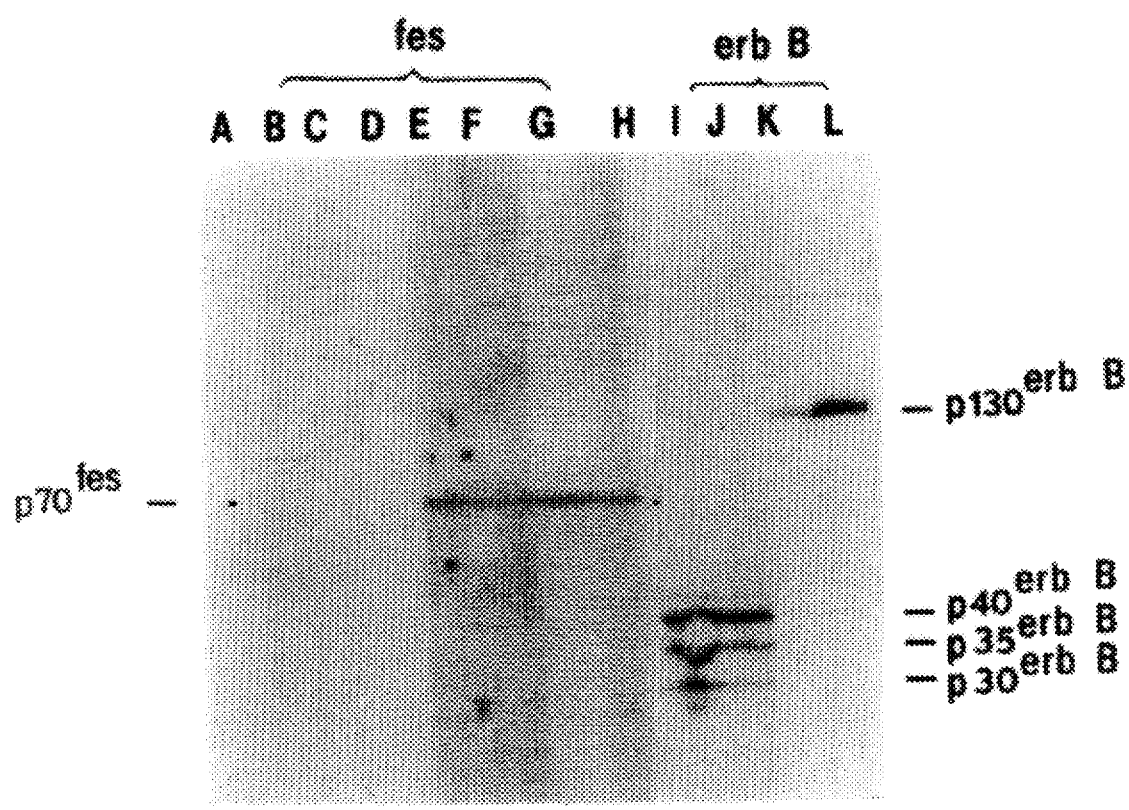

FIG. 29 shows an immunoblot of a breast tumor extract. An extract of breast tumor (NIH Accession No. 121-960-1), which metastasized to the lymph node was probed with antibodies used in FIG. 4.

Figure 30:
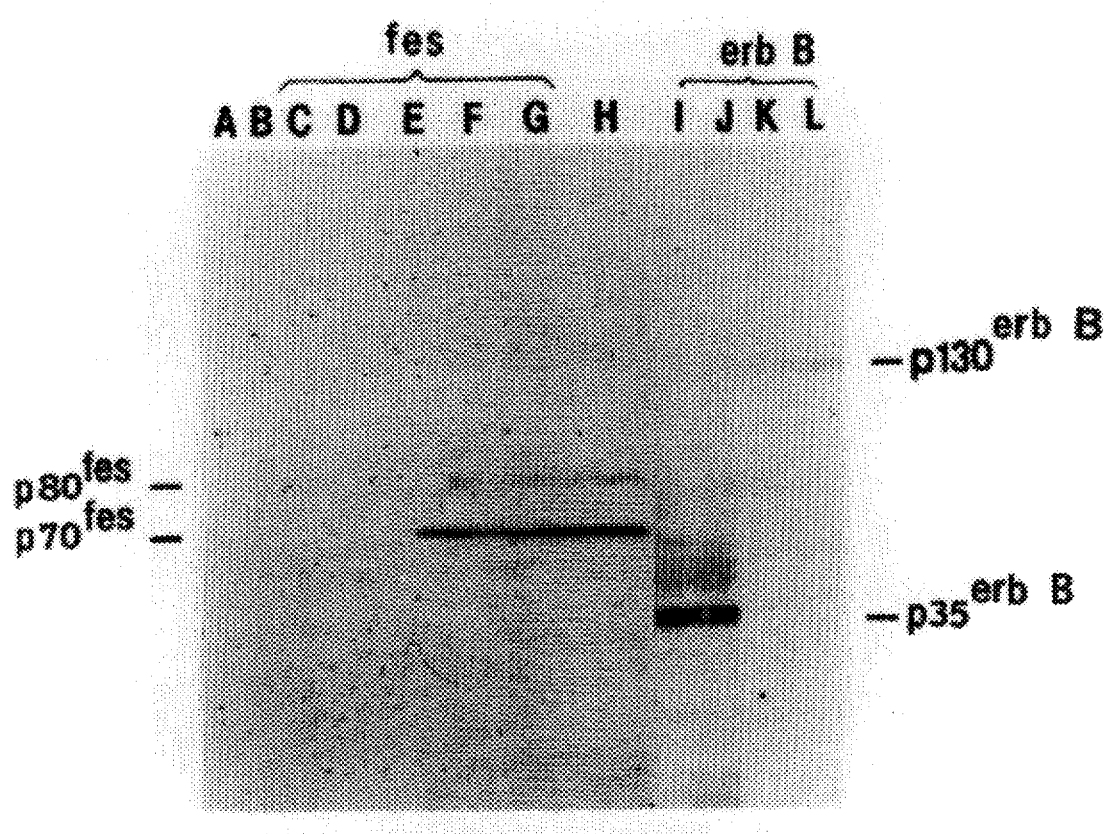

FIG. 30 shows an immunoblot of breast tumor, (NIH Accession No. 31-14459), an extract of which was probed with the antibodies used in FIG. 4.

Figure 31:
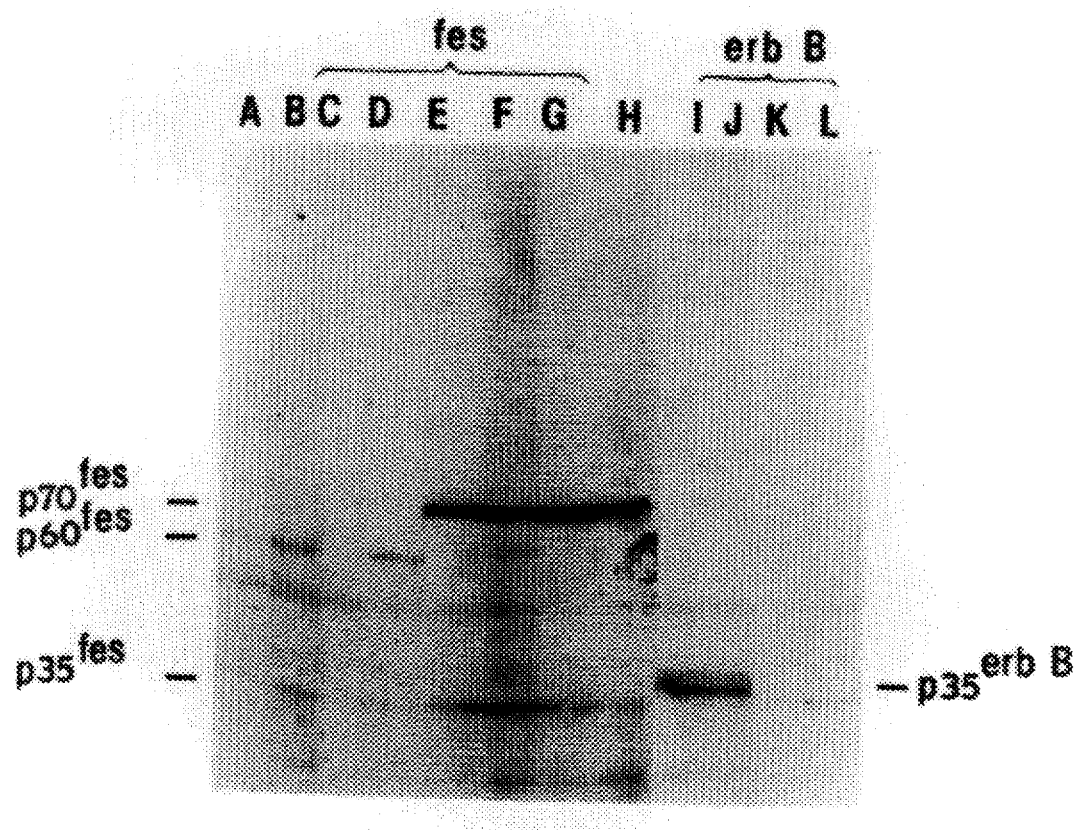

FIG. 31 shows an immunoblot of ovarian tumor, (NIH Accession No. 31-13530), an extract of which was probed with the antibodies used in FIG. 4.

Figure 32:

FIG. 32 shows an immunoblot of a breast tumor, (NIH Accession No. 121-960-1), which metastasized to a lymph node. This metastic breast tumor extract was probed with antibodies to ros (lane A), fes (lane B), βTGF, (lanes C–G), ras (lanes H–J), and erb B (lanes K–N).

Figure 33:
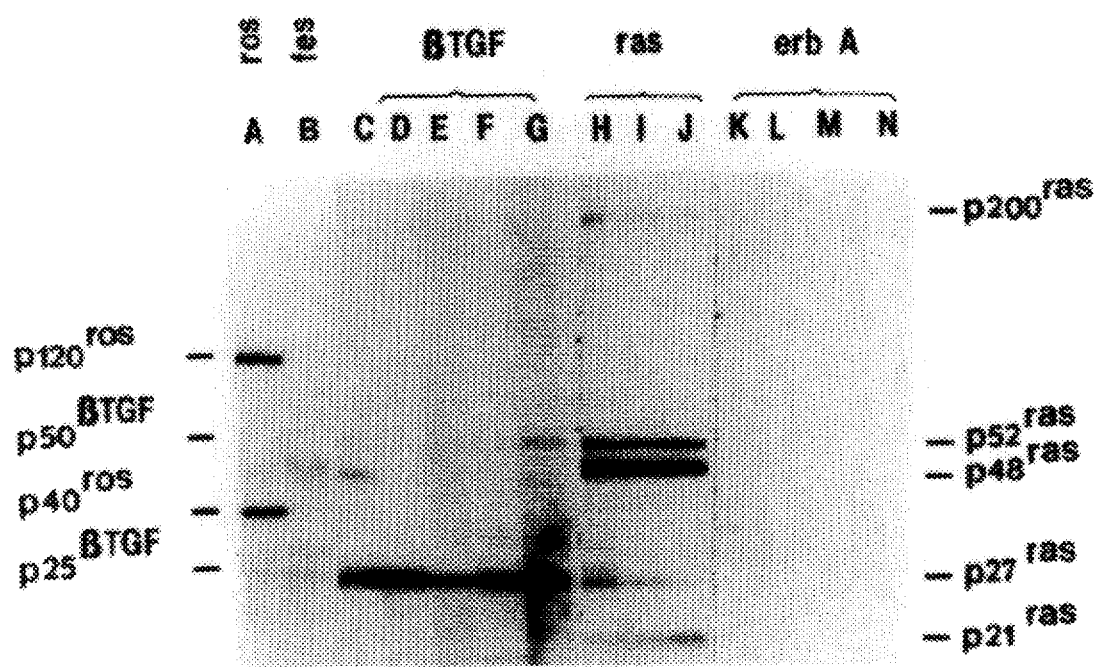

FIG. 33 shows an immunoblot of a metastatic ovarian carcinoma extract derived from NIH tumor 31-18265. This carcinoma metastasized to the omentum and was probed with the antibodies used in FIG. 8.

Figure 34:
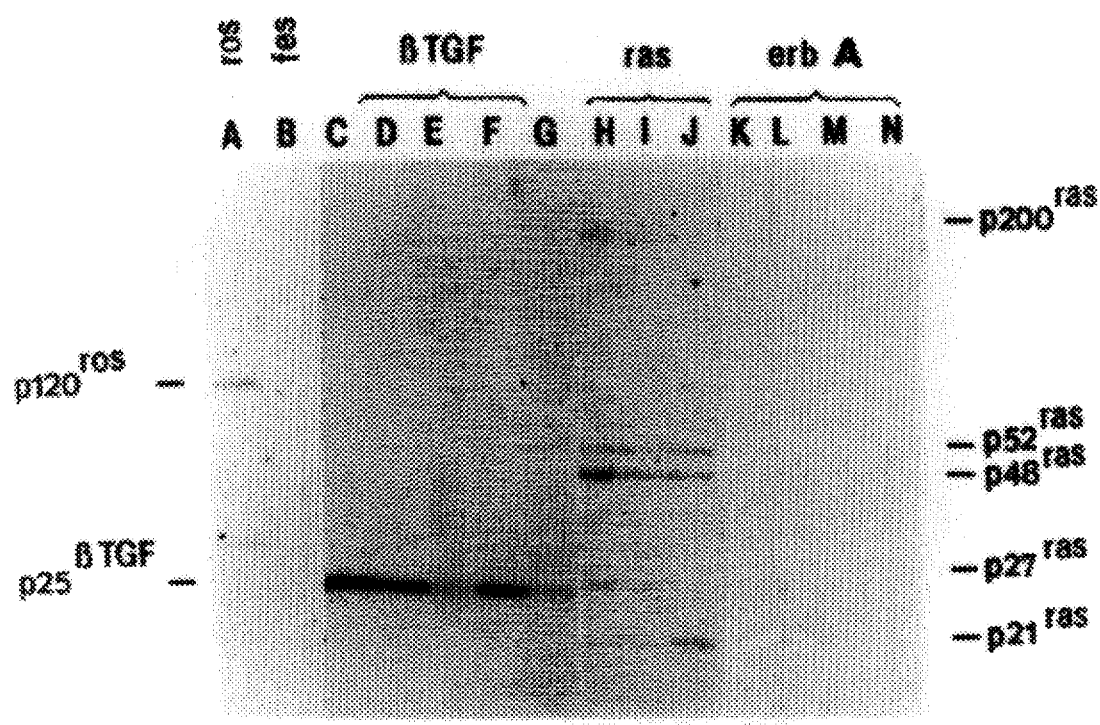

FIG. 34 shows an immunoblot of a metastatic colon carcinoma (NIH Accession No. 31-18152) which metastasized to the lymph node. This extract was probed with the antibodies used in FIG. 8.

Figure 35:
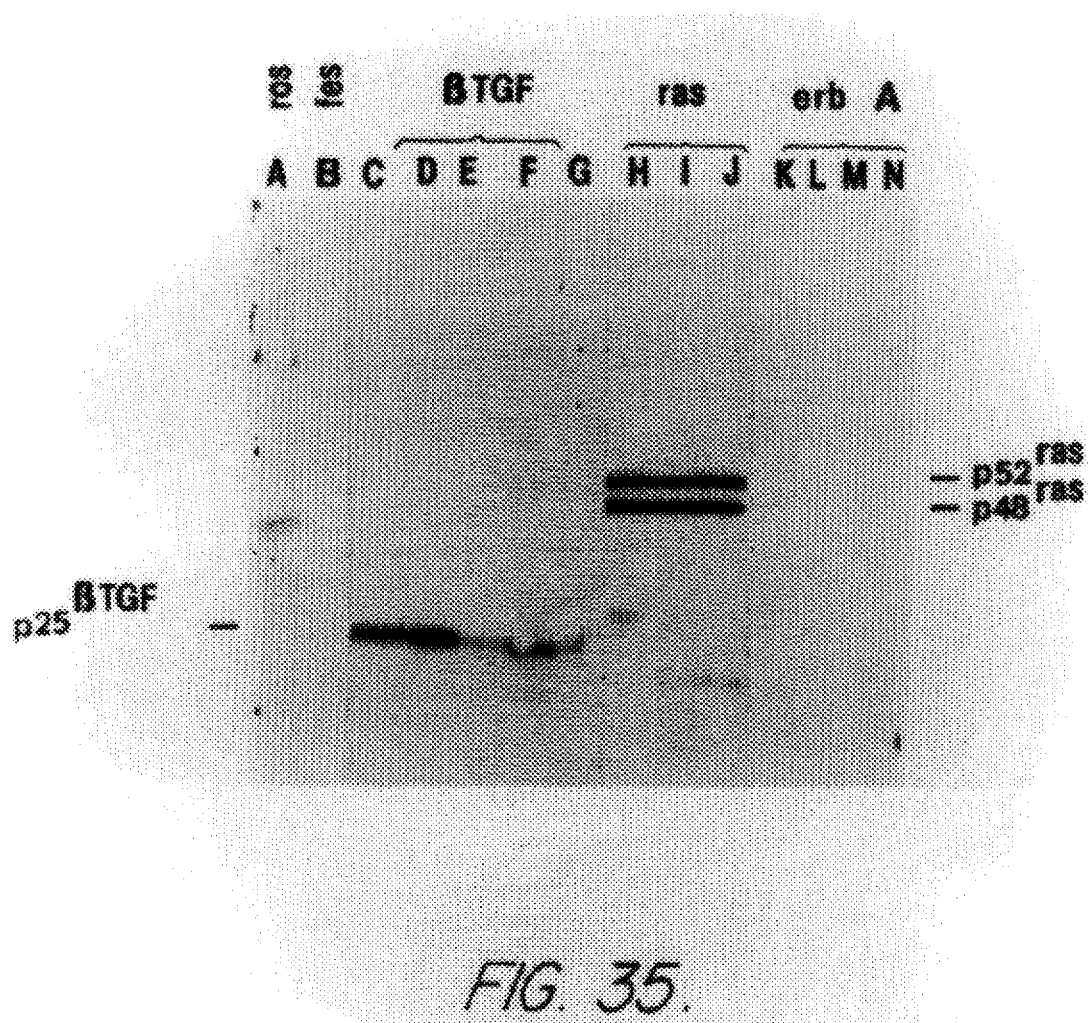

FIG. 35 shows an immunoblot of a metastatic ovarian carcinoma (NIH Accession No. 031-10128-1). This extract of an ovarian carcinoma which metastasized to the omentum was probed with the antibodies used in FIG. 8.

Figure 36:
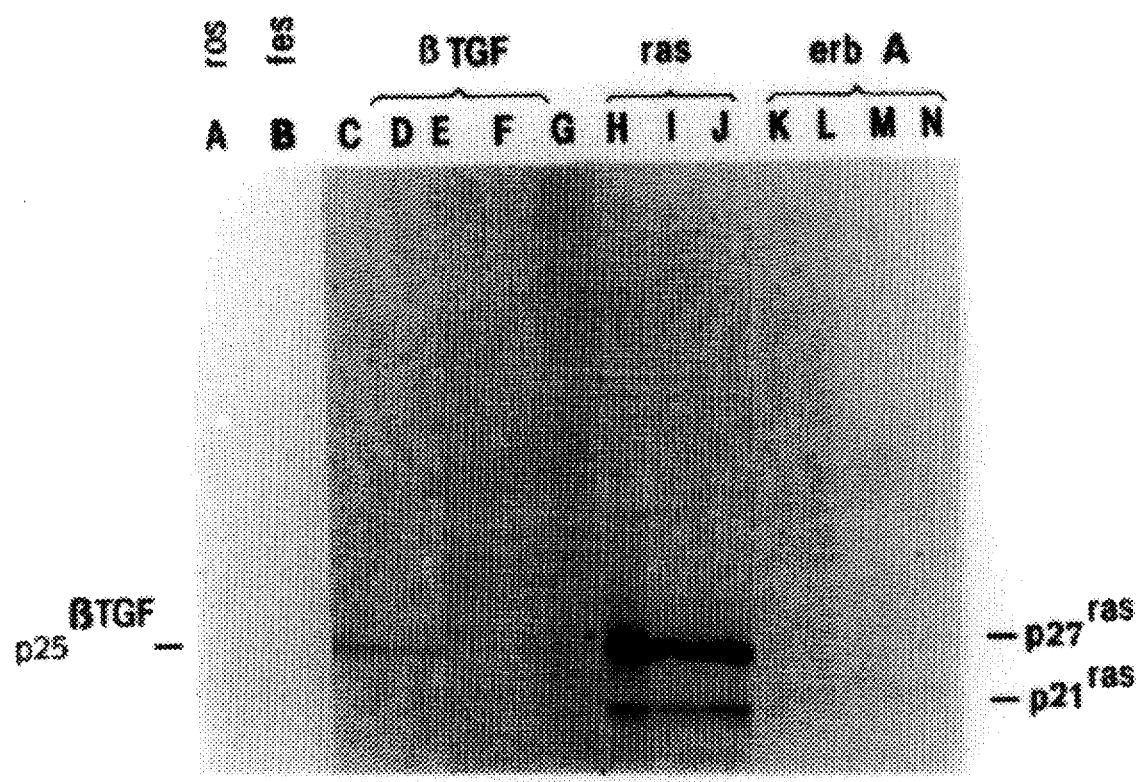

FIG. 36 shows an immunoblot of a lymphoma (NIH Accession No. 021-50073-1) from the spleen. This extract was probed with the antibodies used in FIG. 8.

Figure 37:
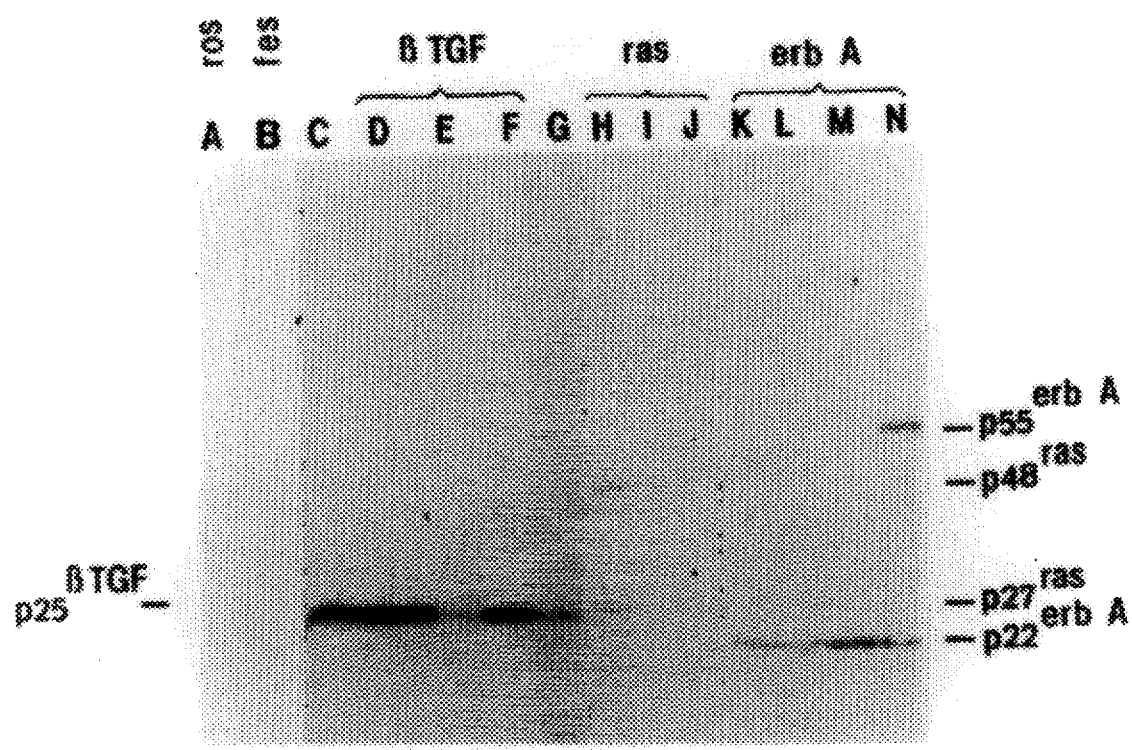

FIG. 37 shows an immunoblot of a breast carcinoma extract (NIH Accession No. 031-1239-1). This extract was probed with the antibodies used in FIG. 8.

Figure 38:
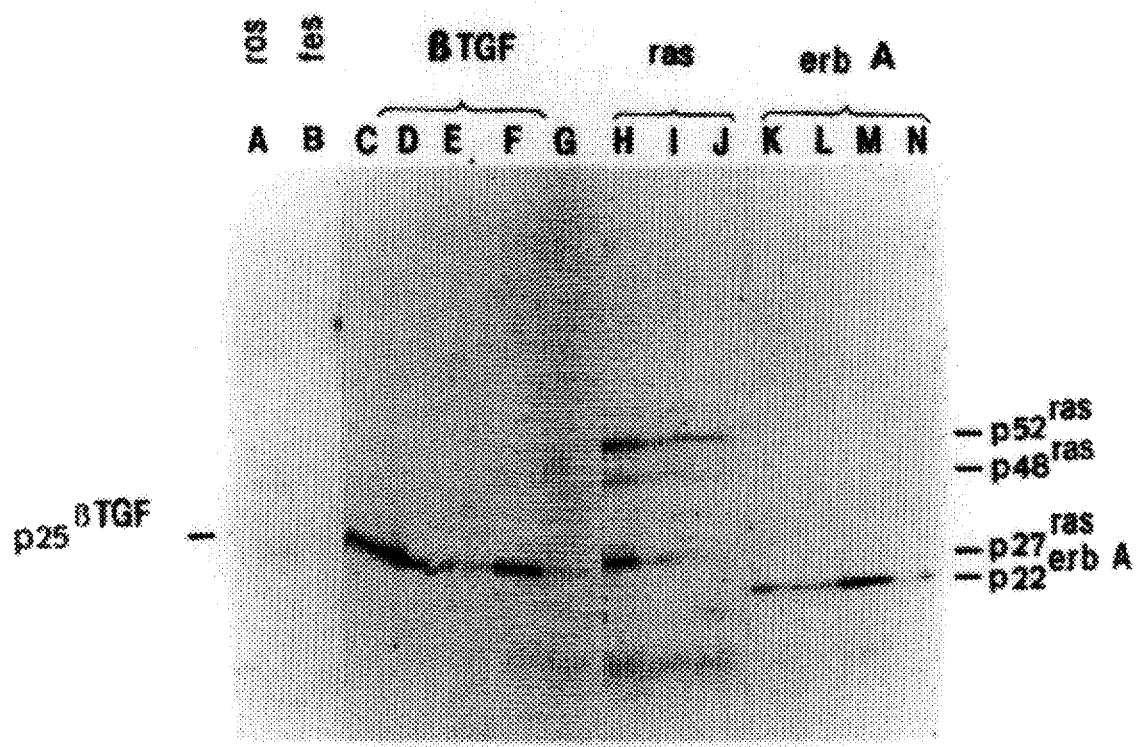

FIG. 38 shows an immunoblot of a rectal tumor extract (NIH Accession No. 31-19066). This extract was probed with the antibodies used in FIG. 8.

Figure 39:
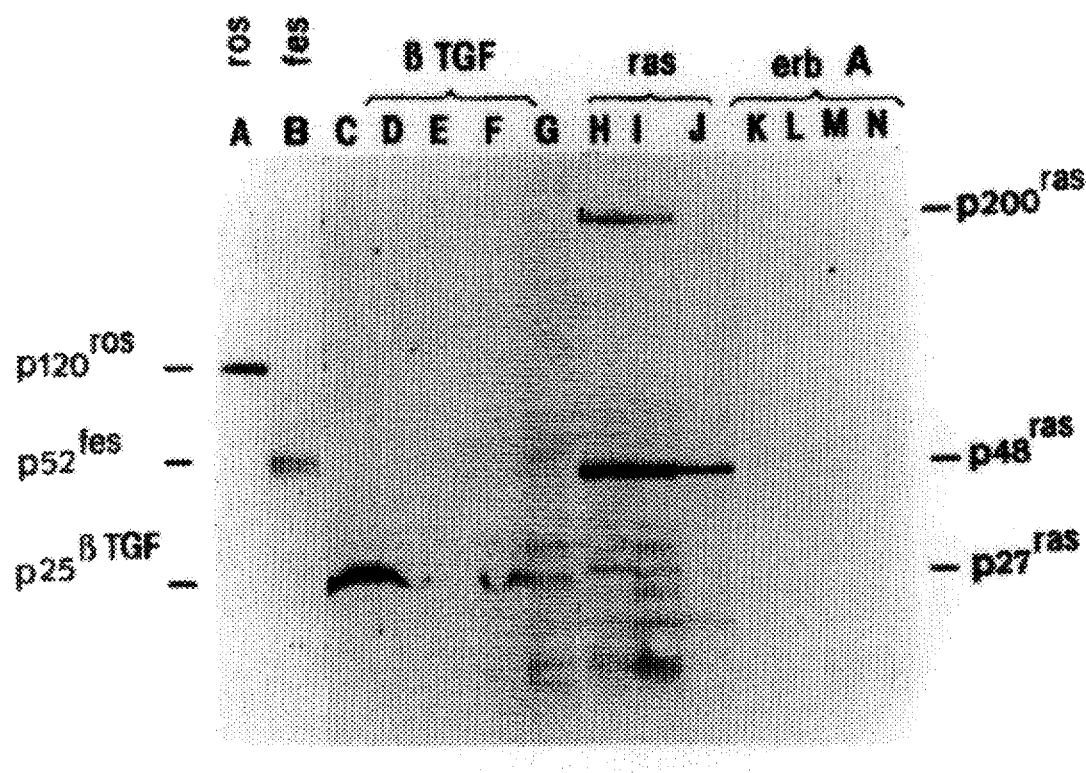

FIG. 39 shows an immunoblot of a metastic lung carcinoma, (NIH Accession No. 041-78297-1). An extract of this lung carcinoma which metastasized to a lymph node was probed with the antibodies used in FIG. 8.

Figure 40:
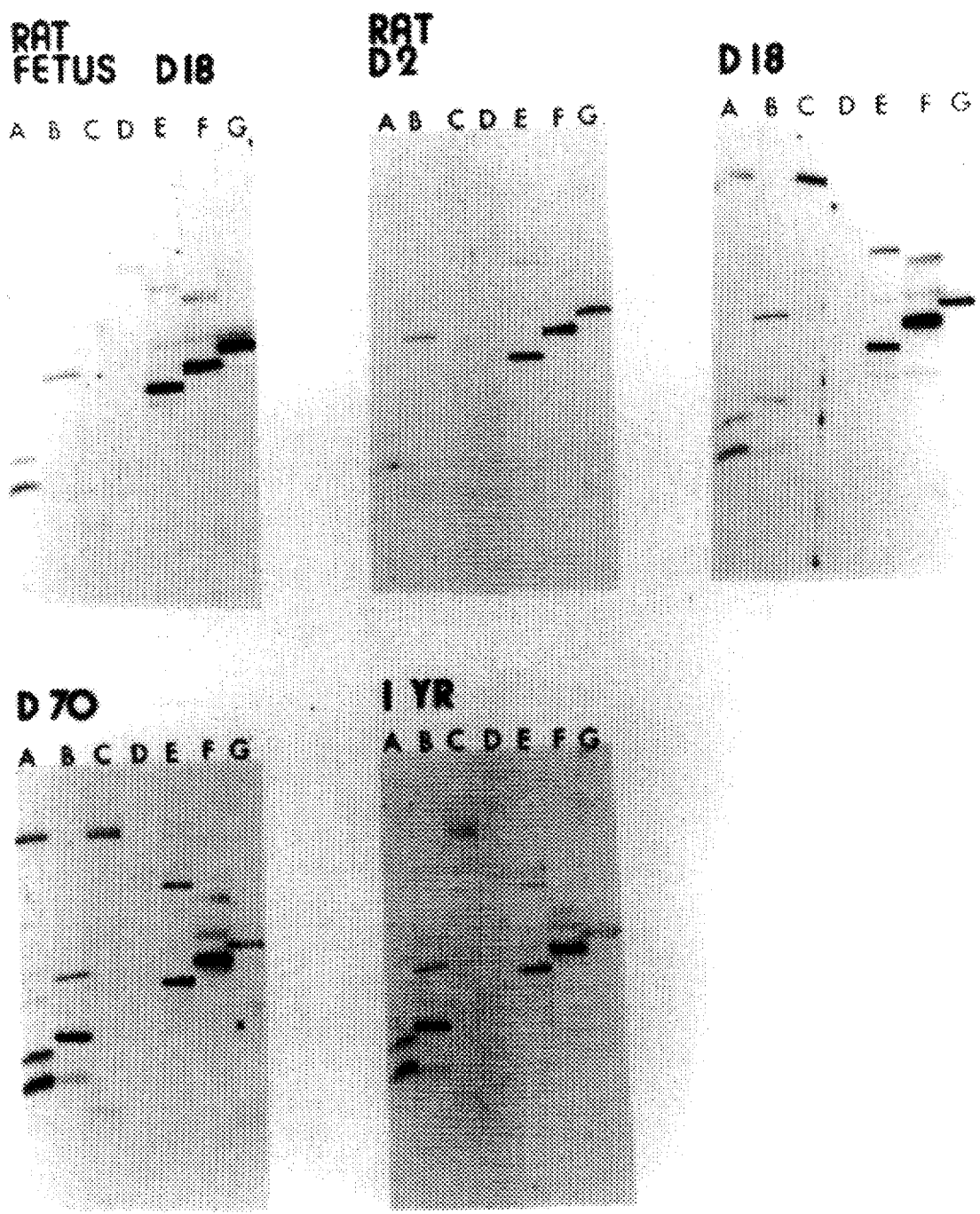

FIG. 40 shows an immunoblot of rat striatum. An extract of rat striatum taken from 18 day old embryo, and 2 day old, 18 day old, 70 day old, and 1 year old rats were probed with H/N-RAS (lane A), H-RAS (lane B), MYC (lane C), v-myb (lane D), int-1 (lane E), and two different SIS directed antibodies (lanes F and G).

Figure 41B:
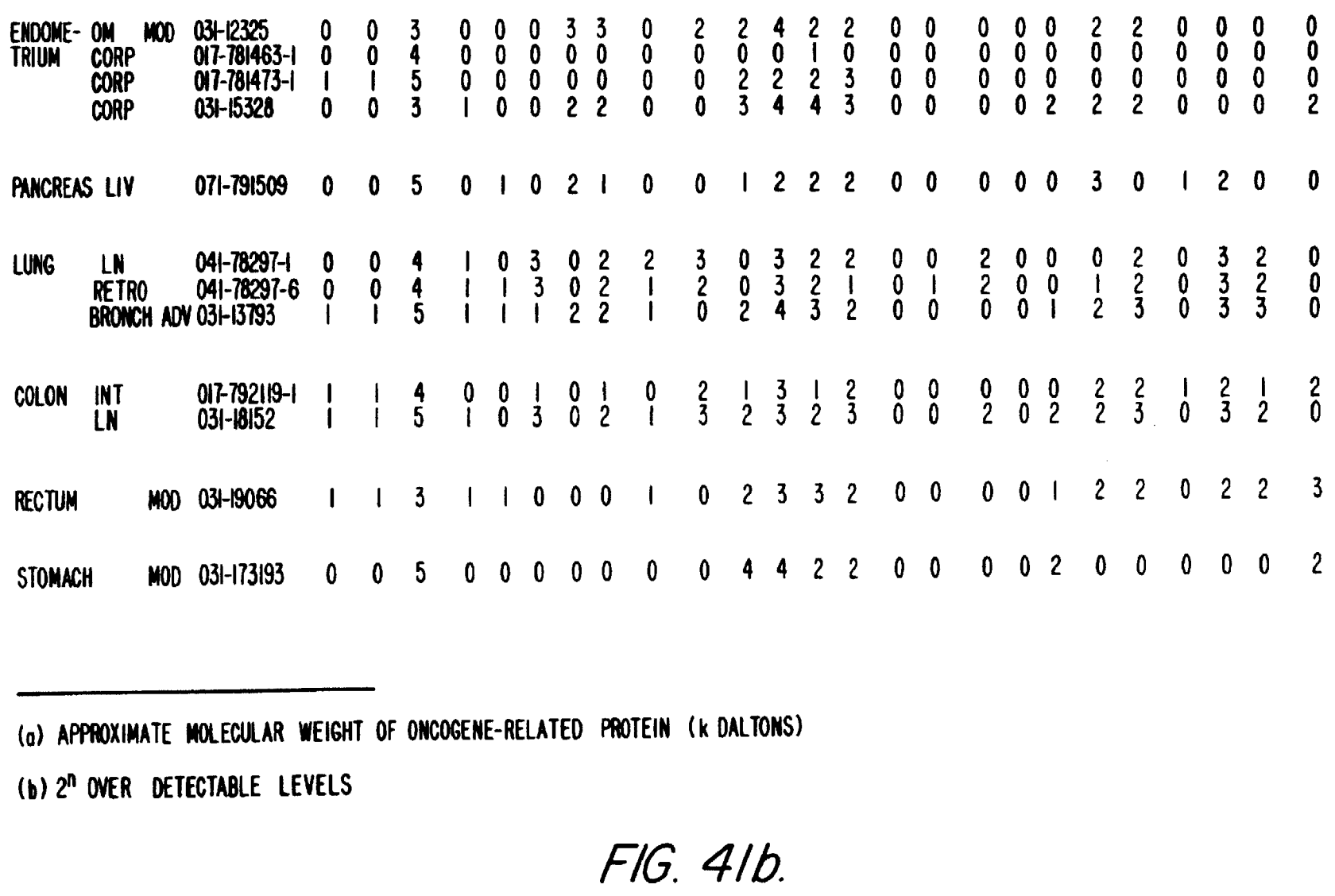

FIGS. 41 and 42 are tables showing reactivity patterns of tumor extracts derived from cell lines on deposit at the NIH depository. The extracts were probed with various antibodies, and the resultant patterns were scored for the presence and level of oncogene product. The scoring was based on band intensities derived using the immunoblot technique.

Figure 43:
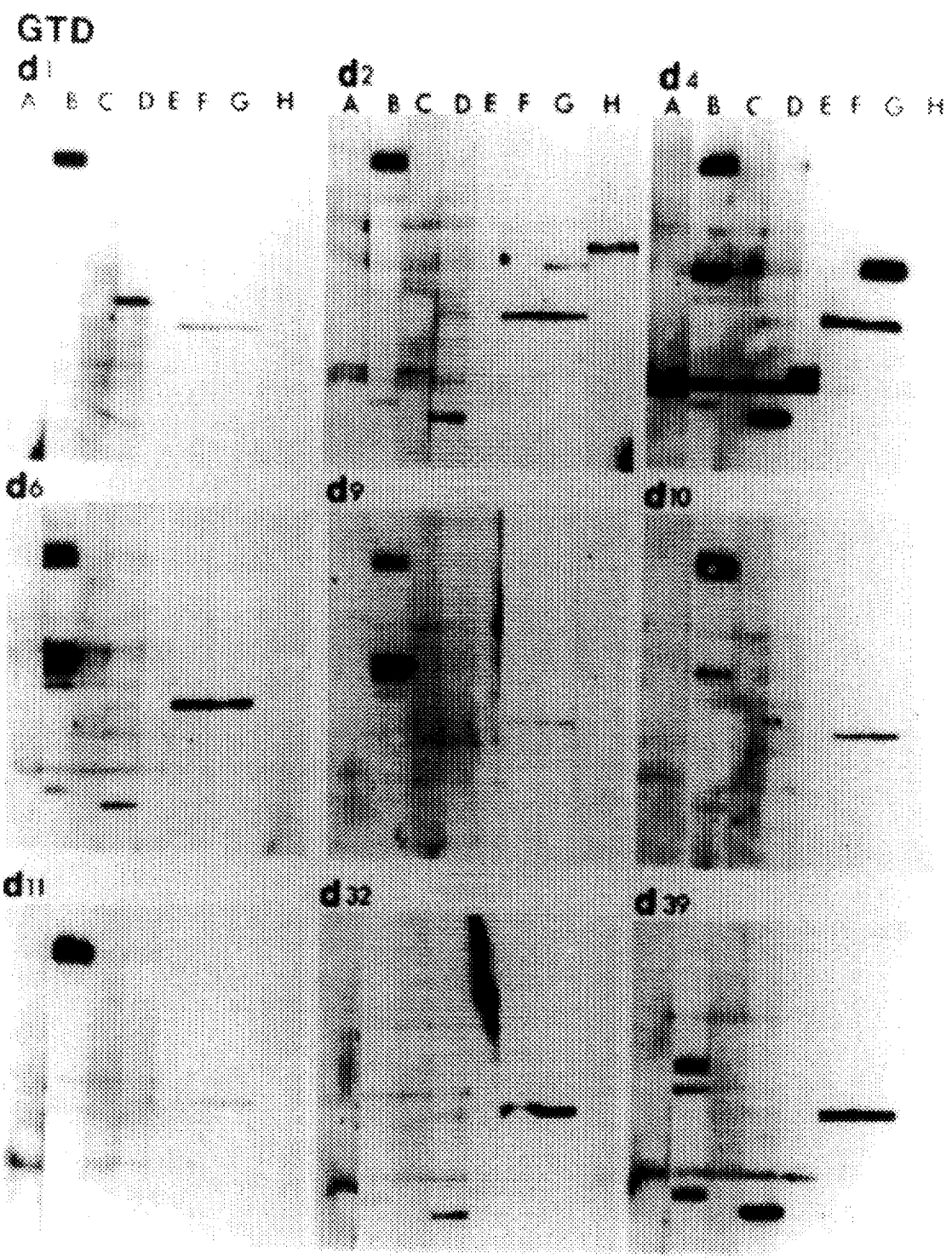

FIG. 43 shows the asynchronous appearance of oncogene-related protein in the urine of a gestational trophoblast disease patient undergoing chemotherapy. Sequential urine samples from a gestational trophoblast disease patient undergoing chemotherapy were probed with antibodies directed against SIS residues (lane A) H/N-RAS residues (lane C), MYC residues (lanes D and E), src residues (lane F and G), and int-1 residues (lane H).

Figure 44A:
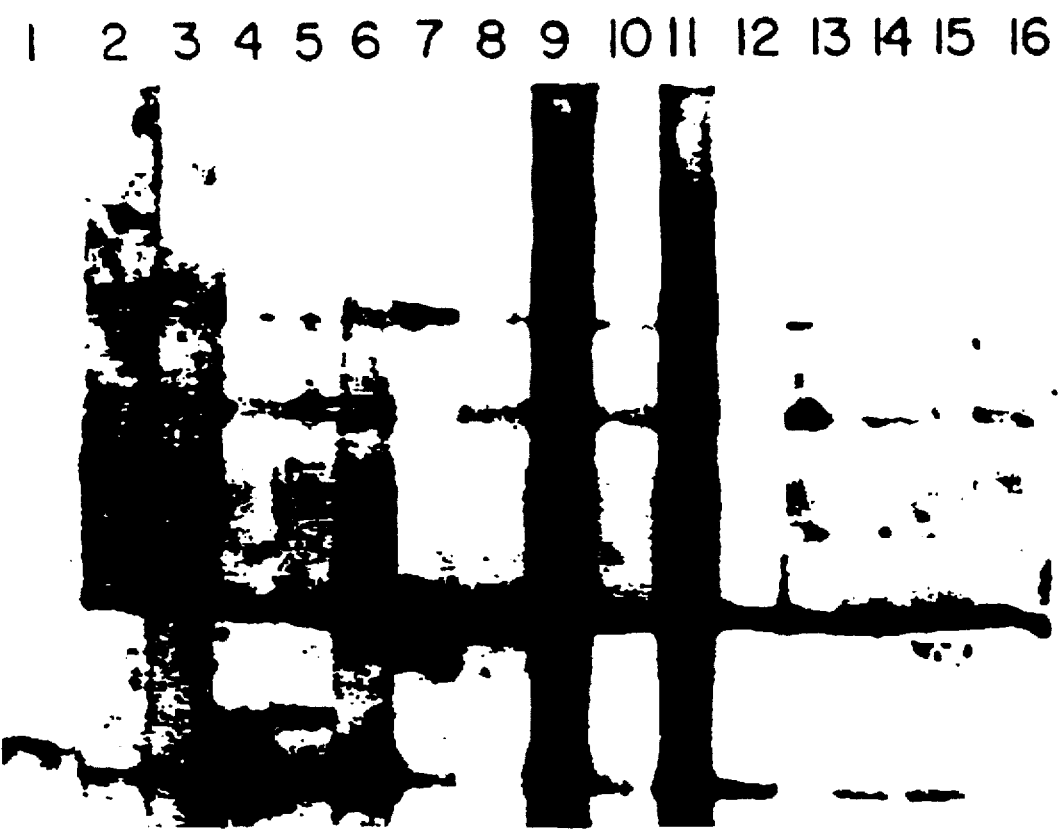

FIG. 44(A). Immunoblot of serum of normal, healthy control. The sample of 100 μl of serum was probed with antibodies to peptide sequences predicted by the following oncogenes: sis (lane 1), fes (lanes 2, 3 and 15), β-TGF (lanes 4 and 5), int-1 (lanes 6 and 12), myb (lane 7), src (lane 8), c myC (lanes 9, 13 and 14), mos (lane 10), and H-ras (lanes 11 and 16).

Figure 44B:

FIG. 44(B). Immunoblot of serum of individual with multiple carcinogen exposure (PCB's, asbestos, cigarette smoke) but without clinically detectable malignant disease. The sample of 100 μl of serum was probed with antibodies to peptide sequences predicted by oncogenes as defined in FIG. 1(A). Note the presence of prominent lower bands in lanes 11 and 16 not found in the normal, healthy control; these bands correspond to the Harvey ras oncogene-encoded P21 protein.

Figure 45:
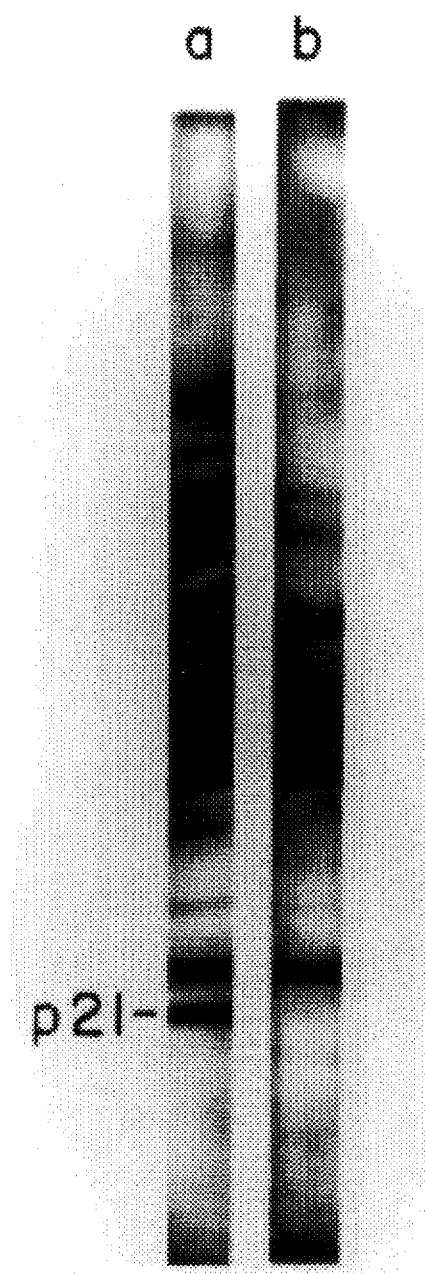

FIG. 45. Immunoblot of serum of patient with multiple exposures to carcinogens, (a) 18 months prior to clinical manifestation of the colonic polyp, and (b) 6 weeks after removal of the polyp. Note the presence of the band for the ras encoded p21 protein in (a) which is not seen in (b).

DETAILED DESCRIPTION OF THE INVENTION

The present invention contemplates monoclonal receptor molecules to oncoprotein ligands, a general method of inducing or raising such receptors, and products and methods that utilize those receptors. Terms used frequently herein are defined as follows:

Receptor—A "receptor" is a biologically active molecule that binds to a ligand. The receptor molecules of this invention are intact or substantially intact antibodies or idiotype-containing polyamide portions of antibodies. Biological activity of a receptor molecule is evidenced by the binding of the receptor to its antigenic ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polypeptide portions (antibody combining sites) of antibodies are those portions of antibody molecules that include the idiotype and bind to the ligand, and include the Fab and F(ab')$_2$ portions of the antibodies are well known in the art, and are prepared by the reaction of papain and pepsin, respectively, on substantially intact antibodies by methods that are well known. See for example, U.S. Pat. No. 4,342,566 to Theofilopolous and Dixon. Intact antibodies are preferred, and will be utilized as illustrative of the receptor molecules contemplated by this invention.

Monoclonal receptor—A "monoclonal receptor" (Mab) is a receptor produced by clones of a single cell called a hybridoma that secretes but one kind of receptor molecule. The hybridoma cell is fused from an antibody-producing cell and a myeloma or other self-perpetuating cell line. Such receptors were first described by Kohler, and Milstein, *Nature*, 256, 495–497 (1975), which description is incorporated by reference.

Oligoclonal receptor—An "oligoclonal receptor" is a receptor that is induced by and binds to more than one epitope on a polypeptide of moderate length such as about 7 to about 40 or more preferably about 10 to about 30 amino acid residues long. Oligoclonal receptors are usually a mixture of receptors produced by more than one cell. Oligoclonal receptors so produced are usually more epitopically specific in their binding than are the polyclonal receptors raised to whole protein molecules that can have epitopic regions throughout the length of the protein chain or chains. Animals immunized with the polypeptides useful herein produce sera containing oligoclonal receptors (antibodies).

Ligand—A "ligand" is the protein or polypeptide to which a receptor of this invention binds.

Corresponds—The term "corresponds" as used herein in conjunction with amino acid residue sequences means that the amino acid residue sequence of a first polypeptide or protein is sufficiently similar to the amino acid residue sequence contained in a second polypeptide or protein so that receptors raised to the first (e.g., an antigenic synthetic polypeptide) immunologically bind to the second (e.g., an oncoprotein) when the two are admixed in an aqueous composition. Such corresponding polypeptides and/or proteins can also be said to contain homologous epitopes, and therefore share homologous sequences of at least about 6 to about 8, e.g., 7, residues.

The epitope-containing amino acid residue sequences of the corresponding first and second polypeptides or proteins are most preferably identical. However, changes, preferably conservative, in amino acid residues, and deletions or additions or residues, within the epitope may be made and still permit the cross-reaction of a receptor to the first polypeptide or protein with the second, as is known. Conservative changes in amino acid residues are well known, and include exchanges of residues between lysine (Lys; K) and arginine (Arg; R), between aspartic acid (Asp; D) and glutamic acid (Glu; E), between leucine (Leu; L) and isoleucine (Ile; I) and the like.

The preferred polypeptides useful herein are frequently described as having an amino acid residue sequence that corresponds to a portion of amino acid residue sequence of a protein. Such polypeptides preferably only contain amino acid residue that correspond identically, in addition to terminal residues such as Cys residues utilized for binding or linking the polypeptides to a carrier. Additional amino acid residues that do not correspond to residues in the protein may also be present at polypeptide termini, but the use of such residues, while contemplated herein, is usually wasteful, and is not preferred.

Similarly, proteins are described as having an amino acid residue sequence to a portion of which the amino acid residue sequence of a polypeptide corresponds. This terminology is intended to imply the same relationship between the polypeptide and protein discussed hereinabove.

The full names for individual amino acid residues are sometimes used herein as are the well-known three-letter abbreviations. The one-letter symbols for amino acid residues are used most often. The Table of Correspondence, below, provides the full name as well as the abbreviations and symbols for each amino acid residue named herein.

Table of Correspondence

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine + aspartic acid | Asx | B |
| Cysteine | Cys | C |
| Glutamine | Gln | Q |
| Glutamic acid | Glu | E |
| Glutamine + glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

(A. L. Lehninger, Biochemistry; Worth Publishers, Inc., N.Y., N.Y., 1970)

I. PRODUCTION OF MONOCLONAL RECEPTORS

As noted previously, the present invention contemplates monoclonal receptor molecules that bind to an immunogenic polypeptide of moderate length, e.g., about 7 to about 40 residues and preferably about 10 to about 30 residues, as well as binding to a protein molecule ligand, a portion of whose amino acid residue sequence corresponds to the amino acid residue sequence of that polypeptide. The monoclonal receptors of this invention are raised or induced by use of an immunogenic polypeptide or conjugate of that polypeptide linked to a carrier; the immunogenic polypeptide containing an amino acid residue sequence of moderate length corresponding to a protein of the amino acid residue sequence of the protein molecule ligand.

Epitopic localization of monoclonal antibodies poses technical problems. Monoclonal antibodies to the entire bacterial gene products can be produced with two different types of immunogens, native or denatured. Use of native protein poses the most serious technical problems regarding purification and subsequent epitope mapping. The chief advantage of using a native protein is the production of monoclonal antibodies that block the biological function of the target protein.

The oncogene product produced in bacteria is typically not structurally the same as the gene product synthesized in higher organisms. Direct evidence for this difference is provided by analysis of the sis gene product. In mammalian cells the p28$^{sis}$ is rapidly cleaved into p20$^{sis}$. In contrast, bacterial p28$^{sis}$ is not cleaved nor does it form a dimer.

Indirect evidence for differences between other oncogene products produced in bacteria or avian cells is provided by the observation that monoclonal antibodies raised against the *E. coli*-produced protein product bind much more efficiently to the immunogen than to the protein synthesized in transformed chicken cells, even though the immunogen was denatured.

It is seen that the sequence of the viral oncogene can provide a basis for identifying additional regions of a protooncogene sequence that can be useful for synthesizing additional peptides for the generation and isolation of additional monoclonal receptors. Similarly, the sequence analysis of these proto-oncogenes identifies additional related peptides that have not yet been isolated in a retrovirus.

Thus, although purification of denatured protein is technically easier, the resulting antisera may recognize conformations unique to the bacterial gene product. This observation poses serious technical difficulties for epitope mapping studies.

Approaches for defining the epitope of the antibodies employ protein fragments generated by partial proteolysis or expression if subgenomic fragments. Although mapping of epitopes using protein fragments was first demonstrated by Niman and Elder, *Proc. Natl. Acad. Sci. USA*, 77, 4524 (1980), only an approximation of the binding sites could be made even when several digests were assayed with a large panel of monoclonal antibodies. Thus, immunization even with protein fragments limits the definition of the binding site. Furthermore, there is no guarantee that regions of interest will induce monoclonal antibodies.

In contrast, immunization with appropriate polypeptides of known amino acid residue sequence as carried out herein, assures a production of antibodies (receptors) that immunoreact with well defined regions; i.e., regions that correspond to the sequences of the immunizing polypeptides.

Mapping of epitopes suggests that changing the epitope by one amino acid may produce markedly different reactivities, while other studies show that cross-reactivities are obtained when one or more amino acid residues are different within the epitope. Furthermore, immunization of the same strain of mouse with the same synthetic polypeptide may produce different reactivities detected in the serum.

Hybridomas produced with synthetic polypeptides also produce monoclonal receptors that react with the intact protein under a variety of reaction conditions because the recognition is largely conformationally independent. Therefore, Western blot, dot blot, fixed cells, and fixed tissues and body fluids such as cellular extracts, amniotic fluid, and urine, either concentrated or as obtained, can be assayed a well as native proteins. Furthermore, the known, precisely defined amino acid residues in the epitope allow isolation of antibodies that can distinguish single amino acid changes, therefore providing a means of determining the significance of limited changes in conserved regions of related proteins.

Monoclonal antibodies against synthetic polypeptides also provide a means of mapping sites of protein interaction. Differential coprecipitations of molecules associated with pp60$^{src}$ have been reported, suggesting identification of regions of src proteins that are involved in such interactions.

Thus, inducing the production of monoclonal antibodies (receptors) with an immunogenic synthetic immunoreact with domains defined by the sequence of the immunizing polypeptide does not require complex methodologies for isolation of isolation of the corresponding immunogenic oncoprotein or the identification of that oncoprotein's epitopic site, and produces receptors that recognize the oncogene product in a conformation independent manner, all of which broaden the application of such receptors for a variety of studies.

It was noted previously that although animal host protection has been shown to be possible by the use of immunogenic polypeptides as the active agents in vaccines, the ability to utilize such immunogenic polypeptides to produce high yields of hybridoma antibodies (Mabs) was not heretofore thought a likely possibility. Since each Mab is derived from a single cell that produces only one specificity, the ratio of the number of clones producing anti-polypeptide antibodies that also recognize the intact protein molecule, to the total number of polypeptide recognizing clones can provide a reasonable estimate of the true confirmational frequency of the polypeptide.

The results described herein are contrary to the beforementioned stochastic model, and the frequency for the moderate-length polypeptides used herein assuming a conformation similar to that of the native protein is much higher than was previously expected. The frequency of producing hybridomas whose Mabs recognize both the synthetic polypeptide to which they were raised and the intact molecule is about 4 orders of magnitude (about 10,000) times greater than that predicted by the stochastic theory.

It is also noted that various workers have been utilizing immunogenic polypeptides to raise antibodies that recognize those polypeptides for several decades. In addition, the above-referenced Kohler and Milstein article as to the production of monoclonal antibodies was published in 1975. Since that date, 1975, Arnheiter et al., *Nature (London)*, 294, 278–280 (1981) described an attempt to prepare a monoclonal antibody using a polypeptide immunogen. As was previously noted, the Arnheiter et al. results must be viewed as a failure in that those authors required the use of the spleens of three immunized mice and obtained only one IgG type monoclonal antibody that recognized their large, 56-mer polypeptide as well as the protein to whose sequence that polypeptide corresponded.

It is believed that the relative paucity of published reports relating to the preparation of monoclonal receptors prepared from immunogenic polypeptides that recognize both the immunogen and a protein ligand to whose amino acid sequence the immunogenic polypeptide corresponds in part is due to at least two factors. First, the prevalent thought following the stochastic model predicts that few if any such monoclonal antibodies could be prepared. Second, the fact that workers such as Arnheiter et al., above, did not possess a method suitable for the preparation of the monoclonal receptors, inasmuch as the monoclonal receptors of this invention that are raised to polypeptides are prepared differently from monoclonal antibodies prepared to whole proteins.

Thus, to successfully prepare IgG class monoclonal receptors that recognize both the immunogenic polypeptide and the protein ligand to whose amino acid residue sequence that polypeptide corresponds in part, one should follow the steps outlined hereinbelow.

An immunogenic polypeptide alone, or as a conjugate of that polypeptide bound (linked) to a carrier is provided. The polypeptide has an amino acid residue sequence of moderate length, such as about 7 to about 40 amino acid residues, and preferably about 10 to about 30 residues. The amino acid residue sequence of the immunogenic polypeptide corresponds to a portion of the amino acid residue sequence of a protein molecule ligand such as an oncoprotein. While the immunogenic polypeptide can be used by itself as a ligand, it is preferred to use the polypeptide immunogen as a conjugate bound to a carrier such as keyhole limpet hemocyanin (KLH), albumins such as bovine serum albumin (BSA), human serum albumin (HSA), red blood cells such as sheep erythrocytes, tetanus toxoid and edestin, as well as polyamino acids such as poly(D-lysine: D-glutamic acid), and the like.

The immunogenicity and antigenicity of the polypeptide may be tested by binding the polypeptide to a keyhole limpet hemocyanin carrier as a conjugate, and then using the conjugate so prepared to immunize a mouse. The immunizing polypeptide or conjugate is dissolved or dispersed in a physiologically tolerable diluent such as normal saline, phosphate-buffered saline or the like as are well known in the art. An adjuvant, discussed below, is also included in the inoculum used for immunizations.

A useful polypeptide is sufficiently immunogenic and antigenic to produce a 50 percent binding titer of the immunized mouse's oligoclonal receptor-containing antiserum to the polypeptide that is at least about a 1:400 dilution after three immunizations in a one-month period, each of which immunizations contains at least about ten micrograms, and preferably at least about 50 micrograms, of the polypeptide in the conjugate, and utilizing complete Freund's adjuvant for the first immunization and alum as adjuvant thereafter.

This test procedure need not be carried out prior to the use of a given polypeptide as immunogen, but it is preferable to do so as a pre-screening technique to determine that polypeptides will be useful in preparing the desired monoclonal receptors. Whether used as a pre-screen or not, the polypeptides useful herein as immunogens provide the above titer using the above immunization regimen.

Upon provision of the immunogenic polypeptide, a mammal such as a mouse, rabbit, goat, horse or the like, is hyperimmunized with the immunogenic polypeptide or conjugate of that polypeptide bound to a carrier to provide a hyperimmune serum whose receptor molecules exhibit a 50 percent binding titer to the polypeptide of at least about a 1:400 dilution. Thus, the same animal, e.g., a mouse, in which one may desire to pre-test the immunogenicity of the polypeptide may be used for raising the Mabs.

It is particularly preferred that the same animal that is used for a pre-test be used for raising the Mabs. This preference stems from the fact that once the above 50 percent binding titer is achieved, the preparation of hybridomas secreting monoclonal antibodies of the desired specificity using the spleen of that animal as the source of antibody-producing cells is substantially assured, aside from the occurrence of random laboratory mishaps such as contamination of cell cultures or otherwise destroying those cultures.

It is noted that the immunization regimen required to provide a hyperimmune state is a function, inter alia, of the animal type, animal weight, the immunogenicity and amounts of the polypeptide and carrier, if used, the adjuvant, if used the number of immunizations administered in a given time period, as is known. The above-described regimen for obtaining a 50 percent binding titer dilution of at least about 1:400 provides a hyperimmune state in the test mouse and may be used as a proportionalizable basis for inducing hyperimmune states in other animals. It is further noted that three immunizations are not necessarily required to provide the hyperimmunized state, but for a useful polypeptide, three such immunizations in a one-month period are sufficient to produce that state, or the polypeptide is not sufficiently immunogenic for the high yield production of hybridomas and their monoclonal antibodies of this invention.

The serum oligoclonal receptor molecules so produced in the hyperimmunized animal also bind to the protein molecule ligand, to a portion of which the immunogenic polypeptide corresponds in amino acid residue sequence. Binding assays are described in the Materials and Methods Section hereinafter. It is noted that a pure sample of the protein molecule ligand need not be utilized in these assays but rather, a cell extract or tissue preparation such as a microscope slide containing the protein ligand may be utilized.

The hyperimmunized animal is maintained; i.e., kept alive without administration of further immunizations for a period of at least about 30 days after administration of the immunization that produces a 50 percent binding titer of at least a 1:400 dilution. In other words, the animal is first immunized to provide a hyperimmunized state, and then the hyperimmunization allowed to recede.

The decline in binding activity typically takes one to about fives months for mice. This decline in binding titer is believed to correspond to a period in which primed blast cells become capable of mounting a vigorous response when the immunogen is again introduced.

A booster immunization, as by intravenous injection, using the immunogenic polypeptide or its conjugate is administered to the animal after the period of maintenance is completed, e.g., at least 30 days after the last immunization. Antibody-producing cells, such as spleen cells or lymph cells of the boosted animal are then fused with a myeloma cell from the same animal type (species) within a period of about three to about five days from the day of booster administration to prepare hybridoma cells. The boost is believed to stimulate the maturation of the blast cells to the point at which those cells secrete nearly optimal amounts of oligoclonal antibodies to the polypeptide.

The SP2/O-Ag14 (ATCC CRL 1581), hypoxanthine-aminopterin-thymidine (HAT)-sensitive, myeloma cell line is preferred for use in fusion with mouse spleen cells, although other cell lines such as P3X63-Ag8.653 may also be utilized. Details using this HAT line for fusion are given hereinafter in the Materials and Methods Section. The hybridoma cells are thereafter cloned at limiting dilution free from the presence of, or need for, feeder layers of macrophages to reduce overgrowth by non-producing cells, and to provide a selection method for cells which grow readily under in vitro conditions. Such feeder layers may, however, be used.

The hybridoma cells so prepared are then assayed for the production (secretion) of monoclonal receptor molecules that bind to the protein molecule ligand. This ligand is a portion of the protein to which the immunogenic polypeptide corresponds in amino acid residue sequence. Thereafter, the hybridoma cells that produce monoclonal receptor molecules that bind to the protein ligand are cultured further to prepare additional quantities of those hybridoma cells, and the monoclonal receptors secreted by those cells that bind to the protein molecule ligand. Typically, such culturing is done at limiting dilution, e.g., at an average of about one cell per culture-growing well.

In preferred practice, the hybridoma cells that are prepared are also assayed for the production of monoclonal receptor molecules that bind to the polypeptide immunogen as well as the protein ligand. Thereafter, hybridoma cells that produce monoclonal receptor molecules that bind to both the immunogenic polypeptide and to the protein ligand are those cells that are preferably cultured.

Where samples of the protein molecule ligand are limited, it is convenient to first screen the hybridomas for secretion of monoclonal receptors that bind to the immunogenic polypeptide. Hybridoma clones that exhibit positive binding to that polypeptide are then typically frozen for storage. They are thereafter thawed, and subcloned by limiting dilution for assurance that truly monoclonal antibodies are produced, rather than a plurality of monoclonal receptors being produced from a plurality of different hybridoma cells. Those limiting dilution subcloning cultures are again typically carried out free from feeder layers or macrophages, as such are not necessary.

The hybridoma cells that are ultimately produced may be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid are typically 129xBALB/c mice bred in the mouse colony of the Scripps Clinic and Research Foundation, La Jolla, Calif. However, when animals other than mice are used for preparation of the hybridomas, that animal type is used for the production of ascites fluid.

As noted previously, it is preferred that the myeloma cell line be from the same species as the receptor. Therefore, fused hybrids such as mouse-mouse hybrids [Shulman et al., Nature, 276, 269 (1978)] or rat-rat hybrids [Galfre et al., Nature, 277, 131 (1979)] are typically utilized. However, some rat-mouse hybrids have also been successfully used in forming hybridomas [Goding, "Production of Monoclonal Antibodies by Cell Fusion", in Antibody as a Tool, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3X63 Ag8U.1 (ATCC CRL 1597), and Y3-Ag1.2.3. (deposited at Collection Nationale de Cultures de Microorganisms, Paris, France, number I-078) and P3X63Ag8 (ATCC TIB 9). Myeloma lines Sp2/0-Ag14 and P3X63-Aq 8.653 are preferred for use in the present invention.

Thus, following the method of this invention it is now possible to produce relatively high yields of monoclonal receptors that bind to or immunoreact with known, predetermined epitopes of protein molecules such as oncoproteins. In addition, once the skilled worker has produced hyperimmune serum containing oligoclonal antibodies that exhibit a 50 percent binding titer of at least about 1:400 to the immunizing polypeptide, that worker may follow the before-mentioned steps, take the spleen from the hyperimmunized animal, fuse its antibody-producing cells with cells of a myeloma line from the same animal type or strain, and be substantially assured that one or more hybridomas produced from that fusion secrete monoclonal receptors that bind to the immunizing polypeptide and to the corresponding protein, such as an oncoprotein. Such results were not heretofore possible.

The above method is useful for preparing hybridomas that secrete monoclonal receptors to substantially any protein molecule ligand. Illustrative of such hybridomas and their monoclonal receptors are those raised to immunogenic polypeptides of moderate length whose amino acid residue sequences correspond to amino acid residue sequences of oncoproteins encoded by oncogenes. Exemplary oncogenes and useful immunogenic polypeptides are shown below followed by the parenthesized, numerical position from the amino-terminus in the oncoprotein sequence to which the polypeptide corresponds wherein the amino acid residue sequences of those polypeptides are given from left to right and in the direction of amino-terminus to carboxyterminus, and are represented by a formula selected from the group consisting of formulae shown in Table 1, below:

TABLE 1

| Polypeptide Number | Oncogene[1] | Polypeptide Sequence |
|---|---|---|
| 109 | v-sis | DPIPEELYKNLSGHSIRSF (8–26) |
| 113 | v-sis | RKIEIVRKKPIFKKATV (138–154) |
| 114 | v-sis | RVTIRTVRVRRPPKGKHRKC (191–210) |
| 116 | v-sis | TRSHSGGELESLARGKR (50–66) |
| 120 | v-sis | CKHTHDKTALKETLGA (210–225) |
| 110 | c-sis | LVSARQGDPIPEELVE (1–16) |
| 111 | PDGF-1 | SIEEAVPAVCKT (1–12) |
| 112 | PDGF-2 | SLGSLTIAEPAMIAECKT (1–18) |
| 113 | PDGF-2 | RKIEIVRKKPIFKKATV (73–89) |
| 114 | PDGF-2 | RVTIRTVRVRRPPKGKHRKC (126–145) |
| 121 | v-fes$^{ST}$ | IGRGNFGEVFSG (519–530) |
| 122 | v-fes$^{ST}$ | IHRDLARRNCLVIEKN (632–647) |
| 123 | v-fes$^{ST}$ | VPVKWTAPEALNYGR (674–688) |
| 124 | v-fes$^{ST}$ | SSGSDVWSFGILLWE (690–704) |
| 125 | v-fes$^{ST}$ | SDVWSFGILLWETFSLGASPYPNLSNQQTR (693–722) |
| 126 | v-fes$^{ST}$ | SPYPNLSNQQTR (711–722) |
| 127 | v-fes$^{ST}$ | LMEQCWAYEPGQRPSF (744–759) |
| 128 | v-fes$^{ST}$ | CWAYEPGQRPSF (748–759) |
| 129 | v-fes$^{ST}$ | LWETFSLGASPYPNLSNQQTR (702–722) |
| 131 | v-myb | RRKVEQEGYPQESSKAG (2–18) |
| 132 | v-myb | RHYTDEDPEKEKRIKELEL (94–112) |
| 133 | v-myb | LGEHHCTPSPPVDHG (160–175)[3] |
| 141 | v-ras$^{Ha}$ | KLVVVGARGVGK (5–16) |
| 142 | v-ras$^{Ha}$ | YREQIKRVKDSDDVPMVLVGNKC (96–118) |
| 146 | v-ras$^{Ha}$ | YTLVREIRQHKLRKLNPPDESGPGC (157–181) |
| 232 | v-ras$^{Ha}$ | DGETCLLDILDTTGQEEY (47–64) |
| 143 | v-ras$^{Ki}$ | KLVVVGASGVGK (5–16) |
| 147 | v-ras$^{Ki}$ | YTLVREIRQYRLKKISKEEKTPGC (157–180) |
| 148 | v-ras$^{Ki}$ | YREQLKRVKDSEDVPMVLVGNKC (96–118) |
| 144 | T24-ras$^{Hu}$ | KLVVVGAVGVGK (5–16) |
| 145 | N-RAS | KLVVVGAGGVGK (5–16) |
| 231 | N-RAS | DGETCLLDILDTAGQEEY (47–64) |
| 237 | N-RAS | YTLVREIRQYRMKKLNSSDDGTQGC (157–181) |
| 233 | H-RAS | YKRMKKLNSSDDGTQGC (166–182) |
| 234 | K-RAS | AGPEAQRLPGLLK (−13 to −1) |
| 235 | K-RAS | CGDSLAARQGAGRR (−180 to −167) |
| 236 | ras$^{K4B}$ | KHKEKMSKDGKKKKKKSKTKC (165–184) |
| 149 | v-bas | KLVVVGAKGVGK (5–16) |
| 150 | MYC | APSEDIWKKFELLPTPPLSP (44–63) |
| 151 | MYC | CDEEENFYQQQQQSEL (25–40) |
| 152 | MYC | PAPSEDIWKKFEL (43–55) |
| 153 | MYC | LPTPPLSPSRRSGLC (56–70) |
| 154 | MYC | CDPDDETFIKNIIIQDC (117–133) |
| 155 | MYC | CSTSSLYLQDLSAAASEC (171–188) |
| 156 | MYC | CASQDSSAFSPSSDSLLSSTESSP (208–231) |
| 157 | MYC | CTSPRSSDTEENVKRRT (342–358) |
| 158 | MYC | SVQAEEQKLISEEDLLRKRR (405–424) |
| 159 | MYC | LRKRREQLKHKLEQLRNSC (420–438) |
| 160 | MYC | IIQDCMWSGFSAA (128–141) |
| 182 | N-MYC | PPGEDIWKKFELLPTPPLSP (44–63) |
| 183 | N-MYC | VILQDCMWSGFSAR (110–123) |
| 184 | N-MYC | SLQAEEHQLLLEKEKLQARQ (432–451) |
| 185 | N-MYC | LQARQQQLLKKIEHARTC (447–464) |
| 192 | L-MYC | APSEDIWKKFELVPSPPTSP (44–63) |
| 193 | L-MYC | IIRRDCMWSGFSAR (110–123) |
| 161 | v-mos | LPRELSPSVDSR (42–53) |
| 162 | v-mos | RQASPPHIGGTY (260–271) |
| 163 | v-mos | TTREVPYSGEPQ (301–312) |
| 164 | v-mos | IIQSCWEARGLQRPSA (344–359) |
| 165 | v-mos | LGSGGFGSVYKA (100–111) |
| 168 | v-mos | TLWQMTTREVPYSGPQYVQYA (296–317)[3] |
| 761 | v-mos | TLWQMTTREVPYSGEPQYVQY (296–316) |
| 166 | c-mos | IIQSCWEARALQRPGA (344–359) |
| 167 | MOS | VIQRCWRPSAAQRPSA (316–331) |
| 762 | MOS | TLWQMTTKQAPYSGERQHILY (268–288) |
| 171 | v-erb B | IMVKCWMIDADSRPKF (366–381) |
| 172 | v-erb B | LGSGAFGTIYKG (138–149) |
| 173 | v-erb B | ENDTLVRKYADANAVCQ (23–39) |
| 174 | v-erb B | VWELMTFGSKPYDGIPASEIS (324–344) |
| 175 | neu | IMVKCWMIDSECRPRF (959–974) |
| 178 | neu | VWELMTFGAKPYDGIPAREIP (917–937) |
| 179 | neu | LGSGAFGTVYKG (731–742) |
| 176 | HER-1 | RRRHIVRKRTLRRLLQERE (645–663) |
| 177 | HER-1 | VWELMTFGSKPYDGIPASEIS (880–900) |

TABLE 1-continued

| | | |
|---|---|---|
| 207 | v-src | LLNPENPRGTFLVRESETTKG (162–182) |
| 208 | v-src | TFVALYDYESRTETDLSFKKGERL (85–108) |
| 202 | v-src$^{PC}$ | LGQGCFGEVWMG (273–284) |
| 205 | v-src$^{PC}$ | LTELTTKGRVPYPGMVNREVL (452–472) |
| 201 | v-src$^{PC}$ | LMCQCWRKDPEERPTF (494–509) |
| 203 | v-src$^{SRA}$ | GSSKSKPKDPSQRRRS (2–17) |
| 204 | v-src$^{SRA}$ | LTELTTKGRVPYPGMGNGEVL (452–472) |
| 206 | SRC | LMCQCWRKEPEERPTF (Note 2) |
| 211 | v-fgr | AMEQTWRLDPEERPTF (631–646) |
| 212 | v-fgr | LGTGCFGDVWLG (410–421) |
| 213 | v-fgr | LTELISKGRVPYPGMNNREVL (589–609) |
| 214 | FGR | LTELITKGRIPYPGMNKREVL |
| 215 | FGR | LLNPGNPQGAFLIRESETTKG (48–68) |
| 221 | int-1 | DYRRRGPGGPDWHWGGC (154–170) |
| 222 | int-1 | LHNNEAGRTTVFS (200–212) |
| 223 | int-1 | EPEDPAHKPPSPHDL (275–289) |
| 224 | int-1 | RACNSSSPALDGCEL (313–327) |
| 240 | v-yes | LMKLCWKKDPDERPT (778–792) |
| 241 | v-yes | LTELVTKGRVPYPGMVNREVL (736–756) |
| 242 | v-yes | VFVALYDYEARTTDDLSFKKGERF (369–393) |
| 243 | v-yes | LLNPGNQRGIFLVRESETTKG (446–466) |
| 250 | v-mil | LVADCLKKVREERPLF (317–332) |
| 252 | v-mil | VLYELMTGELPYSHINNRDQI (270–290) |
| 251 | v-raf | IGSGSFGTVYRG (355–366)$^3$ |
| 260 | v-raf | LVADCVKKVKEERPLF (285–300) |
| 261 | v-raf | VLYELMAGELPYAHINNRDQI (237–258) |
| 253 | RAF | IGSGSFGTVYKG (355–366) |
| 262 | A-RAF | LLTDCLKFQREERPLF (374–389) |
| 266 | A-RAF | VLYELMTGSLPYSHIGSRDQI (327–347) |
| 254 | PKS | IGTGSFGTVFRG (25–36) |
| 255 | PKS | VLYELMTGSLPYSHIGCRDQI (207–227) |
| 256 | PKS | LLSDCLKFQREERPLF (254–269) |
| 270 | v-rel | TLHSCWQQLYSPSPSA (382–397) |
| 290 | v-fms | LGTGAFGLVVEA (1093–1104)$^3$ |
| 291 | v-fms | LWEIFSLGLNPYPGILVNSKF (1336–1356) |
| 292 | v-fms | FMQACWALEPTRRPTF (1379–1394)$^3$ |
| 293 | v-fms | LGTGAFGKVVEA (1078–1089) |
| 295 | FMS | IMQACWALEPTHRPTF (888–903) |
| 296 | FMS | LEAGVSLVRVRGRPLMR (134–150) |
| 297 | FMS | LYVKDPARPWNVLAQE (99–114) |
| 298 | FMS | VPAELVRIRGEAAQIVC (208–224) |
| 310 | v-abl | LGGGQYGEVYEG (367–389) |
| 311 | v-abl | LWEIATYGMSPYPGIDLSQVY (548–568) |
| 312 | v-abl | LMRACWQWNPSDRPSF (590–605) |
| 313 | c-abl I | KSKKGLSSSSSCYLE (12–26) |
| 314 | c-abl I | LLSSGINGSFLVRESESSPG (140–159) |
| 315 | c-abl I | LFVALYDFVASGDNTLSITKGEKL (65–88) |
| 316 | c-abl II | DLLSDELHLKLLVLDV (5–20) |
| 317 | c-abl III | RWTYTKCRVQRDPALPFM (4–21) |
| 318 | c-abl IV | QQPGKVLGDQRRPSLPALHFIK (3–24) |
| 320 | BPK C | LGTGSFGRVMLV (48–59) |
| 322 | BPK C | IYEMAAGYPPFFADQPIQIY (227–246) |
| 321 | BPK R | DNHGSFGELALM (197–209) |
| 323 | BPK R | LLRNLLQVDLTKRFGNLK (224–241) |
| 340 | CDC 28 | VGEGTYGVVYKA (14–25) |
| 352 | v-fps | LWEAFSLGAVPYANLSNQQTR (1110–1130) |
| 353 | c-fps | LMQRCWEYDPRRRPSF (888–903) |
| 355 | c-fps | NKLAELGSEEPPPALPLQ (484–501) |
| 360 | v-ros | LGSGAFGEVYEG (254–265) |
| 361 | v-ros | VWETLTLGQQPYPGLSNIEVL (455–475) |
| 362 | v-ros | LMTRCWAQDPHNRPTF (497–512) |
| 366 | ROS | IWEILTLGHQPYPAHSNLDVL (362–382) |
| 367 | ROS | LMTQCWAQEPDQRPTF (404–419) |
| 371 | HIR | LGQGSFGMVYEG (990–1001) |
| 372 | HIR | LWEITSLAEQPYQGLSNEQVL (1187–1207) |
| 373 | HIR | LMRMCWQFNPNMRPTF (1229–1244) |
| 600 | TRK | LGEGAFGKVFLA (339–350) |
| 601 | TRK | LWEIFTYGKQPWYQLSNIEAI (540–560) |
| 602 | TRK | IMRGCWQREPSNATAS (582–597) |
| 661 | v-kit | LWELFSLGSSPYPGMPVDSKF (637–657) |
| 662 | v-kit | IMKTCWDADPLKRPTF (680–695) |
| 701 | PKC | LGKGSFGKVMLA (344–355) |
| 702 | PKC | LYEMLAGQPPFDGEDEDELF (528–547) |
| 703 | PKC | LMTKHPGKRLGCGPEGE (572–588) |
| 711 | PKC | LGKGSFGKVMLS (356–367) |
| 712 | PKC | LYEMLAGQAPFEGEDEDELF (531–550) |
| 713 | PKC | LITKHPGKRLGCGPEGE (575–591) |
| 722 | PKC | LYEMLAGQPPFDGEDEEELF (545–564) |
| 723 | PKC | FLTKHPAKRLGSGPDGE (589–605) |
| 771 | pim-1 | LGSGGFGSVYSG (44–55) |
| 772 | pim-1 | LYDMVCGDIPFEHDEEIIKG (232–251) |
| 773 | pim-1 | LIKWCLSLRPSDRPSF (266–281) |
| 841 | syn | LGNGQFGEVWMG (277–288) |
| 842 | syn | LTELVTKGRVPYPGMNNREVL (456–476) |
| 843 | syn | LMIHCWKKDPEERPTF (498–513) |
| 844 | syn | LFVALYDYEARTEDDLSFHKGEKF (86–109) |
| 845 | syn | LLSFGNPRGTFLIRESETTKG (163–183) |
| 861 | Gs | RLLLLGAGESGK (42–53) |
| 862 | Gs | RWLRTISVILFLNK (279–293) |
| 871 | Gi | KLLLLGAGESGK (35–46) |
| 872 | Gi | KWFTDTSIILFLNK (258–271) |
| 882 | Go | KFFIDTSIILFLNK (214–227) |
| 892 | T | RYFATTSIVLFLNK (253–266) |
| 894 | T | KFFAATSIVLFLNK (257–270) |
| 901 | PBK | LGRGVSSVVRRC (25–36) |
| 902 | PBK | MYTLLAGSPPFWHRKQMLML (219–238) |
| 903 | PBK | LVSRFLVVQPQKRYTAEE (263–280) |
| 911 | CGK | LGVGGFGRVELV (365–376) |
| 912 | CGK | MYELLTGSPPFSGPDPMKTY (547–566) |
| 913 | CGK | LIKKLCRDNPSERLGNLK (589–606) |
| 921 | MLCK | LGGGKFGAVCTCT (67–79) |
| 922 | MLCK | TYMLLSGLSPFLGDDDTETL (248–267) |
| 923 | MLCK | FVSNLIVKEQGARMSAAQC (292–310) |
| 390 | c-lsk | LGAGQFGEVWMG (251–262) |
| 391 | c-lsk | LMMLCWKERPEDRPTF (472–489) |
| 392 | c-lsk | LTEIVTHGRIPYPGMTNPEVI (430–450) |
| 393 | c-lsk | LVIALHSYEPSHDGDLGFEKGEQL (65–88) |
| 394 | c-lsk | LLAPGNTHGSFLIRESESTAG (141–162) |
| 400 | MET | MLKCWHPKAGMRP (Note 2) |
| 401 | MET | LWELMTRGAPPYPDVNTFDFI (Note 2) |
| 402 | MET | VMLKCWHPKAGMRPSF (Note 2) |
| 411 | FOS | SGFNADYEASSRC (4–17) |
| 412 | FOS | LSPEEEEKEKRRIRKGTEYETD (132–153) |
| 413 | c-fos | LSPEEEEKRRIRRERNKMMAAKC (132–154) |
| 414 | c-fos | TLQAETDQLEDEKSALQTEI (164–183) |
| 415 | c-fos | LQTEIANLLKEKEKLEFI (179–196) |
| 416 | c-fos | RKGSSSNEPSSDSLSSPTLL (359–378) |
| 421 | TGF-alpha | VVSAFNDCPDSHTQFC (1–16) |
| 423 | TGF-alpha | FHGTCRFLyQEDKPA (17–31) |
| 424 | TGF-alpha | HSGYVGVRCEHADL (34–47) |
| 431 | EGF | NSDSECPLSHDGYC (1–13) |
| 432 | EGF | CLHDGVCMYIEALDKYAC (15–30) |
| 441 | bcl-1 | |
| 442 | bcl-1 | RPPQVPAFRRPKSAEPTC |
| 443 | bcl-1 | CITVEGRNRGPG |
| 444 | bcl-1 | KLMELRIPLSRKSSRGC |
| 461 | v-erb A | KSFFRRTIQKNLHPTSC (58–75) |
| 462 | v-erb A | VDFAKNLPMFSELPCEDQ (214–231) |
| 463 | v-erb A | ELPPRRCRALQILGSILPFV (379–398) |
| 470 | HGR | KVFFKRAVEGQHNYLCAGR (442–460) |
| 471 | HGR | NVMWLKPESTSHTLI (728–742) |
| 472 | HGR | TNQIPKYSNGNIKKLLFHQK (758–777) |
| 473 | HGR | VKWAKAIPGFRNLHLDDQ (575–592) |
| 800 | ER | KAFFKRSIQGHNKYMCPA (206–223) |
| 801 | ER | INWAKRVPGFVDLTLHDQ (358–375) |
| 477 | cPR | KVFFKRAMEGQHNYLCAGR (Note 2) |
| 1000 | Beta-TGF | ALDTNYCFSSTEKNC |

$^1$Literature citations for the above oncogenes and sequences.
v-sis - Devare et al., Proc. Natl. Acad. Sci. USA, 79, 3179–3182 (1982).
c-sis - Johnsson et al., EMBO J., 3:921–928 (1984).
PDGF-1 - Doolittle et al., Science, 221, 275–277 (1983).
PDGF-2 - Doolittle et al., Science, 221, 275–277 (1983).
v-fes$^{ST}$ - Hampe et al. Cell, 30, 775–785 (1982)
v-myb - Rushlow et al., Science, 216, 1421–1423 (1982).
v-ras$^{Ha}$ - Dhar et al., Science, 217, 934–937 (1982).
v-ras$^{Ki}$ - Tsuchida et al., Science, 217, 937–939 (1982).
T24-ras$^{Ha}$ - Reddy et al., Nature, 300, 149–152 (1982).
N-RAS - Taparowski et al., Cell, 34, 581 (1983).
H-RAS - Capon et al., Nature, 302, 33 (1983).
K-RAS -McGrath et al., Nature, 304, 501 (1983).
ras$^{K4B}$ - Chardin et al., EMBO J. 5, 2203 (1986).
v-bas - Reddy et al., J. Virol, 53, 984 (1985).
MYC - Colby et al., Nature, 301, 722–725 (1983).
N-MYC - Kohl et al., Nature, 319, 73 (1986).
L-MYC - Nau et al., Nature, 318, 69 (1985).
v-mos - Van Beveren et al., Nature, 289, 258–262 (1981).

TABLE 1-continued c-mos - Van Beveren et al., Cell, 27, 97 (1981).
MOS - Watson et al., Proc. Natl. Acad. Sci. USA., 79, 4078 (1982)
v-erb-B - Yamamoto et al., Cell, 35, 71 (1983).
neu - Bargmann et al., Nature, 319, 226 (1986).
HER-1 - Ullrich et al., Nature, 309, 418 (1984).
v-src - Takeya et al., J. Virol., 44, 12 (1982).
v-src^FC - Schwartz et al., Cell, 32, 853 (1983)
v-src^SRA - Czernilofsky et al., Nature, 287, 198 (1980).
SRC - Parker et al., Mol. Cell. Biol., 5, 831 (1985).
v-fgr - Naharro et al., Science, 223, 63 (1984).
int -1 - Ooyen et al., EMBO J., 4, 2905 (1985)
v-yes - Kitamura et al., Nature, 297, 205 (1982).
v-mil - Sutrave et al., Nature, 309, 85 (1984).
v-raf - Mark et al., Science, 224, 285 (1984).
RAF - Bonner et al., Nuc. Acid Res., 14, 1009 (1986).
A-RAF - Huleihel et al., Mol. Cell. Biol., 6, 2655 (1986).
PKS - Mark et al., Proc. Natl. Acad. Sci. USA, 83, 6312 (1986)
v-rel - Stephens et al., Proc. Natl. Acad. Sci. USA, 80, 6229 (1983)
v-fms - Hampe et al., Proc. Natl. Acad. Sci. USA, 81, 85 (1984)
FMS - Coussens et al., Nature, 320, 277 (1986).
v-abl I - Reddy et al., Proc. Natl. Acad. Sci. USA, 80, 3623 (1983)
c-abl I - Ben-Nerich et al., Cell, 44:577 (1986).
c-abl II - Ben-Nerich et al., supra.
c-abl III - Ben-Nerich et al., supra.
c-abl IV - Ben-Nerich et al., supra.
BPK C - Shoji et al., Proc. Natl. Acad. Sci. USA, 78, 848 (1981)
BPK R - Shoji et al., Biochem., 22, 3702 (1983).
CDC 28 - Lorincz et al., Nature, 307, 183 (1984).
v-fps - Shibuya et al., Cell, 30, 787 (1982).
c-fps - Huang et al., J. Mol. Biol., 181, 175 (1985).
v-ros - Neckameyer et al., S. Virol., 53, 879 (1985).
HIR - Ullrich et al., Nature, 313, 756 (1985).
TRK - Martin - Zanca et al., Nature, 319, 743 (1986).
v-kit - Besmer et al., Nature, 320, 415 (1986).
PKC - Kropf et al., Cell, 46 491 (1986).
pim-1 - Selten et al., Cell, 46, 603 (1986).
syn - Semba et al., Proc. Natl. Acad. Sci. USA, 83, 5459 (1986)
Gs - Itoh et al., Proc. Natl. Acad. Sci. USA, 83, 3776 (1986)
Gi - Itoh et al., supra.
Go - Itoh et al., supra.
T - Itoh et al., supra.
T - Itoh et al., supra.
PBK - Reimann et al., Biochem., 23, 4185 (1984).
CGK - Takio et al., Biochem., 23, 4207 (1984).
MLCK - Takio et al., Biochem., 24, 6028 (1985).
c-lsk - Marth et al., Cell, 43, 393 (1985).
MET - Dean et al., Nature, 318, 385 (1985).
FOS - Cochran et al., Science, 226, 1080 (1984).
c-fos - van Straaten et al., Proc. Natl. Acad. Sci. USA, 80, 3138 (1983).
v-erb-A - Weinberger et al., Nature, 318, 670 (1985).
c-erb-A - Weinberger et al., Nature, 324, 641 (1986).
HGR - Hollenberg et al., Nature, 318, 635 (1985)
ER - Greene et al., Science, 231, 1150 (1986).
CPR - Connelly et al., Science, 233, 767 (1986).
Beta-TGF Derynck et al., Nature, 316, 701 (1985).
[2]Numerical position of the polypeptide was not available because the sequence reported was incomplete.
[3]These polypeptides contain a deleted, added or substituted amino acid residue as compared to the reported sequences.

The homologous polypeptides encoded by the above four ras genes may be conveniently written as one amino acid residue sequence, from left to right and in the direction from amino-terminus to carboxy-terminus, represented by the formula

KVVVGAR(S,V,G)GVGK wherein the amino acid residues in parentheses are each an alternative to the immediately preceding amino acid residue, "R", in the formula.

Still further useful polypeptides for inducing the production of monoclonal receptors of this invention are the polypeptides whose oncogene, position in the oncoprotein sequence and polypeptide amino acid residue sequences are shown in FIGS. 20, 21, and 22. Those polypeptides correspond to sequence-conserved regions in the well known family of protein kinase oncoproteins, some of whose oncogenes have been previously noted herein.

II. MONOCLONAL RECEPTORS

While the present invention contemplates a large number of monoclonal receptors, only a relatively few of those contemplated receptors, in the form of intact monoclonal antibodies (Mabs), will be discussed in detail herein as illustrative of the group. The before-discussed test for the immunogenicity and antigenicity of a polypeptide will be discussed thereafter for polypeptides corresponding to additional monoclonal receptors that bind (immunoreact) to different oncoproteins.

A. Exemplary Receptors

Using the procedures discussed herein, exemplary monoclonal receptors were raised to oncogene-related polypeptides.

Hybridomas secreting monoclonal receptors of the invention have been deposited at the American Type Culture Collection (ATCC) in Rockville, Md. pursuant to the Budapest Treaty. A list of those deposits including their ATCC accession number (ATCC No.), laboratory reference number (Ref. No.), date of receipt at the ATCC (ATCC Receipt), and the number of the immunizing polypeptide cross-referenced to the polypeptides of Table 1 (Polypep. No.) is provided in Table 2, below.

TABLE 2

ATCC Deposits

| ATTC No. | Ref. No. | ATCC RECEIPT | POLYPEP No. |
|---|---|---|---|
| B 8593 | P44E11[1] | 08/02/84 | 125 |
| HB 8594 | P43D09 | 08/02/84 | 125 |
| HB 8595 | S22C06 | 08/02/84 | 125 |
| HB 8596 | S10F03 | 08/02/84 | 125 |
| HB 8679 | 1/24-24E05 | 12/12/84 | 142 |
| HB 8800 | 18-9B10 | 05/09/85 | 112 |
| HB 8888 | 133-1E10 | 08/15/85 | 133 |
| HB 8894 | 173-1C11 | 08/27/85 | 173 |
| HB 8895 | 202-11AB | 08/27/85 | 202 |
| HB 8896 | 173-8D2 | 08/27/85 | 173 |
| HB 8897 | 133-6C10 | 08/27/85 | 133 |
| HB 8898 | 203-7D10 | 08/27/85 | 203 |
| HB 8899 | 203-6F5 | 08/27/85 | 203 |
| HB 8900 | 202-9D10 | 08/27/85 | 202 |
| HB 8924 | 132-7C9 | 08/29/85 | 132 |
| HB 8925 | 114-50D4 | 08/29/85 | 114 |
| HB 8926 | 114-50G2 | 08/29/85 | 114 |
| HB 8927 | 132-1C8 | 08/29/85 | 132 |
| HB 8948 | 121-1F9 | 12/03/85 | 121 |
| HB 8949 | 121-3H5 | 12/03/85 | 121 |
| HB 8950 | 121-4F8 | 12/03/85 | 121 |
| HB 8951 | 121-5E5 | 12/23/85 | 121 |
| HB 8952 | 121-9G10 | 12/03/85 | 121 |
| HB 8953 | 121-9E5 | 12/03/87 | 121 |
| HB 8954 | 121-15B10 | 12/03/85 | 121 |
| HB 8955 | 121-19B10 | 12/03/85 | 121 |
| HB 8956 | 121-8D8 | 12/04/85 | 121 |
| HB 8965 | 127-24C7 | 12/11/85 | 127 |
| HB 8966 | 127-24E11 | 12/11/85 | 127 |
| HB 8967 | 127-38G2 | 12/11/85 | 127 |
| HB 8968 | 127-50D4 | 12/11/85 | 127 |
| HB 8969 | 127-50D12 | 12/11/85 | 127 |
| HB 8970 | 127-53F8 | 12/11/85 | 127 |
| HB 8971 | 127-60F3 | 12/11/85 | 127 |
| — | 127-42C11 | — | 127 |
| HB 8976 | 155-11C7 | 12/17/85 | 155 |

TABLE 2-continued

ATCC Deposits

| ATTC No. | Ref. No. | ATCC RECEIPT | POLYPEP No. |
|---|---|---|---|
| HB 8996 | 152-6D11 | 01/28/86 | 152 |
| HB 8997 | 146-3E4 | 01/28/86 | 146 |
| HB 8998 | 146-17A3 | 01/28/86 | 146 |
| HB 8999 | 146-8D11 | 01/28/86 | 146 |
| HB 9000 | 155-9F6 | 01/28/86 | 155 |
| HB 9001 | 155-8G1 | 01/28/86 | 155 |
| HB 9002 | 310-5F5 | 01/28/86 | 310 |
| HB 9003 | 131-94H4 | 01/28/86 | 131 |
| HB 9004 | 172-12G7 | 01/28/86 | 172 |
| HB 9005 | 172-12A4 | 01/28/86 | 172 |
| HB 9040 | 164-3F3 | 03/19/86 | 164 |
| HB 9052 | 222-35C8 | 03/27/86 | 222 |
| HB 9053 | 310-29F7 | 03/27/86 | 310 |
| HB 9077 | 133-10F6 | 04/17/86 | 133 |
| HB 9097 | 171-19B10 | 05/08/86 | 171 |
| HB 9098 | 171-10E5 | 05/08/86 | 171 |
| HB 9117 | 171-11B9 | 05/29/86 | 171 |
| HB 9133 | 2904E10 | 06/26/86 | 290 |
| HB 9144 | 240-13D10 | 07/10/86 | 240 |
| HB 9208 | 312-13E08 | 09/24/86 | 312 |
| HB 9227 | 361-31C05 | 10/15/86 | 316 |
| HB 9260 | 250-9G06 | 11/06/86 | 250 |
| HB 9278 | 147-67C6 | 11/20/86 | 147 |
| HB 9279 | 165-34E4 | 11/20/86 | 165 |
| HB 9280 | 360-27E06 | 11/20/86 | 360 |

[1]Hybridoma P44E11 was prepared using the myeloma cell line P3X63-Ag 8.653. All other hybridomas were prepared using the myeloma cell line SP2-0, as discussed in the Materials and Methods section.

Five exemplary hybridomas secreting monoclonal receptors were raised to the v-fes related, 30-mer immunogenic, synthetic polypeptide shown below (polypeptide number 125 also referred to as polypeptide a), and each also binds to the carboxy-terminal 12-mer polypeptide shown below (polypeptide 126 also referred to as polypeptide b), as well as binding to the oncoprotein denominated p85 (85K daltons) encoded by the v-fes gene of ST-FeSV. Those hybridomas were given the reference numbers S10F03, S22C06, P43D09, P42C10 and P44E11 These hybridomas have the designations ATCC HB 8596, ATCC HB 8595, ATCC HB 8594, ATCC HB 8593, ATCC HB 8679, respectively. The amino acid residue sequences of synthetic polypeptides (a) and (b), from left to right and in the direction from amino-terminus to carboxy-terminus, are represented by the formulae polypeptide a *SDVWSFGILLWETFSLGASP-YPNLSNQQTR*;

polypeptide b *SPYPNLSNQQTR*.

The seven hybridomas deposited at the ATCC of Table 2 that were raised to the v-res-related polypeptide number 127 and are shown in Table 1 are among the nineteen hybridomas raised to that polypeptide. The monoclonal receptors secreted by those seven hybridomas also bind to the p85 oncoprotein.

The monoclonal receptors of this invention secreted by hybridomas designated S22C06 and S10F03 are particularly preferred monoclonal receptors. Both preferred monoclonal receptors are IgG1 monoclonal receptors, having kappa light chains, that immunoreact with the immunizing polypeptide and with the fes-related oncoprotein having an amino acid residue sequence corresponding to the sequence of the immunizing polypeptide.

A hybridoma was raised using the ras 23-mer immunogenic, synthetic polypeptide number 142 (ras) shown below:

*YREQIKRVKDSDDVPMVLVGNKC.*

The monoclonal antibody secreted by that hybridoma binds to the immunogenic polypeptide and also binds to the 55K dalton protein encoded by the ras gene of the Harvey sequence. The monoclonal antibody recognizes a 23K dalton protein in all ras-producing cell lines tested as well as a higher molecular weight protein.

The hybridomas designated S10F03, S22C06, P43D09, P44E11 and 1/24/E05 secrete kappa-light chained, IgG1 monoclonal receptors. These hybridomas have the designations ATCC HB 8596, ATCC HB 8595, ATCC HB 8594, ATCC HB 8593, ATCC HB 8679, respectively.

The last-named five hybridomas were prepared from three separate cell fusions. The efficiency of producing hybridomas whose Mabs recognize the immunogenic polypeptide as well as the corresponding oncoprotein molecule ligand for the first preparation was 100 percent; i.e., two Mabs (from S10F03 and S22C06) were produced that recognize the polypeptide, and those two Mabs also recognize the oncoprotein. For the second and third preparations, the efficiency, calculated similarly was about 20 percent.

Another hybridoma was raised using the erb-B related, 16-mer immunogenic synthetic polypeptide number 171 shown below. The amino acid residue sequence of the synthetic polypeptide, from left to right and in the direction from amino-terminus to carboxy-terminus is represented by the formula:

*IMVKCWMIDADSRPKF.*

The monoclonal antibody secreted by this hybridoma also binds to polypeptides related to oncoproteins encoded by fes, fms, abl, src and fgr oncogenes. The erb-B related hybridomas have ATCC designations ATCC HB 9097, ATCC HB 9098 and ATCC HB 9117.

Figure 1:
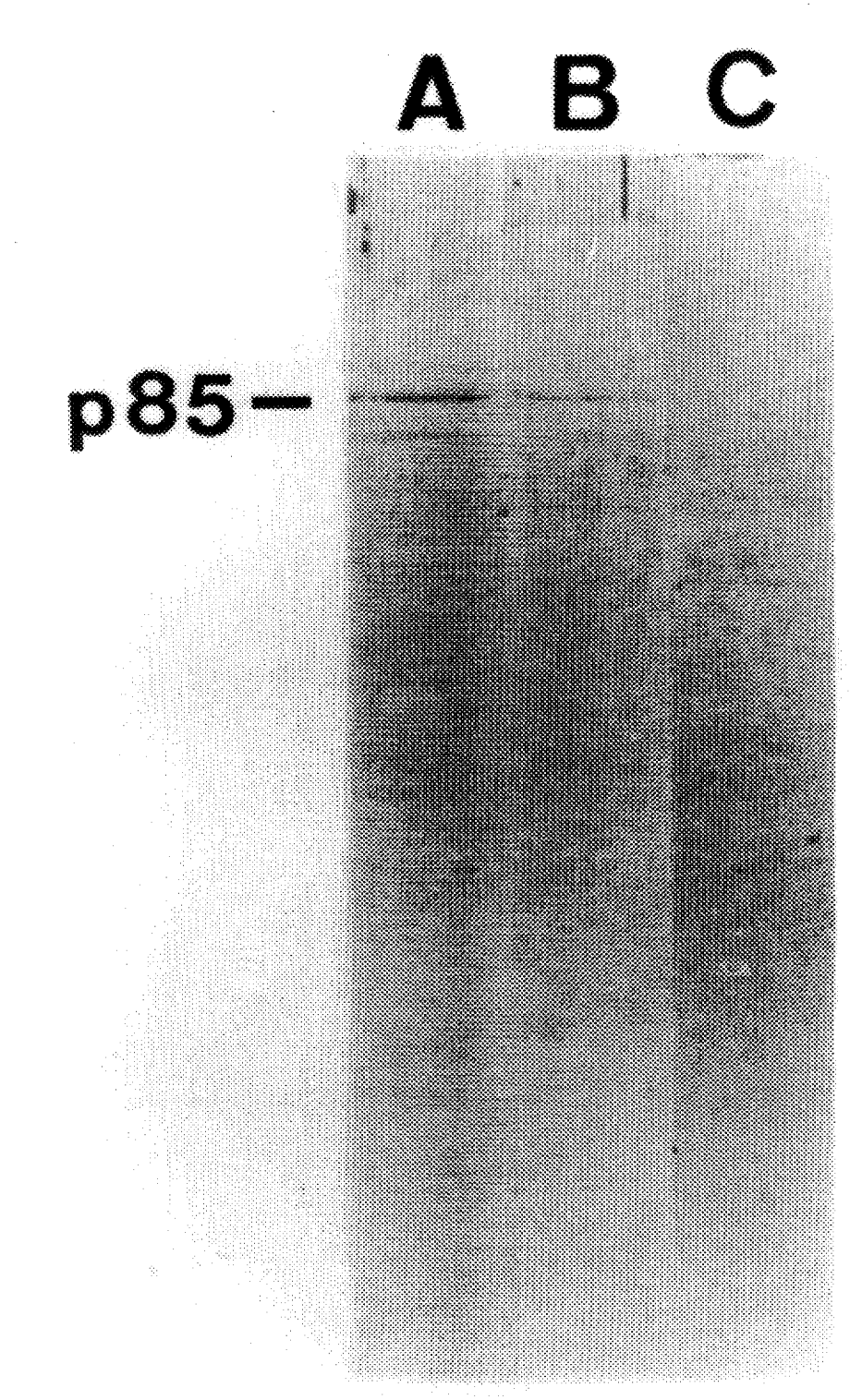

FIG. 1 illustrates the immunological detection of the p85 oncoprotein ligand by the monoclonal receptors secreted by hybridomas S10F03 (ATCC HB 8596) and S22C06 (ATCC HB 8595), using an external standard for the p85 oncoprotein ligand and an influenza hemagglutinin-recognizing Mab as a negative control. FIG. 2 illustrates similar results again using Mabs from hybridoma S10F03 as well as Mabs from hybridomas P43D09 (ATCC HB 8594), and P44E11 (ATCC HB 8593), and also hybridoma P42C10. A monoclonal antibody against the Rauscher virus protein denominated gp70 [Niman and Elder in *Monoclonal Antibodies and T Cell Products*, above] was used as a negative control.

FIG. 3 further illustrates the specificity of the monoclonal receptors of this invention. There, CCL64 mink cells (lanes B and C) or MSTF cells infected with FeLV-B and FeSV (lanes A and B) were radioactively labeled with $^{32}$p. Extracts from the labeled cells were then incubated with either a goat antiserum against the p15 protein encoded by the gag portion of the v-fes gene and expressed as the protein precursor denominated pr65 (lanes A and B) or with tissue culture supernatant from hybridoma S10F03 (lanes C and D) (ATCC HB 8596).

As can be seen, the Mab of this invention from hybridoma S10F03 bound only to the p85 oncoprotein ligand (lane C), while the goat anti-p15 serum bound to both the pr65 and p85 fusion oncoproteins from the infected cells (lane A). No proteins were bound from the uninfected cells (lanes B and D). These results and, by analogy, discussion of the assay concerning FIG. 13, confirm that the Mabs of this invention bind only to the oncoprotein ligand (p85) a portion of whose amino acid residue sequence corresponds to the sequence of the immunogenic polypeptide used to prepare the hybridoma secreting each Mab.

In similar results, not shown, Mabs from the above five hybridomas also bound to the 108K dalton oncoprotein ligand expressed in cells transformed by GA-FeSV. The oncoprotein ligand encoded by the GA-FeSV strain is substantially identical in amino acid residue sequence to the oncoprotein ligand encoded by the ST-FeSV strain in the region of the immunogenically useful polypeptide. See, Hampe et al., *Cell*, 30, 777–785 (1982).

None of the above five Mabs bound to the oncoprotein encoded by the v-fps gene of the Fujinami strain of avian sarcoma virus. The predicted v-fps oncoprotein, whose sequence is reported by Shibuya et al., *Cell*, 30, 787 (1982), also contains extensive homologies to the predicted v-fes oncoprotein and differs in the region corresponding to the above 12-mer (polypeptide b) only by the substitution of the first and fourth residues from the amino-terminus of that 12-mer polypeptide; i.e., the amino-terminal serine (S) of the v-fes-related polypeptide and oncoprotein is replaced by a valine (V) in the v-fps-related oncoprotein, and the second proline (P) residue from the amino-terminus is replaced by an alanine (A) residue.

The non-binding of the above Mabs to the v-fps-related oncoprotein provides a basis for distinguishing among expressed oncoproteins in transformed cells, and for assaying for the presence of the v-fes-related oncoprotein ligand in the presence of the v-fps-related oncoprotein. That distinction in binding can also be useful in purifying a mixture of both proteins by affinity chromatography utilizing an Mab of this invention as a portion of an affinity sorbant, as is discussed hereinafter.

The above non-binding of the monoclonal antibodies of this invention to the v-fps-related oncoprotein also highlights the improvement in specificity of the monoclonal receptors over previously obtained oligoclonal receptors. Thus, Sen et al., *Proc. Natl. Acad. Sci. USA*, 80, 1246–1250 (1983), used polypeptide (b) above conjugated to KLH to prepare rabbit oligoclonal antibodies. Those oligoclonal antibodies bound to oncoproteins expressed in cells transformed by ST-FeSV, GA-FeSV and FSV (Fuginami sarcoma virus) that contain the v-fes$^{ST}$, v-fes$^{GA}$ and v-fps oncogenes, respectively. It can therefore be seen that the specificity obtained from the monoclonal receptors of this invention is greatly improved over that obtained with oligoclonal receptors even when both are raised to the same immunogenic polypeptide.

In a similar manner are prepared hybridomas that secrete monoclonal receptors that bind to oncoprotein molecule ligands, e.g., PDGF, to immunogenic polypeptides encoded by the retroviral oncogenes denominated fes, myb, fos, sis, ras, myc and mos, as well as to immunogenic polypeptides whose sequences correspond to sequences of oncoproteins encoded by oncogenes denominated fps, src, yes, fgr, bas, int-1, fms, erb-A, erb-B, mil, raf (mil/raf), abl and ros, as well as growth factors PDGF1, PDGF-2, EGF, TGF-alpha and also to oncoproteins expressed in cells transformed by retroviruses containing those genes. Specific monoclonal receptors of this invention bind to an immunogenic polypeptide encoded by the above oncogenes.

Some of those oncogenes are named below in Table 3 and are illustrated adjacent to polypeptide numbers correlated to the oncogenes, sequences and polypeptide numbers of Table 1 to which the preferred monoclonal receptors of this invention bind. Data relating to the binding of at least one monoclonal receptor (Mab) or oligoclonal antiserum (serum) raised to each polypeptide in a Western blot analysis are also provided in Table 3 adjacent to the polypeptide number.

TABLE 3

Receptor Binding To Oncoproteins[1]

| Oncogene | Polypep. No. | Mab Binding To Oncoprotein[3] | Serum Binding, To Oncoprotein[4] |
|---|---|---|---|
| sis | 110 | + | NT |
|  | 111 | + | + |
|  | 112 | + | + |
|  | 113 | NT | + |
|  | 114 | + | + |
| fes | 121 | + | + |
|  | 122 | NT | NT |
|  | 123 | NT | + |
|  | 124 | NT | NT |
|  | 125 | + | + |
|  | 126 | NT | + |
|  | 127 | + | + |
| myb | 131 | + | + |
|  | 132 | + | + |
|  | 133 | + | NT |
| ras | 141 | NT | + |
|  | 142 | + | + |
|  | 143 | NT | + |
|  | 144 | NT | NT |
|  | 145 | NT | + |
|  | 146 | + | NT |
|  | 147 | + | NT |
| bas | 149 | + | NT |
| myc | 151 | NT | + |
|  | 152 | + | + |
|  | 153 | NT | + |
|  | 154 | NT | NT |
|  | 155 | + | + |
|  | 156 | NT | NT |
|  | 157 | NT | + |
| mos | 16 | 1NT | + |
|  | 162 | NT | + |
|  | 163 | NT | + |
|  | 164 | + | NT |
|  | 165 | + | NT |
| erb-B | 171 | + | + |
|  | 172 | + | NT |
|  | 173 | + | + |
| src | 201 | + | NT |
|  | 202 | + | + |
|  | 203 | + | NT |
| fgr | 211 | NT | NT |
|  | 213 | + | NT |
| int-1 | 221 | NT | NT |
|  | 222 | + | NT |
| yes | 240 | + | NT |
|  | 241 | + | NT |
| mil | 250 | + | NT |
| raf | 251 | + | NT |
| fms | 290 | + | NT |
|  | 292 | + | NT |
| abl | 310 | + | NT |
|  | 311 | + | NT |
|  | 312 | + | NT |
| ros | 360 | + | NT |
|  | 361 | + | NT |
| fos | 411 | + | NT |
|  | 413 | + | NT |
|  | 416 | + | NT |
| TGF-alpha | 421 | + | NT |
| erb-A | 461 | + | NT |
|  | 462 | + | NT |

[1]Binding of receptor molecules to oncoproteins in Western blot analyses. Plus signs (+) indicate that binding was shown. NT = not tested.
[2]Polypep. No. = polypeptide number from Table 1.
[3]Binding of a monoclonal receptor molecules to an oncoprotein.
[4]Binding of oligoclonal anti-polypeptide serum to an oncoprotein.

The polypeptides useful for inducing the production of oligoclonal receptors, and ultimately for production of monoclonal receptors, are preferably linked to a carrier molecule, as discussed herein wherein polypeptides linked to KLH have been utilized throughout as illustrative polypeptide-carrier conjugates. For polypeptides that contain fewer than about 35 amino acid residues, it is preferable to use a carrier for the purpose of inducing the production of oligoclonal and monoclonal receptors. Polypeptides containing about 35 to about 40 amino acid residues may be used alone, without linkage to a carrier, to induce receptor production, although it is still preferable to utilize a carrier for producing those receptors. Thus, the receptors may be induced by or raised to a polypeptide alone, or linked to a carrier.

B. Immunization Binding Studies

As noted several times, the polypeptides utilized in raising oligoclonal antibodies and hybridomas that secrete monoclonal antibodies are themselves immunogenic and antigenic, and those properties provide criteria for identifying useful polypeptides for hybridoma preparation. The discussion below relates to studies with oligoclonal antibody (receptor) containing antisera induced by or raised to polypeptides used in the preparation of hybridomas that secrete monoclonal receptors (antibodies) to oncoproteins encoded by the ras, sis erb-B and myb oncogenes. As will be described, the sis-related polypeptide induces production of oligoclonal receptors that bind not only to the polypeptide, but also to a corresponding oncoprotein, human platelet-derived growth factor (PDGF). The oligoclonal antibodies so prepared exhibited the before described 50 percent binding titer to the immunizing polypeptide, thereby indicating that monoclonal antibodies (receptors) of this invention may also be prepared by fusion of the antibody-producing splenocytes with cells of suitable myeloma line.

PDGF isolated from platelets consists of two chains that are approximately sixty percent homologous at the amino-terminal end. One of those chains (PDGF-2) is virtually identical to a portion of the simian sarcoma virus (v-sis) gene product (p28$^{sis}$). Sequencing of the human c-sis and v-sis terminate at the same position and the PDGF-2 molecule originates from a larger precursor which has extensive homology with p28$^{sis}$. The homology between p28$^{sis}$ and PDGF-2 begins at amino acid residue 67 of p28$^{sis}$ and the amino-terminus of PDGF-2, and has recently been extended to the predicted carboxy-terminus of p28$^{sis}$ via the isolation and sequencing of a human c-sis clone. Josephs et al., *Science*, 223, 487–491 (1984).

p28$^{sis}$ is rapidly cleaved to generate p20$^{sis}$ which presumably has the same amino terminus as PDGF-2. Within the region coding for p20$^{sis}$ and PDGF-2 there are eight amino acid changes that can be placed into three regions. The two changes near the amino-terminus are conservative, five changes are clustered near the center of the molecule, and one change is located in the carboxyl-terminal portion.

Two exemplary polypeptides were prepared. The first, denominated polypeptide number 113 also referred to as polypeptide (c), corresponds in amino acid residue sequence to residues 139 through 155 of the predicted sequence of the simian sarcoma virus transforming protein denominated p28$^{sis}$. Devare et al., *Proc. Natl. Acad. Sci. USA*, 80, 731–735 (1983). The sequence of polypeptide (c) also corresponds to the sequence of positions 73 through 89 from the amino-terminus of the protein chain denominated PDGF-2 of human platelet-derived growth factor, as noted before. The second, denominated polypeptide number 131 also referred to as polypeptide (d), corresponds in amino acid residue sequence to residues 2 through 18 of the predicted sequence of the transforming protein of the avian myeloblastosis virus (v-myb) oncoprotein. Rushlow et al., *Science*, 216, 1421–1423 (1982). The amino acid residue sequence of polypeptides (c) and (d) are shown below, from left to right and in the direction from amino-terminus to carboxy-terminus:

polypeptide (c) RKIEIVRKKPIFKKATV;
polypeptide (d) RRKVEQEGYPQESSKAG.

Each of the polypeptides was synthesized and bound to KLH using a Cys residue of their carboxy-termini (not shown in the above formulas), and each resulting conjugate was then used to immunize mice as discussed generally in the Materials and Methods section. As can be seen from an examination of FIG. 4, sera raised to polypeptide (c) contained oligoclonal receptors that bind to polypeptide as well as to KLH, and sera raised to polypeptide (d) contained oligoclonal receptors that bind to polypeptide (d) and to KLH. Neither serum contained receptors that cross-react and bind to the polypeptide not used to raise them.

Extracts from outdated human platelets were used to obtain partially purified samples of PDGF. As already noted, PDGF is an oncoprotein having an apparent molecular weight of about 30K daltons that can be reductively cleaved into two high molecular weight polypeptides of similar apparent molecular weights, and designated PDGF-1 and -2.

FIG. 5 shows the results of Western blot analysis of PDGF using the oligoclonal receptor-containing antisera raised to polypeptides (c) and (d), as is discussed in more detail in the description of that figure; the antiserum raised to polypeptide (d) being used as a negative control. As can be seen from an examination of FIG. 5; the oligoclonal receptor-containing serum raised to the sis-related polypeptide, polypeptide (c), bound to three proteinaceous moieties (lane 2). One of those moieties has an apparent molecular weight of about 30K daltons and two of about 16–18K daltons each. Lane 4 also illustrates binding by oligoclonal receptors contained in the anti-sis related polypeptide serum. As expected, only non-specific binding was shown by oligoclonal receptors raised to the myb-related polypeptide, polypeptide (d), (lanes and 5).

Presuming that the amino acid residue sequence of PDGF-1 and -2 are collinear with the sequence of p28$^{sis}$, the amino acid residue sequence of the polypeptide (c) corresponds to positions 67 through 83, and 73 through 89 of PDGF-1 and -2, respectively. The amino acid residue sequence of residues 73 through 80 of PDGF 2 has been determined [Doolittle et al., *Science*, 221, 275–277 (1983)] and all of the those residues are identical to the first (amino-terminal) eight residues of polypeptide (c). In addition, a polypeptide from PDGF and corresponding to residues 147 through 155 of the p28$^{sis}$ oncoprotein has been sequenced [Waterfield, *Nature*, 304, 35–39 (1983)], and of the nine residues so far identified, all are identical to the corresponding residues of polypeptide (c). Thus, sixteen of the seventeen residues of polypeptide (c) are identical to and in the same sequence as residues in both PDGF, derived from humans, and p28$^{sis}$ derived from a line of retrovirus-transformed cells.

The above results thus illustrate the immunogenicity and antigenicity of two additional polypeptides useful for immunizations leading to the preparation of hybridomas that secrete monoclonal receptors of this invention. Those results also show that the oligoclonal receptors raised to polypeptide (c) also bind to an oncoprotein; i.e., PDGF, PDGF-1 and PDGF-2.

Additional synthetic polypeptides representing various regions of both PDGF sequences were made. The amino-termini of PDGF-1 and PDGF-2, as well as the central and carboxy-terminal portion of PDGF-2 were synthesized, conjugated to the immunogenic carrier keyhole limpet hemocyanin (KLH), and injected into mice to induce production of oligoclonal receptor-containing antisera that exhibited the before-described 50 percent binding titer.

The polypeptide representing the unique region of PDGF-2 contains the first 18 amino acid residues of this sequence and will be called PDGF-2(1–18) (polypeptide number 112), wherein the parenthesized numerals indicate the amino acid residues of the corresponding molecule numbered from amino-terminus. The unique region of PDGF-1 is represented by a polypeptide PDGF-1(1–12) also referred to as polypeptide number 111, that contains the first 12 amino acids of that sequence. Six of those 12 amino acids are shared with PDGF-2 but only three are consecutive, as noted before. The third polypeptide, PDGF-2(73–89) is also referred to herein as polypeptide (c) and polypeptide number 113. It represents the predicted amino acid residues 139–155 of p28$^{sis}$ and contains an additional cysteine at its carboxy-terminus for coupling purposes. This polypeptide when coupled to KLH induced production of antibodies that recognize the reduced subunits of purified PDGF, proteins of MW 31,000, 30,000, 21,000 and 18,000–14,000 in a platelet extract, and a 56K dalton protein in SSV-infected marmoset cells. The fourth polypeptide, PDGF-2(126–145), was also predicted by the v sis sequence (residues 191–210 of p28$^{sis}$ also referred to as polypeptide 114). Amino acid sequences of these polypeptides have been illustrated hereinbefore.

To analyze the specificity of the oligoclonal receptor-containing antisera generated against these synthetic polypeptide conjugates, PDGF was probed with these antisera. Purified PDGF was reduced and electrophoresed into a polyacrylamide gel, and then onto nitrocellulose (FIG. 6, lanes A–F) using a Western blot procedure. In lanes A and B, two antisera directed against PDGF-1(1–12) immunoreacted with a protein of approximately 18,000 daltons. Sequence analysis of purified PDGF indicates the majority of the PDGF-1 chain migrates at this position [Antonaides, et al., *Science*, 220, 963–965 (1983)]. The weakness of the reactivity with these antisera suggests the amino-terminal end of PDGF-1 may not be readily accessible for antibody binding.

In contrast, antiserum against the amino-terminus of PDGF-2 (1–18) (lane C) readily detected a protein migrating at about 18,000 and 14,000 daltons, consistent with sequence analysis of PDGF-2 (Antonaides et al., supra.).

The antisera induced by PDGF-2(73–89) produced the same activities (lanes D, E) as seen in lane C. In contrast, antisera against PDGF-2(126–145) did not have detectable activity against purified PDGF.

Since the sequence of the PDGF-2(126–145) polypeptide differs from c-PDGF at position 145 (Josephs, et al., supra), it is possible that this amino acid residue change is contained within the epitopic site. This is unlikely because the polypeptide is 20 amino acid residues long and the change is only on the carboxy-terminal position that is used to couple the polypeptide to the KLH carrier protein. The lack of activity is thus not due to generation of oncopolypeptide specific antibodies because this antiserum reacts with cell-derived PDGF-like molecules. The 14,000 to 18,000 dalton size of the detected PDGF in purified preparations suggest that most of this material is missing the carboxy-terminal end of the predicted sequence of p28$^{sis}$, which would remove all or part of the PDGF antigenic site recognized by this antiserum.

In order to determine if PDGF-like proteins might also be synthesized in other transformed cell lines, extracts were made and immunoreacted with various oligoclonal receptor containing antisera against PDGF-related polypeptides. In FIG. 7, the SSV-transformed NIH 3T3 cells were probed with an oligoclonal receptor-containing antiserum induced by PDGF-1(1–12) (lanes A–C, F–H and K–M) and by PDGF-2(73–89) (lanes D, E, I, J, N and O). Of the two sera against PDGF-2(73–89) (FIG. 6, lanes D and E), the serum used in FIG. 6, lane D produced a somewhat weaker activity with purified PDGF. However, as seen in lane D of FIG. 7, a strong reactivity with a protein of approximately 70,000 daltons was observed that was blocked by preincubation with the immunizing polypeptide, PDGF-2(73–89) (lane E), but was not blocked by preincubation of the antiserum with PDGF-1(1–12).

Thus, the specific reactivity with these oncoproteins by both antisera demonstrates that this is not a fortuitous cross-reactivity with a small region of PDGF, but that this molecule contains sequences homologous to at least the amino-terminus of PDGF-1 and the central region of PDGF-2. The amounts of p28$^{sis}$ and p20$^{sis}$ were below the level of detection with this anti-PDGF-2(73–89) serum. Similar results were obtained with additional antisera, although overexposure did occasionally show a 20,000 dalton band was specifically detected (data not shown).

Analysis of extracts of two other unrelated transformed cells with these antisera gave similar results. The TRD1 cell line is a spontaneously transformed Balb/3T3 cell line [Bowen-Pope et al., *Proc. Natl. Acad. Sci. USA*, 81, 2396–2400 (1984)]. This line also expresses a 70,000 dalton protein as well as a more immunologically related protein of approximately 100,000 daltons (FIG. 7, lanes G–I). A third cell line, MSTF, and a mink lung line (CCL64) productively infected with FeLV-B and the Snyder-Theilen strain of FeSV, also expresses the same size protein FIG. 7, lanes K–O.

In addition to the 70,000 dalton oncoprotein, an oligoclonal receptor-containing antiserum against PDGF-1(1–12) detected proteins of approximately 53,000 daltons (data not shown). These proteins are not serum contaminants because they are detected in extracts of cells that have been grown for one month in the absence of serum and are found in serum free media conditioned by the TRD1 cell lines. All cell lines studied contain these two PDGF-like proteins. (See also discussion of FIG. 11 in "Brief Description of Figures").

The expression of PDGF-like molecules in a broad spectrum of cells, including cells that are not oncogenically transformed (normal diploid rat smooth muscle and human lung ribroblasts), indicates that other processes are involved in transformation. Although all of the cell lines contained 70,000 and 53,000 dalton proteins detected with oligoclonal receptor-containing antisera induced by PDGF-1(1–12), the cells were quite heterogeneous with regard to size and intensity of other proteins detected with antisera directed against determinants predicted by the sequence of the PDGF-2 region (data not shown). The nature of these differences is presently unknown.

In a similar manner, each of the four immunogenic polypeptides, denominated (e–h) below, may be used to induce oligoclonal receptors that bind to those immunogenic polypeptides used to induce their production as well as to each of two oncoproteins encoded by the ras oncogene. The sequences of those four ras-related polypeptides, in the direction from left to right and from amino-terminus to carboxy-terminus, are represented by the formulas:

| polypeptide e KLVVVGARGVGK (polypeptide 141); |
| polypeptide f KLVVVGASGVGK (polypeptide 143); |
| polypeptide g KLVVVGAVGVGK (polypeptide 144); |
| polypeptide h KLVVVGAGGVGK (polypeptide 145); | or by the combined formula:

| polypeptide (e–h) |
| KLVVVGAR(S,V,G)GVGK; | wherein the amino acid residues in parentheses are each an alternative to the immediately preceding amino acid residue in the formula. The oligoclonal receptors so prepared have a 50 percent binding titer dilution of more than 1:400 after two immunizations, as described before, in about a one month period. Additionally, each ras-related oligoclonal receptor induced by polypeptides (e), (f) and (h) have been shown to bind to an oncoprotein present in lysed cell extracts from (a) human T24 bladder carcinoma cells and also (b) Harvey murine sarcoma virus-infected mouse 3T3 cells (data not shown).

As is seen in FIG. 12, each of the two immunogenic polypeptides denominated below (k and l) may be used to induce oligoclonal receptors that bind to those immunogenic polypeptides used to induce their production as well as to each of two oncoproteins encoded by the vfes$^{ST}$ oncogene. The sequence of the two v-fes-related polypeptides, in the direction from left to right and from amino-terminus to carboxy-terminus are represented by the formulae:

| polypeptide k LEMQCWAYEPGQRPSF |
| (polypeptide 127); |
| polypeptide l IGRGNFGEVFSG |
| (polypeptide 121). |

The oligoclonal receptors induced by polypeptides (k) and (l) have been shown to bind to an oncoprotein present in supernatant from cells of human T24 bladder carcinoma and a spontaneously transformed mouse 3T3 cell line (Lanes A and C).

Monoclonal receptors secreted by hybridomas ATCC HB 8952, HB 8954 and HB 8955 raised to polypeptide 121 have been shown to immunoreact with one or more proteins obtained from tumors of the breast, rectum, stomach and endometrium. Reactivity of a monoclonal receptor raised to polypeptide 127 (hybridoma 127–42C11) with proteins in urine samples of pregnant mothers is discussed hereinafter.

As shown in FIG. 13, a protein related to the ras oncogene was detected by a monoclonal antibody (from hybridoma ATCC HB 8679) raised to aras synthetic peptide corresponding to positions 96–118 of v-ras$^{Ha}$ (polypeptide 142). The protein is detected in lane A and blocked by preincubation with the immunizing peptide (lane B). Thus, the preincubation with the immunizing polypeptide blocked the strongly reactive oncoprotein.

The use of monoclonal receptors of this invention such as those raised to the sis-(PDGF) related polypeptide (c), or to the fes-related polypeptides (a), (b) (k) or (l), or to the ras-related polypeptides (e–h) or to the other oncoprotein-related polypeptides disclosed herein in the affinity sorbants described below provides a convenient and less arduous means for preparing naturally occurring proteinaceous materials that are otherwise difficult to obtain in purified form such as PDGF. Thus, rather than having to go through the long procedure to obtain purified PDGF, discussed hereinafter, one may, for example, merely lyse the cells, centrifuge, pour the supernatant through an affinity sorbant column containing bound anti-polypeptide (c) receptor, and elute the purified protein after dissociating the formed, reversible ligand complex. While some additional proteinaceous material may be non-specifically bound to the affinity sorbant column, the isolation of purified proteins that are otherwise difficult to obtain in such form is greatly enhanced using such sorbants.

The antisera to the conserved sequences described above react with proteins in a wide variety of transformed cell lines. The antisera readily detected oncogene-related proteins that were five-to-fifty-fold more concentrated in the urine of cancer patients and pregnant women than in normal controls. Unique patterns of expression were detected in various malignancies and during different gestational stages of pregnancy.

Anti-peptide antibodies are particularly suited for detecting proteins immunologically related to sequenced oncogenes [Wong et al., Proc. Natl. Acad. Sci. USA, 78, 7412–7416 (1981)]. Since they are sequence specific, anti-peptide antibodies can be directed toward highly conserved regions of proteins to maximize the probability of identifying related molecules which may have similar functions. Because immune recognition of proteins by anti-peptide antibodies need not be highly dependent upon antigen conformation, one can identify proteins that are not detected by anti-protein antibodies, the bulk of which are directed against determinants unique to the folded protein. Finally, the binding of anti-peptide antibodies is relatively insensitive to alteration or fragmentation of the target antigen such as might occur in bodily fluids or secretions.

In Tables 1 and 3, the synthetic peptides used to generate the antibodies are enumerated and listed together with related sequences of other oncogenes. An exemplary ras polypeptide 142 is the v-ras$^{Ha}$ sequence located at 37–59 amino acids downstream from the threonine residue autophosphorylated by p21 encoded by v-ras$^{Ha}$ or v-ras$^{Ki}$. The sequence is identical in H-RAS and N-RAS, and differs from K-RAS by one conservative amino acid change. Capon et al. Nature 304, 507 (1983). The sequence of PDGF-2 used to generate the sis monoclonal antibodies is located at the amino-terminus of the chain (polypeptide 112) and is homologous to the first 12 amino-acids of the other chain (PDGF-1) of platelet-derived growth factor. The fes peptide (polypeptide 127) constitutes residues 744–759 of the 85,000 dalton fusion protein of v-fes-st (positions 927–942 of v-fes-GA) and is 79–94 amino acids downstream from the major tyrosine phosphorylation site. The peptides used for this study were selected because they represent highly conserved regions of the respective oncogene families.

The antisera to these conserved sequences react with proteins in a wide variety of transformed cell lines. The reactivity of the three antisera with proteins of a mink lung line transformed by feline sarcoma virus are shown in FIG. 14. Antibodies against the sis-peptide detect a 20,000 dalton protein in SSV-transformed NRK cells as well as a sis-related protein of approximately 56,000 daltons (p56$^{sis}$) in the mink lung line (lane 1). Antibodies against the ras peptide detect a major protein of approximately 21,000 daltons (p21$^{ras}$) and a minor protein of approximately 30,000 daltons in the cell extract (lane 2). The antiserum against the fes protein detects the 85,000 dalton gag-fes fusion protein (pp85-$^{gag-ges}$) as well as a 40,000 dalton protein (p40$^{fes}$, lane 3).

In FIG. 15, the reactivity of these antisera with urinary proteins from a variety of patients is demonstrated. The sis antisera detect proteins of 56,000, 31,000 and 25,000 daltons in urine concentrates (Panel A).

The antibody binding to all three proteins is blocked by prior incubation with the sis peptide (Panel B) but not by incubation with the ras peptide (Panel A). The concentrations of the detected proteins are five to fifty fold higher than normal individuals (see below). All urines studied contained the three sis-related proteins except for the sample from the patient with lymphoma which is missing the 56,000 dalton protein (lane 4).

The somewhat faster mobilities of p56$^{sis}$ (Panel A, lanes 1 and 2) in the urine from the donors with multiple myeloma and gastric cancer is due to excess albumin in these samples, whereas the distortion of the lower molecular weight proteins in lane 1 are due to excessive amounts of antibody light chain.

In Panel C the various ras-related proteins detected in urine samples are displayed. Proteins are approximately 100,000 and 55,000 daltons are detected (Panel C, lane 2–4). Again, the specificity of the antiserum was demonstrated by blocking the activity by preincubation with the ras peptide (Panel D) but not by preincubation with the sis peptide (Panel C).

The 55,000 dalton ras-related protein is different from the 56,000 dalton sis-related protein (see below) and displays different reactivity patterns in each sample. The protein is not detectable in Panel C, lane 1 (gastric cancer) while four bands of almost equal intensity are seen in lane 2 (38 weeks pregnant).

A strongly reactive doublet is visualized in lane 3 when urine from a patient (donor) with breast cancer was probed. A minor band at approximately 35,000 daltons is associated with high concentrations of the 55,000 dalton protein. In lane 4, a single 55,000 dalton band was detected.

Proteins of approximately 21,000 daltons were detected in all 4 lanes of Panel C. These smaller proteins were present at similar concentrations although the mobility of the protein in Panel C, lane 1 is slightly slower. This altered mobility may be significant because of the effect of changes at amino acid residue position 12 on the electrophoretic mobility of ras encoded proteins. The binding detected at 25,000 daltons is difficult to interpret due to comigration with antibody light chain.

In Panel E, the 35,000 and 40,000 dalton fes-related proteins are shown. The binding was blocked by preincubation with the immunizing fes peptide (panel E, lane 1) but not incubation with the ras peptide or peptides representing the homologous sequences in erb B or abl proteins (Panel E, lanes 2–4).

In summary, the 3 antisera described above specifically detect 8 different proteins in urine, 3 sis-related proteins (p56$^{sis}$, p31$^{sis}$, and p25$^{sis}$), 3 ras-related proteins (p100$^{ras}$, p55$^{ras}$, and p21$^{ras}$) and 2 fes-related proteins (p40$^{fes}$, p35$^{fes}$).

In FIG. 23, the frequencies of detection of oncogene-related proteins in urine samples of the 51 control (normal; free from diagnosed neoplastic disease) or 189 urine samples from patients (donors) with a variety of malignancies are listed. Similar frequencies in 260 urine samples from pregnant women are shown in FIG. 24. The amount of oncogene-related proteins in the urine was estimated using immunoblots, and was placed into 1 of four categories: undetectable, detectable, 5–15-fold elevated, and greater than 15-fold elevated.

The types of malignancies in which more than 10 samples were tested are listed individually. The remaining types are listed as a composite.

p21$^{ras}$ was detected in approximately 70% of all tumor samples. However, similar frequencies were found in apparently normal individuals. In contrast to the elevated levels of the ras- and fes-related proteins found in urine of breast cancer patients, bladder and prostate cancer patients frequently secrete elevated levels of the 56,00 dalton sis-related protein. This protein was detected in the absence of the ras- and fes-related proteins described above (FIG. 15, lanes 1, 2, Panels A–C). In addition to the 56,000 dalton sis-related protein, these patients frequently had elevated levels of the 31,000 and/or 25,000 sis-related proteins. In further contrast, urine from a patient with a benign prostate nodule did not contain elevated levels of these oncogene-related proteins (FIG. 18, lane 3, Panels A–C).

High levels of the smaller proteins were also found frequently in urine from patients with lung and cervical cancer as well as non-Hodgkins lymphomas (see FIG. 23). In these latter patients, the elevated 31,000 and/or 25,000 sis-related proteins were found in the absence of the 56,000 dalton protein (FIG. 5, lane 4, Panel A–B).

Thus, in the urine samples from cancer patients three unusual patterns have been observed. A subset of the breast cancer patients have elevated levels of p55$^{ras}$ in conjunction with p40$^{fes}$ and/or p35$^{fes}$. Patients with bladder and prostate cancer excrete increased amounts of all three sis-related proteins in the absence of p55$^{ras}$, p40$^{fes}$, and p35$^{fes}$. Finally, a subset of lung cancer and lymphoma patients excreted elevated levels of only the lower molecular weight sizes the sis-related proteins. As can be seen from FIGS. 15–18 as well as FIG. 23, patterns of expression correlate with disease states better than excretion of high levels of a single oncogene-related protein. In apparently normal individuals, elevated levels of these proteins are rarely detected.

The proteins described herein are immunologically related to oncogene proteins based upon the highly specific reactivity of the various anti-peptide antisera. However, of the eight proteins described, only two (p21$^{ras}$ and p31$^{sis}$) represent oncogene-encoded whole proteins.

The p21$^{ras}$ protein has GTP binding activity. Thus, p21$^{ras}$ is intimately involved with cell division and therefore it is not surprising that the protein is readily detected in most urine samples.

Similarly, elevated levels of transcripts specific for H-ras or K-ras have been detected in a wide variety of malignancies as is shown herein. Furthermore, antisera to ras-related products have also detected elevated expression in tumor tissues. Here, the most striking elevation of this protein was found in the urine of malignancies.

p31$^{sis}$ protein, which is one of the chains of the platelet-derived growth factor (PDGF), was also detected. Although PDGF-1 chain is only 18,000 daltons when isolated from platelets, comparison of the human c-sis sequence with v-sis indicates the 18,000 dalton protein originates from a larger precursor protein. Indeed, analysis of a partially purified platelet extract reveals a protein of approximately 31,000 daltons. Since PDGF has potent mitogenic activity and is released from platelets at the site of tissue injury, one of the physiological functions of PDGF is thought to be wound healing. In addition, PDGF-like material is secreted from a number of transformed cell lines and secretion appears to be developmentally regulated in smooth muscle cells. Thus, p31$^{sis}$ like p21$^{ras}$ may be physiologically important, and it is not surprising that it is present in the urine in normal and abnormal states.

In addition to the oncogene encoded proteins of expected molecular size, additional proteins were detected in this study. It is not likely that their presence is due to spurious cross-reactivities since they are uniquely present in certain cancers as well as during pregnancy. Further, the reaction of the antibodies with these proteins was inhibited specifically with the appropriate synthetic immunogens. Since the peptides used as immunogens represent conserved sequences among oncogene families, these additional proteins may represent members of these gene families. The expression of these genes may come under coordinate control during neoplasia or pregnancy. Regardless of the origin of these proteins, the fact that they are uniquely expressed during neoplasia and pregnancy makes them important markers.

III. DIAGNOSTIC SYSTEMS AND METHODS

A diagnostic system, preferably in kit form, comprises yet another embodiment of this invention. This system is useful for assaying for the presence of an oncoprotein ligand by the formation of an immune reaction. This system includes at least one package that contains biologically active monoclonal receptor molecules of this invention. Thus, the receptor binds to (a) a polypeptide containing about 7 to about 40, and preferably about 10 to about 30, amino acid residues in an amino acid residue sequence that corresponds to a portion of the amino acid residue sequence of an oncoprotein ligand encoded by a gene of a retrovirus, and (b) the oncoprotein ligand encoded by a retroviral gene.

When a predetermined amount of monoclonal receptor molecules is admixed with a predetermine amount of an aqueous composition containing an oncoprotein ligand, an immunological reaction occurs that forms a complex between the receptor and the ligand (antibody and antigen). Exemplary aqueous compositions containing an oncoprotein include, without limitation, cell lysates, serum, plasma, urine and amniotic fluid.

In addition, it is particularly valuable to utilize a screening with antisera to more than one oncogene-related translation product. Thus, assay methods set forth herein can be performed on a group of body fluid sample antiquots taken from a single donor to yield accurate information regarding a neoplastic state, gestational stage or the like.

Admixture between receptor and ligand occurs in an aqueous composition. However, either the receptor or ligand can be substantially dry and water-free prior to that admixture. Thus, a solution of the receptor in hybridoma supernatant, ascites fluid or buffer can be admixed with an aqueous cell extract to admix the reagents from two aqueous compositions; the receptor can be coated on the walls of a microliter plate and then admixed with a cell extract or serum containing the ligand; or the ligand can be coated on microliter plate walls, on a nitrocellulose sheet after transfer from an acrylamide gel or the like, or can be present in a tissue section, and hybridoma supernatant, ascites fluid or a buffer solution containing the receptor admixed therewith.

The use of exemplary diagnostic systems and methods of this invention is illustrated in the descriptions of the Figures. There, oncoprotein ligands coated onto nitrocellulose and then admixed with a receptor of this invention are discussed in relation to FIGS. 1, 2, 5–8, and 11–14, while a cell extract incubated with hybridoma supernatant to form an immunological complex is discussed regarding FIG. 3. Oncoproteins from urine samples are discussed in FIG. 9, 10 and 15–19.

Receptors are utilized along with an "indicating group" or a "label". The indicating group or label is utilized in conjunction with the receptor as a means for determining whether an immune reaction has taken place and an immunological complex has formed, and in some instances for determining the extent of such a reaction.

The indicating group may be a single atom as in the case of radioactive elements such as iodine 125 or 131, hydrogen 3, sulfur 35, carbon 14, or NMR-active elements such as fluorine 19 or nitrogen 15. The indicating group may also be a molecule such as a fluorescent dye like fluorescein, rhodamine B, or an enzyme, like horseradish peroxidase (HRP) or glucose oxidase, or the like.

The indicating group may be bonded to the receptor as where an antibody is labeled with $^{125}$I. The indicating group may also constitute all or a portion of a separate molecule or atom that reacts with the receptor molecule such as HRP-linked receptor was raised in a mouse, or where a radioactive element such as $^{125}$I is bonded to protein A obtained from *Staphylococcus aureus*.

Where the principal indicating group is an enzyme such as HRP or glucose oxidase, additional reagents are required to visualize the fact that an immune reaction has occurred and the receptor-ligand complex has formed. Such additional reagents for HRP include hydrogen peroxide and an oxidation dye precursor such as diaminobenzidine. Additional reagents useful with glucose oxidase include ABTS dye, glucose and HRP.

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

An indicating group or label is preferably supplied along with the receptor and may be packaged therewith or packaged separately. Additional reagents such as hydrogen peroxide and diaminobenzidine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

The diagnostic system may also include a solid matrix that may be 96 well microliter plates sold under the designation Immulon II (Dynatech, Alexandria, Va.). The microliter strip or plate is made of a clear plastic material, preferably polyvinyl chloride or polystyrene. Alternative solid matrices for use in the diagnostic system and method of this invention include polystyrene beads, about 1 micron to about 5 millimeters in diameter, available from Abbott Laboratories, North Chicago, Ill.; polystyrene tubes, sticks or paddles of any convenient size; and polystyrene latex whose polystyrene particles are of a size of about 1 micron and can be centrifugally separated from the latex.

The solid matrix may also be made of a variety of materials such as cross-linked dextran, e.g. Sephadex G-25, -50, -100, -200, and the like available from Pharmacia Fine Chemicals of Piscataway, N.J., agarose and cross-linked agarose, e.g., Sepharose-6B, CL-6B, 4B CL46 and the like also available from Pharmacia Fine Chemicals.

The diagnostic system may further include a standard against which to compare the assay results and various buffers in dry or liquid form for, inter alia, washing microliter plate walls, diluting the sample, diluting the labeled reagent, or the like.

An assay method for the presence of an oncoprotein ligand in a body sample from a warm-blooded animal constitutes another aspect of the present invention. In accordance with the general assay method, a monoclonal receptor of this invention is admixed in an aqueous composition that contains the sample to be assayed for the presence of an oncoprotein ligand. Preferably, the monoclonal receptor and body sample are utilized in predetermined amounts. The admixture so prepared is maintained for a period of time sufficient for an immunoreaction to occur between the receptor and ligand and an immunocomplex (reaction product or immunoreactant) to form. The presence of an immuno-complex is then determined, and its presence indicates the presence of the oncoprotein ligand in the assayed sample. The presence of an immunocomplex is determined using the beforedescribed labels or by other means well known in immunochemistry for determining the presence of the antibody-antigen complexes.

Specific assay methods are also contemplated. Each of those specific methods utilizes the above three steps, but the specifics of those assay methods differ slightly from one another.

Solid phase assays wherein the sample to be assayed is affixed to a solid phase matrix such as a microtiterplate test well or a nitrocellulose sheet to form a solid support are particularly preferred. In such instances, admixture of the sample to be assayed and the monoclonal receptor forms a solid-liquid phase admixture. The solid and liquid phases are separated after the before-described maintenance period, and the presence of a liquid-receptor complex is determined by the presence of receptor bound to the solid support. The relative amount of bound receptor can be determined in many assays, thereby also providing a determination of the amount of oncoprotein ligand that was present in the sample assayed.

A receptor molecule of this invention can also be affixed to the solid matrix to form a solid support. In that instance, the sample to be assayed is admixed to form a solid-liquid phase admixture, the admixture is maintained as described before, and the presence of an immunocomplex and oncoprotein in the assayed sample are determined by admixture of a predetermined amount of a labeled ligand such as a polypeptide or oncoprotein that is bound by the affixed receptor molecule. Thus, the presence of a complex formed between the receptor and oncoprotein of the sample provides an amount of labeled ligand binding that is less than a known, control amount that is exhibited when the sample is free of oncoprotein being assayed. The relative amount of oncoprotein in the sample can be determined by using an excess of the receptor and measuring the lessened binding of the labeled ligand.

A polypeptide or oncoprotein ligand bound by a receptor molecule of this invention can also be affixed to a solid matrix to form the solid support antigen. A known, excess amount of receptor molecules of this invention is admixed with the sample to be assayed to form a liquid admixture. The liquid admixture so formed is maintained for a period of time sufficient to form an immunocomplex reaction product, and is thereafter admixed with the solid support to form a solid-liquid phase admixture. That admixture is maintained for a period sufficient for the excess, unreacted receptor molecules present to immunoreact and form a complex with the solid phase support antigen. The amount of that complex that is formed is determined, after separation of the solid and liquid phases, using a previously described technique. This method can provide a determination as to the presence of oncoprotein in the sample, and also as to its relative amount, where predetermined amounts of receptor and solid phase ligand are used.

IV. DIFFERENTIAL ASSAY

Liquid body samples can be screened with antisera to more than one oncogene-encoded protein. The screening can be systematically accomplished in accordance with the assay methods of this invention. The screening of samples with more than one antiserum provides a pattern of oncoproteins present in the sample assayed.

In breast cancer patients, $p55^{ras}$ and $p40^{fes}$ are found to be elevated (FIGS. 16 and 17) in contrast to the $p56^{sis}$ found in bladder and prostate cancer patients (FIG. 18). Also, bladder and prostate cancer patients often demonstrated elevated levels of the 31K dalton or 25K dalton sis-related proteins. In contrast, a donor with a benign prostate nodule did not demonstrate these elevated levels of protein.

High levels of the smaller proteins were also found in patients with lung and cervical cancer as well as non-Hodgkins lymphomas (See FIG. 23). In these patients, the elevated 31K dalton and/or 25K dalton sis-related proteins were found in the absence of the 56K dalton protein (See FIG. 15, lane 4, Panels A-B).

Thus, in the urine samples from cancer patients three unusual patterns have been observed. A subset of the breast cancer patients have elevated levels of $p55^{ras}$ in conjunction with $p40^{fes}$ and/or $p35^{fes}$. In contrast, patients with bladder and prostate cancer excrete increased amounts of all three sis-related proteins in the absence of $p55^{ras}$, $p40^{fes}$, and $p35^{fes}$. Finally, a subset of lung cancer and lymphoma patients excrete elevated levels of only the lower molecular weight sizes of the sis-related proteins. As can be seen from the Figures, patterns of expression correlate with diseased states better than excretion of high levels of a single oncogene-related protein. In apparently normal individuals, elevated levels of these proteins are rarely detected.

The finding of oncogene-related proteins in urine was unexpected and has not been previously reported by others. This finding provides a basis for still another method aspect of the present invention.

In accordance with this method, a sample of urine or a urine concentrate is admixed in an aqueous composition, as described before, with a receptor that immunoreacts with an oncoprotein. The admixture is maintained for a period of time sufficient for an immunocomplex to form, and the presence of an immunocomplex is determined as described before in relation to the general assay method and the before-described specific methods.

In this method, any receptor known to immunoreact with an oncoprotein can be used. Thus, the receptor molecules can be of polyclonal, oligoclonal or monoclonal origin, and can have been raised to a whole or fusion oncoprotein, or a polypeptide as described herein.

Blotting techniques such as those of the Western blots of the Figures and so-called "slot blots" wherein the sample is affixed to a nitrocellulose matrix as a solid support and where the receptor molecules in a liquid aqueous composition are admixed on the nitrocellulose sheet are preferred techniques for analysis. However, other techniques such as solid phase ELISA and radioimmunoassay (RIA) that utilize microliter plate wells as solid matrices, and dip stick methods are also useful.

V. IN UTERO FETAL SEX DETERMINATION

Five site-directed monoclonal antibody probes and one oligoclonal serum probe were used to detect oncoprotein ligands related to beta-TGF, EGF, int-1, fes, ras, and myb, in urine from newborn infants and pregnant women. A subset of the beta-TGF-related oncoprotein ligands was found exclusively in newborn female urine samples. A subset of these samples contain the fes- and ras-related proteins which were elevated in urine from breast cancer patients, discussed before. Urine samples from male and female newborn infants or pregnant women contained additional oncogene-related proteins. Two proteins (p55$^{1ras}$ and p40$^{fas}$ were elevated in urine samples from expectant mothers carrying 16–18 week female fetuses. The hybridomas and the synthetic polypeptides used to generate the antibody probes are listed in Table 4. The samples were screened using Western blot techniques as are discussed hereinafter.

TABLE 4

| Site-Directed Antibodies[1] | | |
|---|---|---|
| Oncogene/Growth Factor | Hybridoma | Polypeptide Number |
| Beta-TGF | (oligoclonal) | 1000 |
| EGF | 432-25G07 | 432 |
| int-1 | 222-35C08 | |
| | 222-33A05 | 222 |
| fes/FES | 127-42C11 | 127 |
| src | 203-07D10 | 203 |
| H-RAS/N-RAS | 142-24E05 | 142 |

TABLE 4-continued

| Site-Directed Antibodies[1] | | |
|---|---|---|
| Oncogene/Growth Factor | Hybridoma | Polypeptide Number |
| c-MYC/L-MYC | 152-06D11 | 152 |
| v-myb | 133-10F06 | 133[2] |

[1]Oncogenes growth factors, hybridoma designations and polypeptide numbers are as listed in Tables 1 and 2.
[2]This polypeptide is lacking one of the three adjacent histidines found in the Avian sequence.

Each urine sample was reduced, boiled, and applied to a polyacrylamide gel, as discussed in the Materials and Methods Section. After transfer to nitrocellulose, separate samples were probed with each of the six antisera. The results for twenty-five individuals are listed in Table 5, in which relative density values were estimated optically.

TABLE 5

PROTEIN LEVELS IN NEWBORN URINE[1]

| | FES | | | V-myb | | | | H/N-RAS | | | int-1 | | | | | Beta-TGF | | | | |
|---|---|---|---|---|---|---|---|---|---|---|---|---|---|---|---|---|---|---|---|---|
| PATIENT | 40 | 38 | 35 | 150 | 55 | 53 | 50 | 100 | 55 | 21 | 70 | 50 | 43 | 38 | 30 | 25 | 67 | 42 | 24 | 18 | 12 |
| KIM | 0 | 0 | 0 | 0 | 0 | 0 | 0 | 0 | 0 | 0 | 0 | 0 | 0 | 0 | 0 | 0 | 0 | 0 | 1 | 0 | 0 |
| IBA | 0 | 0 | 1 | 0 | 1 | 0 | 0 | 1 | 0 | 1 | 0 | 1 | 0 | 0 | 0 | 2 | 0 | 0 | 5 | 0 | 0 |
| VAL | 0 | 0 | 0 | 0 | 0 | 0 | 0 | 0 | 0 | 0 | 0 | 0 | 0 | 0 | 0 | 0 | 0 | 0 | 1 | 0 | 0 |
| CIN | 0 | 0 | 0 | 0 | 2 | 0 | 0 | 1 | 0 | 1 | 0 | 0 | 1 | 1 | 0 | 1 | 0 | 0 | 4 | 0 | 1 |
| MUN | 0 | 0 | 0 | 0 | 0 | 0 | 0 | 0 | 0 | 0 | 0 | 0 | 0 | 0 | 0 | 0 | 0 | 0 | 3 | 0 | 0 |
| ADE | 0 | 0 | 0 | 0 | 1 | 0 | 0 | 0 | 0 | 0 | 0 | 0 | 0 | 0 | 0 | 0 | 0 | 0 | 4 | 0 | 0 |
| BRO | 2 | 1 | 2 | 0 | 1 | 1 | 1 | 1 | 3 | 1 | 0 | 0 | 1 | 1 | 1 | 2 | 2 | 1 | 5 | 0 | 2 |
| IME | 2 | 2 | 2 | 1 | 0 | 0 | 1 | 1 | 3 | 2 | 0 | 1 | 0 | 0 | 0 | 2 | 2 | 0 | 5 | 3 | 0 |
| STR | 2 | 2 | 2 | 0 | 0 | 0 | 0 | 2 | 4 | 2 | 0 | 1 | 0 | 0 | 0 | 1 | 3 | 0 | 4 | 0 | 1 |
| WOL | 3 | 0 | 3 | 0 | 0 | 0 | 0 | 2 | 5 | 3 | 0 | 0 | 0 | 0 | 0 | 0 | 3 | 0 | 5 | 2 | 0 |
| SER | 2 | 1 | 2 | 2 | 3 | 0 | 2 | 0 | 2 | 2 | 0 | 3 | 1 | 1 | 2 | 3 | 1 | 0 | 3 | 0 | 1 |
| CAR | 3 | 2 | 3 | 0 | 1 | 1 | 0 | 0 | 5 | 2 | 0 | 0 | 0 | 1 | 2 | 2 | 2 | 0 | 4 | 0 | 2 |
| TOTAL POS.[2] (FEMALE) | 6 | 5 | 7 | 2 | 6 | 2 | 3 | 6 | 6 | 8 | 0 | 4 | 4 | 4 | 3 | 7 | 6 | 1 | 12 | 2 | 5 |
| HOL | 0 | 0 | 0 | 0 | 1 | 1 | 0 | 0 | 0 | 1 | 1 | 1 | 0 | 0 | 0 | 1 | 0 | 1 | 0 | 0 | 0 |
| SAN | 0 | 0 | 0 | 0 | 0 | 0 | 0 | 0 | 0 | 0 | 0 | 0 | 0 | 0 | 0 | 0 | 0 | 0 | 0 | 0 | 2 |
| CEA | 0 | 0 | 0 | 0 | 0 | 0 | 0 | 0 | 0 | 0 | 0 | 0 | 0 | 0 | 0 | 0 | 0 | 0 | 0 | 0 | 1 |
| CAR | 0 | 0 | 0 | 0 | 1 | 0 | 0 | 0 | 0 | 1 | 0 | 1 | 0 | 0 | 0 | 0 | 0 | 0 | 0 | 0 | 1 |
| PEA | 0 | 0 | 0 | 0 | 1 | 0 | 0 | 0 | 0 | 0 | 0 | 0 | 0 | 0 | 0 | 0 | 0 | 0 | 0 | 0 | 2 |
| SUM | 0 | 0 | 0 | 0 | 0 | 0 | 0 | 0 | 0 | 0 | 0 | 0 | 0 | 0 | 0 | 0 | 0 | 0 | 0 | 0 | 1 |
| MAR | 0 | 0 | 0 | 0 | 0 | 0 | 0 | 0 | 0 | 0 | 0 | 0 | 0 | 0 | 0 | 0 | 0 | 0 | 0 | 0 | 1 |
| BAT | 0 | 0 | 0 | 0 | 2 | 2 | 0 | 0 | 0 | 1 | 0 | 0 | 1 | 1 | 0 | 1 | 0 | 0 | 0 | 0 | 2 |
| MAR | 0 | 0 | 0 | 0 | 2 | 0 | 0 | 0 | 0 | 0 | 0 | 0 | 0 | 0 | 0 | 0 | 0 | 0 | 0 | 0 | 3 |
| SIM | 0 | 0 | 0 | 2 | 2 | 0 | 0 | 0 | 0 | 0 | 0 | 2 | 0 | 0 | 2 | 0 | 0 | 0 | 0 | 0 | 3 |
| BOO | 0 | 0 | 9 | 0 | 0 | 0 | 0 | 0 | 0 | 0 | 0 | 0 | 0 | 0 | 0 | 0 | 0 | 0 | 0 | 0 | 1 |
| PLE | 0 | 0 | 0 | 0 | 1 | 1 | 0 | 0 | 0 | 0 | 0 | 0 | 0 | 0 | 0 | 2 | 0 | 0 | 0 | 0 | 2 |
| DES | 0 | 0 | 0 | 0 | 4 | 0 | 0 | 0 | 0 | 1 | 0 | 0 | 0 | 0 | 1 | 1 | 0 | 0 | 0 | 0 | 2 |
| TOTAL POS.[2] (MALE) | 0 | 0 | 0 | 1 | 8 | 3 | 0 | 0 | 0 | 4 | 1 | 3 | 1 | 1 | 2 | 4 | 0 | 1 | 0 | 0 | 12 |

[1]Oncogenes growth factors, hybridoma designations and polypeptide numbers are as listed in Tables 1 and 2.
[2]This polypeptide is lacking one of the three adjacent histidines found in the Avian sequence.

TABLE 6

| PATIENT | PROTEINS IN MATERNAL URINE[1] | | | | | | | | | | | | | | |
|---|---|---|---|---|---|---|---|---|---|---|---|---|---|---|---|
| | FES | | | | V-myb | | H/N-RAS | | | | int-1 | | EGF | Beta-TGF | |
| | 150 | 45 | 40 | 35 | 60 | 45 | 100 | 55 | 23 | 21 | 52 | 25 | 150 | 24 | 12 |
| ROB | 0 | 0 | 0 | 0 | 4 | 2 | 0 | 0 | 0 | 2 | 0 | 0 | 3 | 4 | 2 |
| IME | 0 | 3 | 0 | 0 | 3 | 0 | 2 | 0 | 0 | 2 | 4 | 3 | 2 | 0 | 0 |
| GOU | 0 | 2 | 0 | 0 | 2 | 1 | 0 | 0 | 0 | 2 | 2 | 2 | 3 | 3 | 3 |
| ABB | 1 | 1 | 1 | 1 | 0 | 3 | 1 | 4 | 0 | 1 | 0 | 3 | 0 | 0 | 1 |
| GOO | 3 | 3 | 0 | 0 | 1 | 3 | 2 | 0 | 0 | 3 | 3 | 3 | 5 | 3 | 2 |
| VIC | 2 | 2 | 0 | 0 | 0 | 0 | 0 | 0 | 0 | 1 | 3 | 3 | 0 | NT | NT[3] |
| RAS | 2 | 3 | 3 | 3 | 0 | 2 | 0 | 4 | 0 | 1 | 2 | 2 | 5 | 4 | 1 |
| PER | 1 | 1 | 0 | 0 | 4 | 3 | 2 | 2 | 0 | 4 | 0 | 0 | 2 | 4 | 2 |
| MEZ | 1 | 1 | 1 | 2 | 1 | 2 | 0 | 3 | 1 | 2 | 1 | 3 | 4 | 4 | 1 |
| MST | 0 | 1 | 2 | 2 | 0 | 0 | 0 | 4 | 2 | 1 | 0 | 0 | 3 | 3 | 1 |
| BLA | 1 | 1 | 1 | 1 | 2 | 1 | 2 | 2 | 0 | 2 | 3 | 3 | 1 | NT | NT |
| TER | 2 | 2 | 2 | 2 | 3 | 1 | 2 | 3 | 0 | 2 | 1 | 3 | 3 | NT | NT |
| NIM | 2 | 2 | 1 | 1 | 3 | 3 | 1 | 3 | 0 | 2 | 4 | 3 | 4 | NT | NT |
| STR | 2 | 1 | 0 | 0 | 0 | 3 | 1 | 0 | 0 | 1 | 3 | 3 | 0 | NT | NT |
| TOTAL POS.[2] (FEMALE FETUS) | 10 | 13 | 7 | 7 | 9 | 11 | 8 | 8 | 2 | 14 | 8 | 8 | 11 | 7 | |
| DUQ | 0 | 0 | 0 | 0 | 2 | 2 | 0 | 0 | 0 | 2 | 2 | 2 | 3 | | |
| BOO | 0 | 0 | 0 | 0 | 0 | 1 | 0 | 0 | 0 | 1 | 0 | 2 | 0 | | |
| MAC | 3 | 2 | 0 | 0 | 1 | 2 | 1 | 0 | 0 | 2 | 0 | 3 | 4 | | |
| ESP | 0 | 1 | 0 | 3 | 0 | 3 | 1 | 0 | 0 | 3 | 3 | 2 | 2 | | |
| LOR | 1 | 1 | 0 | 1 | 0 | 0 | 0 | 0 | 0 | 0 | 0 | 2 | 2 | | |
| BEL | 3 | 2 | 0 | 2 | 0 | 2 | 1 | 0 | 0 | 2 | 4 | 0 | | | |
| HAR | 1 | 2 | 0 | 0 | 1 | 3 | 0 | 0 | 0 | 3 | 2 | 3 | | | |
| WAT | 0 | 2 | 0 | 0 | 1 | 2 | 1 | 0 | 0 | 2 | 2 | 2 | | | |
| TOTAL POS.[2] (MALE FETUS) | 4 | 6 | 0 | 3 | 4 | 7 | 4 | 0 | 0 | 7 | 5 | 7 | | | |

[1,2]See notes 1 and 2 of Table 5
[3]NT - Not tested.

Although several oncogene- or growth factor-related proteins were readily detected, none of the samples contained detectable levels of proteins related to EGF. However, all of the samples contained proteins reactive with the oligoclonal antiserum directed against beta-TGF. Moreover, only female samples contained detectable levels of p24/p23 beta-TGF (in the presence or absence of pl2 beta-TGF), whereas urine samples from male newborns had only pl2 beta-TGF.

Sex-associated expression of oncogene-related proteins is also shown in Table 5. A subset of the female samples contained readily detectable levels of p35$^{fes}$, p38$^{fes}$, p40$^{fes}$, and p100$^{ras}$, p55$^{ras}$. p35$^{fes}$, p40$^{fes}$, and p55$^{ras}$ had been previously detected at elevated levels in urine from a subset of breast cancer patients as well as pregnant women, as discussed before.

The patterns of oncogene-related proteins in fetal urine displayed considerable heterogeneity, although some of the proteins were uniformly detected in a sex-associated manner. To further characterize these proteins, sequential collections of concentrated maternal urine were probed.

Sequentially collected (between 16-20 weeks) from twenty-two pregnant mothers were also screened by Western blot analysis using the before-mentioned six antibody probes. The results of that screening are shown in Table 6. As can be seen, most of the proteins detected in newborn urine are also found in maternal urine. The concentration of most of the proteins remained constant during weeks 16-20, although unique, patterns were found for each individual. The differences in patterns were most easily identified by comparing proteins that were uniformly detected in the 16-20 week time period.

In addition to the proteins that were relatively constant in samples from the same individual, the concentrations of other proteins changed dramatically. For example, p24/p23 beta-TGF was detected in urine from most of the individuals. In contrast, p40$^{fes}$, and p55$^{ras}$ were detected only in urine from mothers carrying female fetuses. However, weekly urine collections from all patients with female fetuses did not contain detectable levels of these proteins.

During the one-month collection period, most of the proteins listed were detected in approximately half of the patients irrespective of the sex of the fetus. In contrast to these uniformly detected proteins, p40$^{fes}$ and p55$^{ras}$ were exclusively detected in patients carrying female fetuses. Urine from eight of the patients contained detectable levels of p55$^{ras}$ and urine from seven of those eight patients also contained detectable levels of p40$^{fes}$. The lack of detection of the sex-associated proteins in urine from all maternal and newborn patients could be due to short periods of expression. Daily collections of maternal urine during the 16-20 week period indicated the proteins were detected for less than one week.

The short periods of detection may be due to hormonal regulation of expression. Initial assays of diabetic pregnant patients receiving insulin revealed the presence of these proteins over extended periods of time (at least six weeks). Moreover, the detectability of the proteins was not dependent upon the sex of the fetus. Similarly, collections from normal patients with younger or older male fetuses exhibited the presence of p55$^{ras}$ Thus, the sex-associated proteins may be maternal proteins induced by external factors or the temporal expression of fetal genes.

The above results with urine samples from pregnant (expectant) mothers provide a means for predicting the sex of the fetus being carried. As noted before, expectant mothers carrying male fetuses did not express the p40$^{fes}$ or the p55$^{ras}$ proteins, whereas expectant mothers carrying female fetuses expressed one or both of those proteins during the 16–20-week period of their pregnancies. Some of those expectant mothers carrying female fetuses did not express either of those proteins in that time period.

Since there were no false positives for expectant mothers carrying male fetuses, the finding of an express p40$^{fes}$ and/or p55$^{ras}$ oncoprotein ligand in the urine of an expectant mother in the first 16–20-week pregnancy period provides a positive, noninvasive assay for ascertaining the presence of a female fetus in utero. The absence of an expressed p40$^{fes}$ and/or p55$^{ras}$ oncoprotein ligand in a urine sample of an expectant mother during the 16–20-week period is about 50–60 percent (7 of 14 and 8 of 14 samples, respectively) predictive that the expectant mother is carrying a male fetus.

In accordance with this method, a sample of urine from a pregnant mother in about the first 16 through 20 weeks of her pregnancy is provided, and is preferably reduced as with 2 mercaptoethanol, boiled, and, most preferably concentrated. That sample is admixed with receptor molecules that immunoreact with a polypeptide that has a formula, from left to right and in the direction from amino-terminus to carboxy-terminus, selected from the group consisting of (i) LMEQCWAYEPGQRPSF (polypeptide 12 of Table 1);

and (ii) YREQIKRVKDSDDVPMYLVGNKC (polypeptide 142 of Table 1).

The resulting admixture is maintained for a time period sufficient for the receptor molecules to immunoreact with an oncoprotein ligand in the urine. The presence of an immunoreaction is determined between those receptor molecules with an oncoprotein ligand that has a relative molecular mass in a 5–17 percent polyacrylamide gel of (i) about 40K daltons for the receptor molecules that immunoreact with polypeptide (i), above, or (ii) about 55K daltons for the receptor molecules that immunoreact with polypeptide (ii), above. The presence of a female fetus in utero.

In preferred practice, the receptor molecules utilized are monoclonal. Most preferably, the monoclonal receptor molecules are secreted by hybridomas having reference numbers 127-42Cll and 142-24E05 (HB 8679), respectively.

VI. AFFINITY SORBANTS

Affinity sorbants in which the monoclonal receptor molecules of this invention constitute the active, binding portions constitute yet another embodiment of this invention.

In this embodiment, the monoclonal receptor molecules of this invention are linked to a solid support that is chemically inert to the oncoprotein ligands to be purified by those sorbants. The phrase "chemically inert" is used herein to mean that a chemical reaction between the solid support and the oncoprotein ligands does not occur. However, physical interactions between the solid support and the oncoprotein ligands such as non-specific binding can and do occur between them, although such interactions are preferably minimized.

The solid support may be made of a variety of materials such as cross-linked dextran, e.g., Sephadex G-25, -50, -100, -200 and the like available from Pharmacia Fine Chemicals of Piscataway, N.J., agarose and cross-linked agarose, e.g., Sepharose 6B, CL6B, 4B, CL4B and the like also available from Pharmacia Fine Chemicals or Bio-Gel A-0.5M, A-1.5M, A-50M and the like available from Bio-Rad Laboratories, Richmond Calif., or polyacrylamide beads, e.g., Bio-Gel P-2, P-30, P-100, P-300 and the like also available from Bio-Rad Laboratories. Polyacrylamide beads have the lowest tendency for non-specific binding among the above supports, but also typically have a low porosity that limits their binding capacity. The agarose and cross-linked agarose materials are preferred herein and will be used illustratively as a solid support.

The agarose support is typically activated for linking cyanogen bromide. The activated support is then washed and linked to the receptor molecules without drying of the activated support. The support-linked receptor is then washed and is ready for use. Unreacted reactive groups on the support can be reacted with an amine such as ethanolamine or Tris, if desired, although those reactive groups decay quickly.

The affinity sorbant may be used in its loose state, as in a beaker or flask, or it may be confined in a column. Prior to use, it is preferable that the affinity sorbant be washed in the buffer or other aqueous medium utilized for oncoprotein purification to eliminate non-specifically bound proteins or those receptors that were unstably linked to the support.

An aqueous composition containing an oncoprotein ligand having an amino acid residue sequence corresponding to the amino acid residue sequence of the polypeptide to which the linked receptor of the affinity sorbant binds such as serum or a cell extract is provided, and then and then admixed with the affinity sorbant. That admixture forms a reversible, linked receptor-ligand complex between the linked receptor and the oncoprotein ligand.

The ligand receptor-ligand complex is then separated from the remainder of the uncomplexed aqueous composition to thereby obtain the oncoprotein in purified form linked to the affinity sorbant. When the admixture takes place in a beaker or flask, this separation can be made by filtration and washing. When the sorbant is in a column, the separation may take place by elution of the uncomplexed aqueous medium, again, preferably, followed by a washing step.

When the purified protein is desired free from the affinity sorbant, it can typically be obtained by a variety of procedures. In any of those procedures, the reversible linked receptor-ligand complex is dissociated into its component parts of support-linked receptor and oncoprotein ligand, followed by separating that ligand from the linked receptor-ligand complex is dissociated into its component parts of support-linked receptor and oncoprotein ligand, followed by separating that ligand from the linked-receptor to provide the purified oncoprotein free from the affinity sorbant.

The dissociation of the reversible complex may be effected in a number of ways. A 0.2 molar glycine hydrochloride solution at a pH value of about 2.5 is typically utilized. Alternatively, the bound ligand can be competed away from the linked receptor by admixture of the reversible complex with an excess of the immunogenic polypeptide utilized to raise the receptor. Such a competition avoids possible denaturation of the ligand. Separation of the admixed with the affinity sorbant. That admixture forms a reversible, linked receptor-ligand complex between the linked receptor and the oncoprotein ligand.

The ligand receptor-ligand complex is then separated from the remainder of the uncomplexed aqueous composition to thereby obtain the oncoprotein in purified form linked to the affinity sorbant. When the admixture takes place in a beaker or flask, this separation can be made by filtration and washing. When the sorbant is in a column, the separation may take place by elution of the uncomplexed aqueous medium, again, preferably, followed by a washing step.

When the purified protein is desired free from the affinity sorbant, it can typically be obtained by a variety of procedures. In any of those procedures, the reversible linked receptor-ligand complex is dissociated into its component parts of support-linked receptor and oncoprotein ligand, followed by separating that ligand from the linked receptor-ligand complex is dissociated into its component parts of support-linked receptor and oncoprotein ligand, followed by separating that ligand from the linked-receptor to provide the purified oncoprotein free from the affinity sorbant.

The dissociation of the reversible complex may be effected in a number of ways. A 0.2 molar glycine hydrochloride solution at a pH value of about 2.5 is typically utilized. Alternatively, the bound ligand can be competed away from the linked receptor by admixture of the reversible complex with an excess of the immunogenic polypeptide utilized to raise the receptor. Such a competition avoids possible denaturation of the ligand. Separation of the dissociated oncoprotein ligand from the affinity sorbant may be obtained as above.

The preparation of affinity sorbants and their use is broadly old. However, such materials and uses that incorporate the receptor molecules of this invention have not been heretofore available. A detailed description of affinity sorbants, their methods of preparation and use wherein the antigen is linked to the support may be found in *Antibody as a Tool*, Marchalonis and Warr eds., John Wiley & Sons, New York, pages 64–67 and 76–96 (1982).

VII. PANEL ASSAY

Panels of antibodies can be used to characterize virtually any biological sample by comparing the combination of antibody/antigen complexes formed in an unknown sample with combinations obtained from a known body sample. Tissues, urine or other body fluids may be characterized with respect to expression of oncogene and oncogene-related sequences. This expression is thus interpreted to indicate the stage of development of tissues or embryos or the presence or severity of cancers.

A panel assay involves screening a sample with more than one antibody. The sample is allowed to react with each antibody, and complexes between the antibodies and ligands found in the sample are detected. The pattern of complexes, that is, the combination of antibodies which react with ligands in the unknown, is compared to a pattern of reacting antibodies in a known sample. The more similar the combinations are, i.e., the higher the coincidence of the same antibody reacting with the same ligands in both the known and unknown sample, the more similar the samples are, i.e., the higher the likelihood that the unknown sample is at the same stage of development or has the same diseased state as the known sample.

The assay can be performed in liquid, or by use of a solid substrate, as noted supra. Herein, aliquots biological body samples were electrophoresed into a gel and transferred onto nitrocellulose which was then cut into strips. This Western-blot approach allows the same sample to be probed with a panel antibodies. By recreating the original block of nitrocellulose, the identity of specific and non-specific bands can be easily determined. For cell or tissue extracts, approximately 0.5 mg of protein was loaded per gel. For urine samples, the equivalent of 12 ml of urine was added and for other bodily fluids (serum, plasma, amniotic fluid, follicular fluid, ascites fluid, saliva) 100 ul was loaded. In addition to probing each sample with several antibodies, up to 24 samples were probed with the same antibody. This approach produces differential binding activities due to different antigen concentrations and not variability due to secondary reagents or incubation conditions. The binding can also be semi-quantitated by probing samples which have been serially diluted to obtain relative increases in concentration over detectable levels.

Use of the solid support provides means for analyzing samples using automated scanners. These scanners can be programmed to digitize information on the nitrocellulose, and further programmed to compare samples. In this way, panel assays using a multiplicity of antibodies can be performed automatically. This can be used, for example, for characterizing large numbers of known samples to determine common characteristics, as well as for characterizing large numbers of unknown samples against a known. This technique also engenders more accurate scoring of reactivity patterns as such scoring is performed by use of the digitized information.

The sample can also be probed with a variety of antibodies simultaneously, as by use of a cocktail of antibodies. This approach may provide a more efficient means of generating patterns of reactivity, but may generate complex patterns which may be difficult to analyze.

Herein, the separated strips of nitrocellulose, each containing a lane into which an aliquot of the sample was run, were separately probed using an immunoblot assay as described supra.

Preliminarily, samples of known origin were probed in order to obtain profiles against which unknown samples could be compared. Various approaches were used to derive such profiles. For one approach, several antibodies which recognize the same protein were identified. This approach increases accuracy of the probe identification. A second approach was to profile different tumor extracts with the same panel of antibodies. This generated a variety of patterns against which unknown samples could be compared. A third approach was to profile normal tissues to develop developmental profiles for different organs. All these approaches were taken in order to generate patterns of reactivity for known samples against which patterns of unknown samples can be compared.

An example of using hybridomas with different specificities is provided by fes antibodies which produce a variety of reactivity patterns against the ATP binding domain of kinase genes. The similar patterns of cross activity allow the antibodies to be grouped and tested on various biological specimens. In FIG. 25, a cell line containing the fes oncogene product was probed with a group of antibodies directed against two regions of the fes sequence as well as another oncogene, erb B. In lane I, the fes gene product was readily detected by an antibody directed against a fes sequence located in another conserved kinase region. Over-exposure of the gel does show binding for the fes gene product by the antibodies used in lane A–H but the binding activity is markedly less than the antibody used in Lane I. As another control, the two antibodies respectively in lanes J and K recognized an erb B related protein.

In FIG. 26, the same antibodies were simultaneously used to probe an extract from a cell line which contains the EGF receptor (which is encoded by the erb B protooncogene). This protein is readily detected by the erb B antibodies in addition to the p130$^{erb}$ which was also seen in the fes transformed cell line (FIG. 25). The fes antibodies used in lanes D, F, G, detect an additional protein, p30$^{fes}$, which was not detected in lane E. An ELISA assay showed that the cross reactivity pattern for this antibody, however, is similar to the antibody used in lane D and identical to the antibodies used in lanes F and G.

These same antibodies were used in FIG. 27 to probe a concentrated urine sample from a pregnant diabetic patient. A protein of approximately 70kd was detected by the three antibodies used in lanes A–C while a protein of 55 kd was detected in lanes D–H. Thus, the cross reactivity patterns of these fes proteins are useful for identifying antibodies which are likely to recognize the same protein. The subtle differences in reactivity patterns can be used to demonstrate the presence of several oncogene-related determinants on a single protein. This is shown by the 5 antibodies which detect the 55 kd protein and recognize at least 3 different fes-related epitopes. The ability of the antibodies to detect $p70^{fes}$, $p55^{fes}$, and $p30^{fes}$ may also reflect on post-translational modification differences in conformation of the ATP binding domain of the fes oncogene product.

Profiling tumor extracts such as those derived from cell lines on deposit at the NIH depository also provides targets for antibody recognition. In FIGS. 28–31, various tumor extracts were probed with fes or erb B antibodies. Lanes A–D were probed with antibodies directed against a portion of the ATP binding site of a kinase gene. Lanes E–H were probed with antibodies directed against different portions of the same binding site. Lanes I and J are probed with antibodies directed against the amino end of v-erb B (173-1C11 and 173-4All) while lanes K and L were probed with antibodies directed against a different kinase domain. These probings required a minimal amount of material (0.5 g of tissue was probed with 64 antibodies) and produced a broad spectrum of reactivity patterns.

In FIG. 28, an endometrial cancer extract is shown to have low levels of $p60^{fes}$ (lanes A–D) and p70 (lanes E–H) while $p200^{erbB}$ (lanes I,J) is readily detected. The $p200^{erbB}$ had previously been detected at highest levels in embryonic heart (data not shown). This expression of $p220^{erbB}$ appears to be inappropriate with respect to time and tissue.

In FIG. 29, a metastatic breast tumor extract was probed with the same antibodies. In this tumor, $p70^{fes}$ is readily detected in the absence of $p60^{fes}$. The antibodies directed against the amino end of erb B detect $p30^{erbB}$, and $p35^{erbB}$, and $p40^{erbB}$ while the antibodies directed against the carboxyl portion of the viral protein detect $p130^{erbB}$.

In FIG. 30, another breast cancer extract produced another reactivity pattern. In addition to $p70^{fes}$, a weak activity for $p80^{fes}$ was detected. Both of these proteins were detected with all four antibodies although this group recognized at least three different epitopes. An erb B doublet, $p130^{erbB}$, was also weakly detected (lanes K,L).

In FIG. 31, an ovarian carcinoma produced another reactivity pattern. $p60^{fes}$ was weakly detected (lanes A–D) as was $p35^{fes}$ (lanes E–H) while $p70^{fes}$ was readily detected (lanes A–D) as was $p35^{fesB}$ (lanes I,J). Thus, each tumor displayed a unique reactivity pattern and each protein described was detected by at least 2 antibodies. The proteins in lanes E–H contained at least three res-related epitopes although the proteins were probably not encoded by the fes oncogene.

In FIGS. 32–39 several additional oncogene-related proteins were detected with another panel of antibodies. In lane A of each Figure, an antibody to the ros sequence of a conserved kinase gene was used while an antibody to a different kinase domain III was used in lane B. In Lanes C–G, 5 antibodies to the amino end of β TGF were used as probes. Three antibodies to the unique carboxyl portion of the H-ras sequence were used in lanes H–J while four antibodies to a conserved region in the hormone binding domain of erb A were used in lanes K–N.

In FIG. 32, a breast carcinoma extract was probed with this series of antibodies. In lanes A and B, a 150 kd protein was detected with ros and fes antibodies directed against two different conserved regions of the kinase domain suggesting extensive kinase homology. The ros antibodies also detected a protein of 120 and 40 kd. In lanes C–G, a 25 kd protein was detected by all β TGF antibodies. These antibodies recognize at least 3 different epitopes based upon immunoblots (note the additional band at 45 kd in lane C). In lanes H–J, five different ras-related proteins were detected. The ratios of binding activities for these ras-related proteins suggests each of these antibodies detects a unique determinant. The antibody (146-3E4) in lane H preferentially detected $p200^{ras}$, $p48^{ras}$, and $p27^{ras}$. In contrast, the antibody used in lane J (146-17A5) preferentially detects p2Ias. In this exposure, these differences were most readily seen by comparing the intensities of $p27^{ras}$ with $p21^{ras}$. Although p27 was only weakly detected in lane J and p21 was only weakly detected in lane H, over-exposure of the gel indicates all 5 ras-related proteins were detected by all three antibodies.

The ovarian carcinoma probed in FIG. 33 is similar to FIG. 8 except p150ras/fes was not detected but a 50 kd β TGF protein appears in lane G. The metastatic colon carcinoma probed in FIG. 34 is also similar except the 45 and 50 kd β TGF proteins are not detected. The ovarian extract in FIG. 35 is also similar except $p45^{ras}$ and $p52^{fes}$ were present at higher concentrations relative to the other ros-related proteins and the ros-related proteins were not seen.

The lymphoma extract probed in FIG. 36 is unique due to the relatively high concentration of p27. The breast carcinoma extract probed in FIG. 37 produced another unique reactivity pattern. Although little activity was detected for the ros, fes, or ras-related proteins, p24 β TGF was readily detected is in $p22^{erbA}$ and $p55^{erbA}$. $p22^{erbA}$ was recognized by all four antibodies while $p55^{erbA}$ was readily detected only by the antibody used in lane N. Overexposure showed binding for this protein by the other three erb A antibodies. The differential activity with $p55^{erbA}$ and $p22^{erbA}$ indicate both of these proteins have two erb A related epitopes. Moreover, the antibodies did not cross react with the homologous region of the glucocorticoid or estrogen receptor and the antibodies produce nuclear staining patterns (data not shown). Thus, in contrast to the extracts probed in FIGS. 32–37, the breast tumor has elevated levels of $p22^{erbA}$. The $p22^{erbA}$ protein was also seen in the rectal tumor extract of FIG. 38 although $p55^{erbA}$ was not detected even in the overexposed gel. In FIG. 39, the metastatic lung extract had $p52^{fes}$ and a unique activity pattern for the ras probes. Although $p48^{ras}$ and $p200^{ras}$ were readily detected, there was very little activity seen for $p27^{ras}$ or $p21^{ras}$. This result was similar to the profile of several embryonic tissues (see below). As these tissues develop, the $p200^{ras}$ concentration decreased while the $p27^{ras}$ concentration increased.

Although considerable diversity is seen in the tumor samples, remarkable similarities were found in normal tissues. These similarities allow developmental profiles for different organs to be generated. In FIG. 40, a developmental profile of rat striatum was produced with 7 antibodies. In lane A, $p21^{ras}$ and $p25^{ras}$ were detected in the 18 day old embryo. By day 2, $p150^{ras}$ was barely detected in addition to $p21^{ras}$ and $p25^{ras}$ was readily detected and is present in subsequent panels. In lane B, $p52^{ras}$ was readily seen at 18 days of fetal development. Overexposure of the gel revealed $p200^{ras}$. By 18 days, $p27^{ras}$ was easily seen ($p200^{ras}$ was no longer detectable in overexposed gel). The concentration of $p27^{ras}$ was highest by day 70. $p21^{ras}$ was also readily detectable at day 70 although overexposure indicated $p21^{ras}$ was present at all five time points. In lane C, $p150^{myc}$ was also an adult specific protein which was barely detected at day 2 but readily seen by day 18. In lane D, $p120^{myb}$ was an embryo specific protein which was detected only in the fetal panel. In lane E, $p100^{int-1}$, $p70^{int-1}$, $p45^{int-1}$, $p90^{sis}$, and $p56^{sis}$ do not appear to be developmentally regulated. In lane G, $p60^{sis}$ was highest in the embryo panel. Thus, in contrast to the tumor extracts described in FIGS. 4–15, the oncogene-related protein profiles of normal tissues are much more uniform and tightly regulated.

Thus, FIGS. 25 through 40 show that a known sample can be probed with various antibodies in order to generate a pattern of reactivity. The above examples show the cross reactivity of various antibodies not only among the same proteins in different samples but also among various proteins.

A. Classification of Known Samples

Tumor extracts or other body samples may also be characterized according to the various gene products produced. Presently, various tumor extract x antibody combinations were scored using the immunoblot technique to determine the presence and levels of various oncogene products. These data are presented at FIGS. 41 and 42. Tumor extracts were derived from cell lines on deposit at the NIH depository, and samples were electrophoresed and blotted onto nitrocellulose as described above. Antibodies against polypeptides encoded by oncogenes from various oncogene families were used to probe the samples.

The reactivities were scored for the presence and level of expression of oncogene product. In FIG. 41, $p52^{ras}$ was detected in all of the ovarian extracts but highest levels were found in tumors listed as minimum or moderate. $p60^{src}$ and $p48^{src}$ were predominantly detected in the ovarian tumors with highest frequencies in the advanced category. $p125^{ros}$ and $p15^{ros}$ were detected in most of the tumors but in the breast extracts, expression was concentrated in the adenomas and those carcinomas classified as minimal or moderate. $p150^{ros}$ expression was concentrated in the breast tumors in contrast of $p120^{ros}$ which was found in only half of the breast tumors although this protein was detected in most other tumors with the exception of the endometrial extracts. $p22^{erb}A$ was scattered throughout these tissues but was not found in any of the extracts listed as advanced.

Additional segregation of activities are seen in FIG. 42 which lists several of the kinase-related proteins. In this table, the high levels of $p70^{fes}$ in the ovarian and endometrial extracts is striking. Similarly, the restriction of $p130^{erbB}$ to the ovarian and lung extracts may be significant.

Thus, tumor extracts can be characterized with respect to oncogene or oncogene-related products. Using specific antibodies, proteins common to specific tumor types can be detected. These patterns of reactivity can be used as a standard against which patterns of unknown samples may be compared.

B. Markers in Body Fluids

The panel assay may also be used to monitor protein production in a single individual. In this way, the effects of therapy may be non-invasively monitored by screening, for example, urine samples. This approach involves the screening of an original sample from a patient in order to obtain a profile of the activity pattern of a panel of antibodies. As therapy progresses, subsequent samples are monitored using the same original sample as a standard for comparison. FIG. 43 shows sequential urine samples from gestational trophoblast disease patients undergoing chemotherapy. The asynchronous appearance of a number of oncogene-related proteins is apparent. These data can be further correlated with clinical data regarding therapy effectiveness in order to monitor patients after therapy.

C. Detection of Oncogene-Related Proteins

Antibodies against polypeptides encoded by oncogenes may recognize other proteins which also contain the conserved polypeptide or portions thereof. Thus, panels of antibodies may be used to detect oncogene-related proteins in a sample by probing the sample with multiple antibodies each against distinct regions of the polypeptide. By determining a pattern of reactivity with different antibodies, different oncogene related proteins can be identified.

The $p21^{ras}$ detected by the H-ras-specific antibody represents a subset of the $p21^{ras}$ detected by the broadly reactive antibody. All samples containing p21 detected by the H ras specific antibodies contained p21 detected by antibody 142-24E05 but not vice versa. The other proteins detected by the H ras specific antibodies were not detected by 142-24E05 indicating the conserved ras region is absent or at least altered so as to preclude 142-24E5 binding. However, the concordance of binding by the three H-ras specific antibodies indicates the same protein was detected by all three antibodies. The similar ratio of binding of the antibodies to $p200^{ras}$, $p48^{ras}$, and $p27^{ras}$ suggests some structural similarity in the epitopes detected by the three antibodies. This similarity can be addressed using a number of techniques. One approach is to digest labelled antigens and subject the digest to two dimensional peptide mapping. If the larger molecule is not well recognized in solution, additional approaches are possible. For example, samples containing different combinations of immunologically related proteins could be subjected to partial digestion and immunoblotted. If there is a precursor-product relationship, the smallest size protein detected with the antibody should be the same (a control incubation without added proteases would control for sample differences of endogenous proteases). Alternatively, the partial digest (to expose the antigenic site) may be immunoaffinity purified and then immunoblotted or peptide mapped. Identity of similar sized proteins detected by different antibodies or the same antibody in different samples (i.e. urine and tissue) may be tested using similar approaches or the isoelectric point could be determined using two dimensional gels and immunoblot detection. This approach is also useful for identification of multiple forms migrating at similar rates on SDS polyacrylamide gels.

VIII. SERUM SCREENING IN ASYMPTOMATIC INDIVIDUALS

Set forth below are studies on two different cohorts of workers known to have exposure to environmental carcinogens. None of the workers showed clinical symptoms of neoplastic disease. Both studies show that the individuals with the highest exposure to carcinogens also show abnormal expression of oncoprotein. In the first example, one individual with known exposure to several carcinogens, including PCB's, asbestos, and cigarette smoke also showed a fifty-fold elevated level of H-ras protein 21. Eighteen months after this screening, this individual developed a colorectal adenoma. Upon removal of the adenoma, the serum levels of H-ras p21 returned to normal. In the second example, foundry workers exposed to polyclic aromatic hydrocarbon carcinogens were found to have abnormally elevated expression of the fes oncogene-related protein. The abnormal expression was found only in some of the workers with the highest workplace exposures to the carcinogen. Unexposed individuals had non-detectable levels of oncoprotein. These studies show the utility of the present methods and monoclonal antibodies for cancer prognosis, and also show important markers which indicate exposure to environmental carcinogens. The H-ras p21 marker is unexpectedly useful for prognosis of colorectal adenomas. The fes oncogene-related protein is useful as an indicant of polyclic aromatic hydrocarbon exposure.

EXAMPLE 1

Serum Screening of Workers Exposed to PCBs

Serum from a group of sixteen municipal workers who had possible previous exposure to polychlorinated biphenyls (PCBs) was screened using monoclonal antibodies raised against polypeptides encoded by oncogenes. The results presented herein show that the individual with the worst history of exposure to carcinogens also showed the most abnormal expression of H-ras p21. Eighteen months after the serum screening, this individual developed a colorectal adenoma. Upon surgical removal of the adenoma, expression of H-ras reverted to normal.

Methods
1. Individual Background Screen

Sixteen municipal workers who had been involved in the clean up of PCB containing transformers were evaluated for medical and occupational history, as well as examined physically and clinically. The transformer oil contained approximately 600,000 ppm PCBs, and the clean-up lasted several months. All subjects were white males with an average age of 42, and the range of ages from 27–65.

The workers were questioned regarding exposure to PCBs from other sources, as well as exposure to other carcinogens, such as asbestos and cigarette smoke, and examined physically, with particular reference to dermatologic examination, laboratory tests were performed for analysis of serum triglycerides, serum PCB levels, and liver function tests (SGOT, SGPT, LDH, alkaline phosphatase, and bilirubin; subjects were requested to refrain from ethanol consumption for two weeks prior to testing, and to have no oral intake on the day of testing). Tests were carried out by routine methods.

All sixteen subjects reported some dermal contact with the PCB-containing transformer oil during this work period; in addition, two had prior potential exposure to PCB-containing transformer oil over the past twenty years (patients 9 and 10). Seven workers reported having worked with other carcinogenic materials in the past; this was primarily asbestos exposure from insulation handling, although one individual also had significant work exposure to chlorinated hydrocarbon solvents and ionizing radiation (patient 14). Twelve of the workers were current cigarette smokers or recent ex-smokers (within the past 5 years) and four had never smoked. Two individuals reported having acneiform lesions on the arms, legs and feet shortly after exposure (patients 4 and 8), but physical examination revealed no abnormalities consistent with PCB exposure in any of the workers.

In all cases, liver function tests were within normal limits. In only three cases were serum triglycerides elevated. One individual (patient 8) had a very high serum triglyceride level which had been reportedly normal in the past prior to PCB exposure; however, his serum PCB level was quite low. In the other two hypertriglyeridimic individuals, the prior status in terms of triglyceride levels was unknown, and their serum PCB levels were also relatively low. Furthermore, the individual with the highest serum PCB level had a normal triglyceride level. On the basis of these data, it is impossible to draw only conclusions regarding correlations between relatively low serum PCB levels and serum triglycerides, an association which has been noted with higher PCB exposures.

As noted, overall serum PCB levels were quite low, attesting to the adequacy of protective measures taken. In general, levels less than 10 ppb are not viewed with concern since such levels can often be identified in non-occupationally exposed normal controls. But this measure, only one individual, patient 6, could be considered to have a seriously elevated serum PCB level.

Patient 6, the individual shown to have extremely aberrant ras expression, also had the highest incident of known carcinogen exposure. Patient 6 was a 57 year old white male. At the time of the serum screening, he showed no overt symptoms of neoplastic disease. The individual had worked in building maintenance for 25 years, a job which included the spraying and removal of asbestos insulation, the application of various pesticides including chlordane, and the clean-up of transformer oils containing PCBs. He had also smoked a pack of cigarettes a day for many years. His physical examination was notable only for mild hypertension.

2. Serum Screening

An adaptation of the urine immunoblotting technique of Niman et al., PNAS-USA 82:7924–7928 (1985); herein incorporated by reference, was used for screening serum. For the assay, subject serum was prepared and probed with monoclonal antibodies raised against polypeptides as described infra. The monoclonals used are designated infra.

For the assay, 100 µl of serum was mixed with 400 µl phosphate-buffered saline (PBS) at pH 7.4, 25 µl 2-mercaptoethanol and 475 µl of sample buffer in deionized water (6.25% sodium dodecyl sulfate, 6.25% glycerol), and placed in a boiling water bath for 5 minutes. Samples were then loaded on a 5–17% polyacrylamide gel and electrophoretically separated and transferred to nitrocellulose. After blocking with PBS containing 3% bovine serum albumin and 0.1% Triton X-100, the nitrocellulose was incubated overnight at 4° C. with monoclonal antibodies directed against synthetic peptides representing predicted oncogene sequences (ascites fluid diluted 1:2000). After washing three times, the nitrocellulose was incubated with rabbit anti-mouse IgF (1:500) for 60 minutes at room temperature. After three more washes, the nitrocellulose was incubated with $^{125}$I-labelled protein A ($10^6$ cpm/ml). Binding was visualized with intensifying screens.

The primary antibodies utilized were directed against protein sequences of the following oncogenes (see FIGS. 44(A) and (B)):

sis (lane 1, hybrid 112-09B10 (ATCC HB8800), sequence SLGSLTIAEPAMIAEC);

fes (lane 2, hybrid 127-42C11 (ATCC HB9561)and lane 3, hybrid 127-50D04 (ATCC HB8968), sequence LMEQCWAYEPGQRPSF; lane 15, hybrid 121-I4C09 (ATCC HB9875), sequence IGRGNFGEVFSG(C));

β-TGF (lane 4, hybrid 100-30C05 (ATCC HB9787) and lane 5, hybrid 100-34E06 (ATCC HB9788), sequence ALDTNYCFSSTEKNC); int-1 (lane 6, hybrid 222-35C08 (ATCC HB9052) and lane 12, hybrid 222-37F04 (ATCC HB9786), sequence LHNNEAGRITVFS(C));

myb (lane 7, hybrid 133-I0F06 (ATCC HB9077), sequence LGEHHCTPSPPVDHG);

src (lane 8, hybrid 203-07D10 (ATCC HB8898), sequence (C)GSSKSKPKDPSQRRHS);

c-myc (lane 9, hybrid 155-11C07 (ATCC HB8976), lane 13, hybrid 155-08G01 (ATCC HB9001), and lane 14, hybrid 155-09F06 (ATCC HB9000), sequence CSTSSLYLQDLSAAASEC);

mos (lane 10, hybrid 165-35F02 (ATCC HB9784), sequence LGSGGFGSVYKA(C));

H-ras (lane 11, hybrid 142-24E05 (ATCC HB8679), sequence YREQIKRVKDSDDVPMVLVGNKC and lane 16, hybrid 146-03E04 (ATCC HB8997), sequence YTLVREIRQHKLRKLNPPDESGPGC).

Results and Discussion

Results are presented in Table 7, below. The most striking result is that for patient 6. Patient 6 had the worst exposure to carcinogens of the 16 workers tested. This individual showed the highest serum PCB levels, and was also positive for asbestos exposure and smoking. As can be seen Table 7, this individual showed abnormal expression of both fes and ras markers, with the ras marker expression being far above the normal range. In a follow-up study, set forth infra, this individual was shown to have developed cancer; upon surgical removal of the cancerous tissue, ras expression reverted to normal.

The findings with regard to other workers also show several patterns of expression. One-half of the smokers (patients 3–9) showed abnormal fes-oncogene related banding patterns, whereas none of the non-smokers displayed this pattern. One smoker also had an aberrant pattern for sis oncogene-related proteins, but this is of unknown significance. It is of note that example 2, infra, also shows abnormal expression of fes oncogene-related protein only in individuals known to be exposed to polycyclic aromatic hydrocarbon carcinogens, and these individuals were also smokers.

The patterns for the other oncogene or oncogene-related proteins were normal except for ras. Apart from patient 6, two other individuals had detectable levels of ras p21. In both of these cases, the bands were relatively weak, and there did not appear to be any connection to exposure to PCBs. One patient (10) had a PCB level of 6.5 with a positive smoking history and a positive history of other carcinogen exposure (asbestos). The other individual (patient 11) had a PCB level of 0.3 and no other known exposure history.

confirmed by use of antibodies directed to the conserved region of ras p21 (lane 11) as well as the H-ras specific carboxy terminal region (lane 16), and the use of antibody or other receptors directed to both conserved regions as well as protein-specific regions is a method generally applicable to confirm the identity of a protein marker, if it is desired. The identity of the protein, however, may not be critical where the important information derived is the relative presence or absence of the protein, rather than the composition of the protein itself. Thus, patient 6, the individual with the most extreme exposure to known carcinogenic substances also was found to be the individual most aberrantly expressing H-ras p21.

These data show that ras oncogene p21 is a useful as a marker for screening to determine if an individual has been exposed to a carcinogen. The follow-up data, presented below, show that this method and the receptors used are useful tools for cancer prognosis.

Follow-Up Study On Patient 6

Approximately 18 months after the serum screening which showed highly elevated levels of ras protein, patient 6 manifested clinical symptoms of cancer. Patient 6 developed rectal bleeding, and colonoscopy revealed a 2 cm. tubulo-villous adenoma of the descending colon. This adenoma was removed surgically. Patient 6 was re-screened approximately 6 weeks after removal of the adenoma. This screen showed expression of the ras oncogene proteins had reverted to a normal pattern. These patterns are shown at FIG. 45. Lane A shows ras p21 expression 18 months prior to the showing of clinical symptoms. Lane B shows that, 6 months after the removal of the adenoma, the ras band is not visible.

These data show that H-ras p21 expression can be correlated to development of colonic carcinomas as well as exposure to carcinogens. Detection of this abnormal H-ras expression some 18 months prior to the development of

TABLE 7

Summary of Findings on PCB Exposed Workers

| | PCB Levels (ppb) | | | | | | | | | | | | Serum Oncogene Proteins | | |
|---|---|---|---|---|---|---|---|---|---|---|---|---|---|---|---|
| Patient | 2,2'3,3', 4,4'5 Hepta | 2,2'3,3', 4,4'5,5' Hepta | 2,2'3,4, 4'5' Hexa | 2,2'3,4, 4'5 Hexa | 2,2',4, 4'5,5' Hexa | 2,3,3', 4'4 Penta | 2,3,4, 4'5 Penta | 2,3', 4,4' Tetra | Liver Func-tion | Trigly-cerides (mg/dl) | History of Smoking | Other Carcinogen Exposure | fes | ras | sis |
| 1 | 1.0 | — | — | 0.5 | — | 0.5 | — | — | — | WNL | WNL | Yes | No | — | — | — |
| 2 | 2.2 | — | — | 0.8 | — | 0.8 | — | 0.6 | — | WNL | WNL | Yes | No | — | — | — |
| 3 | 0.6 | — | — | 0.6 | — | — | — | — | — | WNL | WNL | Yes | No | ++ | — | — |
| 4 | 2.8 | — | 1.3 | 0.8 | — | 0.7 | — | — | — | WNL | 193 | Yes | Yes | ++ | — | ++ |
| 5 | 6.3 | — | 1.9 | 1.5 | — | 1.7 | — | 1.2 | — | WNL | WNL | No | No | ++ | — | — |
| 6 | 22.2 | 0.6 | 2.0 | 5.2 | 0.4 | 3.6 | 2.5 | 7.2 | 0.7 | WNL | WNL | Yes | Yes | ++ | +++ | — |
| 7 | 0.4 | — | — | — | — | 0.4 | — | — | — | WNL | WNL | Yes | No | ++ | — | — |
| 8 | 1.8 | — | 0.4 | 0.6 | — | 0.8 | — | — | — | WNL | 597 | Yes | No | ++ | — | — |
| 9 | 3.0 | — | 2.1 | 0.3 | — | 0.6 | — | — | — | WNL | 271 | Yes | Yes | ++ | — | — |
| 10 | 6.5 | — | 2.3 | 1.6 | — | 1.8 | — | 0.8 | — | WNL | WNL | Yes | Yes | — | + | — |
| 11 | 0.3 | — | 0.3 | — | — | — | — | — | — | WNL | WNL | No | No | — | + | — |
| 12 | 0.3 | — | — | — | — | 0.3 | — | — | — | WNL | WNL | Yes | Yes | — | — | — |
| 13 | 2.0 | — | 0.3 | 0.6 | 0.4 | 0.7 | — | — | — | WNL | WNL | No | Yes | — | — | — |
| 14 | 1.5 | — | — | 0.6 | 0.4 | 0.5 | — | — | — | WNL | WNL | No | Yes | — | — | — |
| 15 | 4.5 | — | 0.5 | 1.1 | 0.3 | 1.6 | 0.4 | 0.6 | — | WNL | WNL | Yes | No | — | — | — |
| 16 | 0.9 | — | — | 0.9 | — | — | — | — | — | WNL | WNL | Yes | No | — | — | — |

WNL - within normal limits; — = negative; + = weakly positive; ++ = moderately positive; +++ = strongly positive Patient 6 was extremely aberrant for H-ras p21 expression. At lanes 11 and 16 of FIG. 44B, the bands for p21 are shown to be quite pronounced. Cf., lanes 11 and 16 of FIG. 44A which show no p21 expression for normal, unexposed individuals. It is worth noting that the identity of p21 was clinical symptoms of cancer shows the value of this marker as a prognostic tool for cancer.

To what specific carcinogen or mixture of carcinogens the colorectal carcinoma can be attributed is unclear. Patient 6 did not have any documented exposure to the carcinogens known to activate the ras gene, except for benzo(a) pyrene from cigarette smoking. See Brandt-Rauf and Pincus, Occup. Med. 2:27-38(1987) and Spandidos and Kerr, Br. J. Cancer 49:681-688 (1984), both of which are incorporated herein by reference, for a discussion of carcinogens which activate ras (benzo(a)pyrenes, dimethylbenzathracene, N-nitroso compounds and ionizing radiation) and the expression of ras in human colonic carcinomas and pre-malignant colonic polyps. Patient 6 did have a long history of exposure to asbestos, which has been implicated in the development of colo-rectal cancer. Wylie et al., Sem. Occupl. Med. 2:291-309 (1987). Whether asbestos, by itself or in combination with other environmental carcinogens, activated the ras oncogene, is not clear. It is clear, however, that (a) H-ras p21, with its expression well in advance of the manifestation of clinical symptoms of neoplastic disease, is a powerful prognostic tool, (b) the methods presently described provide for an accurate and non-invasive screening, the results of which are useful to predict the onset of clinical symptoms of neoplastic disease, and (c) the receptors herein described, i.e., those directed against H-ras p21, whether in the form of antibodies or fragments thereof or nucleic acids, are useful to detect these prognostic markers.

One explanation for the overexpression of p21 by patient 6 may be that exposure to asbestos caused chromosomal abnormalities which led to the activation of the ras gene. While in the present example the specific pathogenic machinery is not clearly understood, other oncogenes, for whom environmental activators are known, may be chosen as markers for the present screen. It is possible, however, that the clastogenic effect of asbestos could manifest itself in the activation of the ras gene. See, Jaurand et al., Mut. Res. 169:141-148 (1986), and Kelsey et al., Br. J. Cancer 54:107-114 (1986) where asbestos fibers are shown to be clastogenic on cells in culture. For example, the myc oncogene has been shown to be activated as a result of translocation of the proto-oncogene to a site where transcription is accelerated, Erikson, et al., PNAS-USA 80: 820-824 (1983), and a similar scenario may be envisioned for asbestos-caused ras activation. More recent studies have shown that asbestos fibers are capable of transfecting exogenous DNA segments, including oncogenes and promoter sequences, into primate cells in culture and producing cell transformation. Appel, et al., PNAS-USA 85: 7670-7674 (1988), and this may be the mechanism of ras activation.

It is known that the introduction of the ras proto-oncogene linked to a viral transcriptional promoter into cells in culture results in increased expression of the gene and causes malignant transformation of the transfected cells. Chang et al., Nature 297: 479-483 (1982). Thus, in this individual, it is possible that prolonged exposure to asbestos fibers produced increased expression of the ras proto-oncogene in his colonic epithelium. This was manifested by increased quantities of the proto-oncogene encoded p21 protein in his serum. Ultimately, the proto-oncogene over-expression led to colonic neoplasia, in this case, a tubulo-villous adenoma which was identified clinically 18 months prior to its progression to a malignant growth. When the adenoma was surgically removed, the source of the ras encoded p21 protein was removed, and p21 protein was no longer detected in the patient's serum.

Thus, while the present study was based on a group of individuals who had all been exposed to a known environmental carcinogen, PCB, the results unexpectedly yielded a marker which may be useful in predicting neoplastic disease resulting from asbestos exposure. In any event, the present study shows that the present method is useful for predicting the onset of cancer prior to manifestation of clinical symptoms.

EXAMPLE 2

Serum Oncogene Proteins In Foundry Workers

In this study, a well-defined occupational cohort of iron foundry workers with known, quantified exposure to a common occupational carcinogen, benzo(a)pyrene were assayed to determine if any oncogene or oncogene-related markers are associated with exposure to this carcinogen. Benzo(a)pyrene (BP)and related polycyclic aromatic hydrocarbons (PAHs)have been associated with increased risk of lung cancer in smokers, coke oven workers and foundry workers (Redmond et al., Annals of the New York Academy of Sciences 271:12 (1976); IARC, Polynuclear aromatic compounds, In: Monographs on the Evaluation of the Carcinogenic Risk of Chemicals to Humans, Vol. 34, Part 3, Lyon: IARC (1984); IARC, Tobacco smoking, In: Monographs on the Evaluation of Carcinogenic Risk of Chemicals to Humans, Vol. 38, Lyon: IARC (1986). Such PAHs have been shown to be capable of activating oncogenes both in vivo and in vitro. Ballmain and Pragnell, Nature 303:72 (1983); Marshall et al., Nature 310:586 (1984). Furthermore, not only are extensive occupational histories available for this cohort, but also their exposure has been well-defined in terms of workplace air levels of BP. A clear dose-related increase was seen in levels of PAH-DNA adducts in the peripheral leukocytes of these workers , Perara et al., Cancer Res. 48:2288 (1988b), which was consistent with measurements of DNA adducts by the 32p postlabeling method, Phillips et al., Mutation Res. 204:531 (1988); Hemminki et al., J. of Work Environment and Health 14:55 (1988). This cohort therefore represents a model population for the study of oncogene activation related to occupational exposure.

Materials and Methods

The study cohort of workers employed at an iron foundry in Finland has been previously described (Hemminki et al., 1988, supra; Perera et al., 1988b, supra). Briefly, the foundry workers were segregated by two industrial hygienists familiar with the workplace into groups according to the level of exposure to BP based on extensive industrial hygiene sampling data and job description. This classification was considered representative of exposure during the past 5-10 years, since individuals in this plant tend to remain in the same job and are generally long-term employees. Workers with 8 hour TWA exposures greater than 0.02 ug/m$^3$ were classified in the high exposure group and workers with TWA exposures between 0.05 and 0.2 ug/m$^3$ were classified in the medium exposure group; peak BP levels as high as 2-3 ug/m$^3$ were known to occur for certain individuals in the casting and shakeout areas of the foundry. Clinical information including cigarette consumption was collected on all workers. Unexposed controls for comparison were recruited from patients referred to the Institute of Occupational Health for evaluation of possible occupational disease unrelated to PAH exposure or cancer. The control population had a lower average cigarette consumption than the foundry workers but was similar in terms of age and sex distribution (Perera et al., 1988b, supra).

For the purposes of this study, repeat peripheral blood samples were available for 8 exposed workers (3 in the high exposure group and 5 in the medium exposure group) and for 10 unexposed controls (a total of twenty-eight samples). Two or three blood samples had been collected on the workers at different times. For all workers, samples were available immediately following a month-long vacation and 6 weeks after returning to work. For two of the workers in the medium exposure group, an additional blood sample was collected during the following 12 months. Single peripheral blood samples were collected on the unexposed controls. Blood samples (30–50 ml) were collected in heparinized plastic tubes, coded and centrifuged. Buffy coat, red cells and plasma were collected ad stored frozen at −70° C. until time of analysis. PAH-DNA adducts were determined for these same workers as reported previously (Perera et al., 1988b, supra). The values for DNA adducts in a subset of samples assayed for serum oncogene proteins are given in Table 8; missing values reflect the fact that inadequate amounts of DNA were available for some samples.

These samples have now been analyzed blind for the presence of protein products encoded by nine different oncogenes (sis, fes, B-TGF, int-1, myb, src, myc, mos, and ras) by the immunoblotting technique as previously described (Niman et al., 1985, supra; Brandt-Rauf and Niman, Brit J. Indus. Med. 45:689 (1988)). Briefly, 100 ul of serum is mixed with 400 ul of phosphate-buffered saline PBS) at pH 7.4, 25 1 of 2-mercaptoethanol, an 475 ul of sample buffer in deionized water (6.25% sodium dodecyl sulfate, 6.25% glycerol), and placed in a boiling water bath for five minutes. Samples were then loaded on a 5–17% polyacrylamide gel and electrophoretically separate and transferred to nitrocellulose. After blocking with PBS containing 3% bovine serum albumin and 0.1% Triton X-100, the nitrocellulose is incubated overnight at 4° C. with monoclonal antibodies directed against synthetic peptides representing predicted oncogene sequences (ascites fluid diluted 1:2000). After exhaustive washing, the location of the oncogene protein-antibody bands on the nitrocellulose is determined colorimetrically using a secondary anti-mouse IgG antibody and an avidin-biotin-peroxidase complex (Vectastain; Vector Labs, Burlingame, Calif.). Approximate quantification of positive results is achieved by serial dilution of samples until no difference from normals is detectable; a five-fold increase in protein expression is considered a positive result. The primary antibodies used were directed against the following oncogene protein sequences:

sis (hybrid 112-09B10) (ATCC HB8800), sequence SLGSLTIAEPAMIAEC)

fes (hybrid 127-42C11) (ATCC HB9561) and 127-50D04 (ATCC HB 8968), sequence LMEQCWAYEPGQRPSF, and hybrid 121-14C09 (ATCC HB9875), sequence IGRGNFGEVFSG(C))

B-TGF (hybrid 100-30C05 (ATCC HB9787) and hybrid 100-34E06 (ATCC HB9788), sequence ALDTNYCFSSTEKNC)

int-1 (hybrid 222-35C08 (ATCC HB9052) and hybrid 222-37F04 (ATCC HB9786), sequence LHNNEAGRTTVFS (C))

myb (hybrid 133-10F06 (ATCC HB9077), sequence LGEHHCTPSPPVDHG)

src (hybrid 203-07D10) (ATCC HB8898), sequence (C) GSSKSKPKDPSQRRHS)

myc (hybrids 155-11C07 (ATCC HB8976), 155-08G01 (ATCC HB9001), and 155-09F06 (ATCC HB9000), sequence CSTSSLYLQDLSAAASEC)

mos (hybrid 165-35F02 (ATCC HB9784), sequence LGSGGFGSVYKA(C))

ras (hybrid 142-24E05 (ATCC HB8679), sequence YREQIKRVKDSDDVPMVLVGNKC, and hybrid 143-03E04 (ATCC HB8997), sequence YTLVREIRQHKLRKLNPPDESGPGC)

In this immunoblotting system, these antibodies have been found to give specific, sensitive and reproducible results. The specificity of the antibodies has been demonstrated by the blocking of the activity by preincubation with the specific peptide for the oncogene and the failure of the blocking of the activity with peptides of other oncogenes (Niman et al., 1985). The assay system is capable of detecting proteins in the nanogram range and is found to give reproducible results when repeated on the same sample.

Results and Discussion

The results, as shown in Table 8, show that two different workers (patients 2 and 7), both of whom were known to have either high (2) or medium (7) exposure to PAHs, were positive for increased levels of fes oncogene-related protein products. The serum samples from each of these individuals which tested positive were drawn post-vacation and after six weeks of work. There were no positive bands for the proteins of seven of the oncogenes in any of the samples (sis, B-TGF, int-1, myb, src, myc, mos). Only one sample, from patient 5, was found to be positive for ras oncogene-related protein products; however, in this case, two other samples from the same worker, taken at different times, were negative. All results for serum oncogene proteins in the unexposed controls were negative.

In this study it is notable that the only positive results for elevated serum levels of oncogene-related proteins were obtained in individuals in the medium or high exposure groups. Furthermore, as shown in Table 8 and reported previously (Perera et al., 1988b, supra), these individuals also have high levels of PAH-DNA adducts compared to low exposed or unexposed individuals. Although two of the individuals with positive oncogene proteins were also smokers of approximately one pack of cigarettes per day (patients 2 and 5), it is likely that the major contribution to their body burden of PAHs was due to workplace exposure. For example, exposure at 0.2 ug/m$^3$ is approximately equal to the BP dose from smoking 5 to 7 packs of cigarettes per day.

TABLE 8

Serum Oncogene Protein Expression and PAH-DNA Adducts in Foundry Workers and Unexposed Controls

| Ambient Exposure, ug BP/m$^3$ | Patient | Smoking cigarettes/d | PAH-DNA Adduct Levels[1], fmol/ug | | | Serum Oncogene Proteins[1] | | | | | |
|---|---|---|---|---|---|---|---|---|---|---|---|
| | | | | | | fes | | | ras | | |
| | | | Post-Vacation | Work 1 | Work 2 | Post-Vacation | Work 1 | Work 2 | Post-Vacation | Work 1 | Work 2 |
| >0.2 | 1 | 0 | 0.11 | 0.8 | NA | – | – | NA | – | – | NA |
| (high | 2 | 20 | 0.13 | 2.0 | NA | + | + | NA | – | – | NA |
| exposure) | 3 | 0 | NA | 2.8 | NA | – | – | NA | – | – | NA |
| 0.05–0.2 | 4 | 15 | 0.13 | 0.36 | NA | – | – | NA | – | – | NA |
| (medium | 5 | 20–25 | NA | 0.32 | 0.42 | – | – | – | – | + | – |
| exposure) | 6 | 15 | NA | 0.8 | 0.5 | – | – | – | – | – | – |
| | 7 | 0 | 0.48 | 1.28 | NA | + | + | NA | – | – | NA |
| | 8 | 20 | ND | 0.4 | NA | – | – | NA | – | – | NA |
| <0.05 | 9 | 15 | | 0.08 | | | – | | | – | |
| (unexposed | 10 | 10 | | ND | | | – | | | – | |
| controls) | 11 | 0 | | 0.14 | | | – | | | – | |
| | 12 | 0 | | ND | | | – | | | – | |
| | 13 | 0 | | ND | | | – | | | – | |
| | 14 | 0 | | 0.3 | | | – | | | – | |
| | 15 | 0 | | ND | | | – | | | – | |
| | 16 | 10 | | ND | | | – | | | – | |
| | 17 | 15 | | 0.1 | | | – | | | – | |
| | 18 | 0 | | 0.1 | | | – | | | – | |

NA = not available
ND = non-detectable
[1]Post-vacation samples were drawn after a one month vacation; work 1 samples were drawn six weeks after returning to work; work 2 samples were drawn more than two months after returning to work The positive results for particular oncogene expression in these workers are of interest, since it is known that foundry workers are at increased risk for the development of lung cancer (IARC, 1984, supra). The worker with the isolated positive result for ras proteins is notable, since PAHs are known to activate the ras gene (Balmain and Pragnell, 1983, supra; Marshall et al., Nature 310:586 (1984)) and ras gene activation has been found frequently in human lung cancers, particularly of the non-small-cell variety (Slamon et al., Science 224:256 (1984); Rodenhuis et al., New Eng. J. Med. 317:929 (1987); Kurzrock et al., Cancer Res. 46:1530 (1986)). For example, in a recent study of lung cancer (Rodenhuis et al., 1987, supra), 50% of adenocarcinoma patients (5 of 10) had an activated form of one type of ras gene (K-ras and it was felt that this oncogene activation represented a relatively early event in the development of the lung cancers and was related to cigarette smoking. In our own studies of serum oncogene protein levels in non-small-cell lung cancer patients, 15 of 18 patients had increased expression of the ras gene products, and 12 of these were known to have been cigarette smokers. Increased urinary levels of ras oncogene protein products in lung cancer patients have also been demonstrated (Niman et al., 1985, supra). In our screening of the sera of 16 clinically healthy hazardous waste workers with known carcinogen exposure, one individual had an extremely abnormal increased expression of ras gene protein, supra. This individual also had the worst history of exposure to carcinogens including asbestos and cigarette smoke. Thus, it is possible that ras gene activation plays a significant role in pulmonary carcinogenesis, particularly that caused by exposure to environmental carcinogens such as PAHs. However, in the current study as noted above, the individual (patient 5) with elevated serum ras proteins was found to be positive on only one of the three samples. The significance of this isolated finding in terms of this individual's risk for the development of lung or other cancers remains uncertain.

As noted, however, two workers (patients 2 and 7) had consistently elevated serum levels for fes oncogene-related protein products. One of these workers was a caster in the Zimmerman process with high exposure to PAHs for the past 15 years, smoked cigarettes and had a father and mother who both died of lung cancer. The other worker had been a core-setter with medium exposure to PAHs for the past 9 years. Both of these individuals also had occupational dermatitis and had long-term treatment with topical steroids. Whether topical exposure to steroids influenced the metabolic activation of PAHs or whether the dermatitis increased dermal absorption of the carcinogens is not clear. Like ras, fes has been found to be frequently expressed in human lung cancers. In one study, all four lung cancers studied were positive for increased expression of the fes gene (Slamon et al., 1984, supra). In our prior study of serum oncogene protein levels in lung cancer patients, 11 of 18 individuals were positive for fes products, and 8 of these were known to have been cigarette smokers. Increased urinary levels of fes oncogene products have also been found in lung cancer patients (Niman et al., 1985, supra). In addition, in our study of clinically healthy hazardous waste workers, only heavy cigarette smokers (6 of 12) were found to be positive for the fes gene products in their serum. Furthermore, it is known that during mammalian development, the protein product of the fes gene is expressed in a very limited tissue-specific fashion (Pimentel, Oncogenes, Boca Raton: CRC Press (1986)); for example, in young chicks 6 to 18 days old, the fes gene product is detected at high levels only in three tissues—bone marrow, liver and lung (Mathey-Prevot et al., Cell 28:897 (1982)). Thus, in pulmonary carcinogenesis, the expression of the fes gene products may signal a regression to an earlier stage of pulmonary cellular development, and, once again, this expression may be particularly associated with exposure to the carcinogens of cigarette smoke such as PAHs. Therefore, in this study, the next logical step is to determine if the two workers with known long-term medium-to-high level workplace exposure to PAHs and known high levels of PAH-DNA adducts and with consistently hgh levels of fes oncogene protein products in their serum are the individuals in this cohort most at risk for the development of malignant disease, especially cancer of the lung.

Further long-term follow-up of this and other similar cohorts will be necessary before the predictive value of specific oncogene proteins as markers for cancer development can be precisely ascertained. However, the current results show that serum oncogene proteins are useful molecular epidemiologic markers for the surveillance of populations at risk for the development of occupational cancers.

While the examples set forth herein specifies the use of monoclonal receptors, other receptors, such as nucleic acid sequences corresponding to the oncogene-related proteins and related polypeptides herein discussed, may be used, and methods for such preparation and use are within the skill of the art. In addition, to the extent other body samples, such as tissue or urine, may be used for the above assay, those methods, described herein, are within the skill of the art.

IX. MATERIALS AND METHODS

A. Growing Of Viruses And Cell Lines

An uninfected mink lung cell line (CCL64), the same line productively transformed with the Snyder-Theilen strain of feline sarcoma virus (ST-FeSV) and feline leukemia virus B (FeLV-B) and designated MSTF, as well as the same line non productively infected with Gardner-Arnstein feline sarcoma virus (GA-FeSV) and designated 64F3Cl7 were cultured as described in Sen et al., *Proc. Natl. Acad. Sci. USA*, 80, 1246–1250 (1983). A non-producing avian myeloblast cell line, non-productively infected with avian myeloblastosis virus was cultured as described in Duesberg et al., *Proc. Natl. Aced. Sci. USA*, 77, 5120–5124 (1980). The non-producing marmoset cell line, non-productively infected with simian sarcoma virus (SSV) and designated NPV/SiSV and NPVI/SISV were cultured as described in Devare et al., *Proc. Natl. Aced. Sci. USA*, 80 731–735 (1983). The avian fibroblast non-productivity transformed cell line infected with Fujinami sarcoma virus (FSV) was a gift from B. Sefton of the Salk Institute, La Jolla, Calif. Uninfected mouse NIH 3T3 fibroblast cells and mouse NIH 3T3 fibroblast cells productively infected with Harvey murine sarcoma virus were cultured as described in Todaro et al., *J. Cell Biol.*, 17, 299–313 (1963); and Harvey *Nature*, 204, 1104–1105 (1964). Human T24 bladder carcinoma cells were cultured as described in Bubenik et al., *Int. J. Cancer*, 11, 765–773 (1973).

B. Synthesis of Peptides

Polypeptides were synthesized using solid phase methods as described in Marglin and Merrifield, *A. Rev. Biochem.*, 39, 841–866 (1970), and were confirmed by amino acid analyses. Sequence information is derived from either amino acid sequencing of the viral protein or predictions based upon nucleotide sequencing. The sources of the sequence information were as listed in the footnotes relating to those sequences and their oncogenes.

For polypeptides having fewer than 35 residues that were used in immunizing inocula, a cysteine residue was added to the amino-terminus or to the carboxyl-terminus of each polypeptide whose corresponding oncoprotein sequence did not contain such a residue. The Cys residues were used to assist in coupling to a protein carrier as described below.

In preparing a useful synthetic polypeptide by the above solid phase method, the amino acid residues were linked to a cross-linked resin (solid phase) through an ester linkage from the carboxy-terminal residue. When the polypeptide was linked to a carrier via a Cys residue, that Cys residue was conveniently used as the carboxy-terminal residue that was ester-bonded to the resin.

The alpha-amino group of each added amino acid was typically protected by a tertiary-butoxycarbonyl (t-BOC) group prior to the amino acid being added into the growing polypeptide chain. The t-BOC group was then removed by standard techniques prior to addition of the next amino acid to the growing polypeptide chain.

Reactive amino acid side chains were also protected during synthesis of the polypeptides. Usual side-chain protecting groups were used for the remaining amino acid residues as follows: O-p-(bromobenzyloxycarbonyl) for tyrosine; 0-benzyl for threonine, serine, aspartic acid and glutamic acid; S-methoxybenzyl for cysteine, dinitrophenyl for histidine; 2-chlorobenzoxycarbonyl for lysine and tosyl for arginine.

Protected amino acids were recrystallized from appropriate solvents to give single spots by thin layer chromatography. Couplings were typically carried out using a ten-fold molar excess of both protected amino acid and dicyclohexyl carbodiimide over the number of milliequivalents of initial N-terminal amino acid. A two molar excess of both reagents may also be used. For asparagine, an equal molar amount of N-hydroxy-benzotriazole was added to the protected amino acid and dimethyl formamide was used as the solvent. All coupling reactions were more than 99% complete by the picric acid test of Gisin, *Anal. Chem. Acta.* 58:248–249 (1972).

After preparation of a desired polypeptide, a portion of the resulting, protected polypeptide (about 1 gram) was treated with two milliliters of anisole, and anhydrous hydrogen fluoride, about 20 milliliters, was condensed into the reaction vessel at dry ice temperature. The resulting mixture was stirred at about 4 degrees C. for about one hour to cleave the protecting groups and to remove the polypeptide from the resin. After evaporating the hydrogen fluoride at a temperature of 4 degrees C. with a steam of $N_2$, the residue was extracted with anhydrous diethyl ether three times to remove the anisole, and the residue was dried in vacuo.

The vacuum dried material was extracted with 5% aqueous acetic acid (3 times 50 milliliters) to separate the free polypeptide from the resin. The extract-containing solution was lyophilized to provide an unoxidized, synthetic polypeptide from the resin. The extract-containing solution was lyophilized to provide an unoxidized, synthetic polypeptide.

C. Coupling of Synthetic Polypeptides To Carrier Protein

The unoxidized synthetic polypeptides were coupled to the carrier protein keyhole limpet hemocyanin (KLH) through a cysteine residue (Cys; C) of the polypeptide with m-maleimidobenzoyl-N-hydroxysuccinimide ester as the coupling reagent as described in Green et al., *Cell*, 28, 477 and 487 (1982), Where a Cys residue was a terminal residue in a sequence, an additional cysteine residue was not added.

Briefly, as a generalized procedure for each polypeptide, 4 milligrams of KLH in 0.25 milliliters of 10 millimolar sodium phosphate buffer (pH 7.2) were reacted with 0.7 milligrams of MBS that was dissolved in dimethyl fermamide (DMF), and the resulting admixture was stirred for 30 minutes at room temperature. The MBS solution was added dropwise to ensure that the local concentration of DMF was not too high, as KLH is insoluble at DMF concentrations of about 30% or higher. The reaction product, KLH-MB, was passed through a chromatography column prepared with Sephadex G-25 (Pharmacia Fine Chemicals, Piscataway, N.J.) equilibrated with 50 millimolar sodium phosphate buffer (pH 6.0) to remove free MBS. KLH recovery from peak fractions of the column eluate, monitored at 280 nanometers, was estimated to be approximately 80%.

The KLH-MB so prepared was then reacted with 5 milligrams of polypeptide dissolved in 1 milliliter of buffer.

The pH value of the resulting reaction composition was adjusted to 7–7.5, and the reaction composition was stirred at room temperature for 3 hours.

D. Immunization And Fusion 1. fes-Related Polypeptides

Polypeptides such as those corresponding in amino acid residue sequence to a portion of the ST-FeSV v-fes oncoprotein were coupled to KLH, and were used to immunize 129 GIX$^+$ mice as described before and in Niman et al., in *Monoclonal Antibodies and T Cell Products*, Katz ed., (Boca Raton, Fla., CRC Press, Inc., 1982), pp. 21–51. Spleen cells from those immunized mice were fused with SP2/0-Ag14 myeloma cells using polyethylene glycol (PEG) 1500 (J. T. Baker Chemco, Phillsburg, N.J.); PEG solutions for fusion were prepared at least one month prior to use to promote fusion efficiency. SP2/0-Ag14 Cells do not produce their own Ig molecules, thereby facilitating isotype analysis and subsequent purification, such cells also do not produce retroviruses. The fused cells were then resuspended in 400 milliliters of Dulbecco's high-glucose minimal essential medium (Flow Laboratories, Inc. Inglewood, Calif.) containing 10 percent fetal calf serum, $1.0 \times 10^{-6}$ molar hypoxanthine, $1 \times 10^6$ molar methotrexate, and $1.6 \times 10^{-5}$ molar thymidine. Next, the cells were plated into 30 microliter plates and grown as described in Niman et al., *Proc. Natl. Acad. Sci. U.S.A.*, 1982 supra.

2. sis- and myb-Related Polypeptides

Polypeptides (c) and (d) whose amino acid residues correspond to positions 139–155 of the predicted sequence of simian virus transforming protein p28$^{ris}$ and to residues 2–18 of the predicted sequence of the avian myeloblastosis virus oncoprotein were synthesized and coupled to a KLH carrier as described above. The conjugates so prepared were administered at approximately 50 micrograms of polypeptide per 129 GIX$^+$ mouse per injection.

On day 0 (zero), each conjugate was mixed with complete Freund's adjuvant and injected intraperitoneally. On day 19, each conjugate was admixed with alum to provide a concentration of 5 milligrams per milliliter of alum, and injected intraperitoneally. A booster injection of polypeptide (c) in phosphate-buffered saline was administered intravenously on day 62. Serum containing oligoclonal antibodies was taken by orbital puncture on day 67. After a second alum-containing immunization of polypeptide (d) on day 41, the booster of polypeptide (d) was similarly administered on day 143 to similarly provide oligoclonal antibodies on day 148. The serum so obtained was tested for the antigenicity of its receptors as discussed in FIG. 4.

In a similar manner, polypeptides such as those corresponding to the below listed amino acid residue sequences were synthesized.

| abl | LRRACWQWNPSDRPSF |
| fms | FMQACWALEPTRRPTF |
| src | LMCQCWRKDPEERPTF |
|     | LGQGCFGEVWMG |
|     | GSSKSKPKDPSQRRRS |
| fgr | AMEQTWRLDPEERPTF |

Immunization was carried out in a manner similar to that described for the sis and myb amino acid residue sequences.

3. ras- and erb B-Related Polypeptides

Polypeptides such as those corresponding in amino acid residue sequence to residues 96–118 of the ras polypeptide from the predicted sequence of the ras oncogene of Kirsten murine sarcoma virus and residues 366–381 of the erb B polypeptide from the arian erythroblastemia virus were synthesized and coupled to a KLH carrier as described above. The conjugates so prepared were administered at approximately 50 micrograms of polypeptide per 129 GIX$^+$ mouse per injection.

On day 0 (zero), each conjugate was mixed with complete Freunds adjuvant and injected intravenously. On day 5, serum containing oligoclonal antibodies was taken by orbital puncture. The serum so obtained was tested for the antigenicity of its receptors as discussed in FIG. 4.

E. Antibody Binding Assay

Hybridomas producing anti-polypeptide antibodies were detected with an enzyme-linked immunoabsorbent assay (ELISA) method as discussed in the description of FIG. 4, herein, and in Niman et al., *Monoclonal Antibodies and T Cell Products*, supra. Briefly, approximately 50 micromoles of polypeptide were dried onto microliter plates, fixed with methanol, and incubated with hybridoma tissue culture supernatant. After thorough washing, hybridoma antibody binding was detected using rabbit anti-mouse kappa chain antibody (Litton Bionetics Inc., Kensington, Md.) followed by a glucose oxidase conjugated goat anti-rabbit antisera. Binding was visualized with 2.2'-azino-di[3-ethyl-benzothiazoline-sulfonate (6)] (ABTS) dye (Boehringer-Mannheim, Indianapolis, Ind.) in the presence of glucose and horseradish peroxidase as described in Niman et al., *Monoclonal Antibodies and T Cell Products*, supra. Isotype was determined by substituting various rabbit anti-mouse lambda or heavy chain sera for the anti-mouse kappa chain as described above.

F. Electrophoretic Transfer and Immunological Detection of Proteins on Nitrocellulose Cell extracts were subjected to polyacrylamide gel electrophoresis, and the protein was transferred to nitrocellulose (Schleicher and Schuell, Inc., Keene, N.H.) as discussed in the description of FIG. 5, herein, and in Niman et al., *Virology*, 123, 187–205 (1982). Peroxidase-labeled rabbit anti-mouse IgG serum (Tago, Inc., Burlingame, Calif.) diluted 1/1000 was incubated with the transfers for one hour at 25 degrees C. followed by washing as described in Niman and Elder, in *Monoclonal Antibodies and T Cell Produces*, above. The bound antibody was visualized by incubation in 10 millimolar Tris (2-amino-2-(hydroxymethyl)-1,3-propanediol), pH 7.4, 0.009 percent $H_2O_2$ 0.0025 percent 3,3'-dimethoxybenzidine dihydrochloride (Eastman-Kodak, Co., Rochester, N.Y.).

G. Preparation of Purified PDGF

Sixteen units of outdated platelets were obtained from the San Diego Blood Bank, San Diego, Calif. The purified PDGF used herein was obtained following the first two steps of the procedures described in Antonaides et al., *Proc. Natl. Acad. Sci. USA*, 76, 1809–1813 (1979).

Briefly, platelets were collected by centrifugation at 28,000× gravity (g) for 20 minutes at 4 degrees C. The obtained platelets were washed by resuspension in 400 milliliters of a mixture containing (a) 9 volumes of 17 millimolar Tris-HCl, at pH 7.4 including 0.15 molar NaCl and 1% glucose; and (b) 1 volume of a solution that includes per 100 milliliters: 0.8 grams citric acid monohydrate, 2.2 grams anhydrous dextrose and 2.6 grams of sodium citrate dihydrate, followed by further centrifugation at 28,000×g for 10 minutes at 4 degrees C. The thus washed platelets were then resuspended in 16 milliliters of an aqueous solution containing 0.008 molar NaCl and 0.01 molar phosphate ion at pH 7.4 (NaCl-phosphate ion solution), and boiled for 10 minutes to lyse the cells.

Phenylmethyl sulfonyl fluoride and Traysylol (Sigma Chemical Co., St. Louis, Mo.), protease inhibitors, were added to the lysed cells at concentrations of 1 millimolar and 3%, respectively. The lysed cell mixture was again centrifuged to provide a pellet and a supernatant.

The supernatant was mixed with 8 milliliters of CM Sephadex C-50 (Pharmacia Fine Chemicals, Piscataway, N.J.) beads that were previously equilibrated in the NaCl-phosphate ion solution. The beads and liquid were poured into a chromatography column (15×1.5 centimeters) that was washed with 6 column volumes of the above NaCl-phosphate ion solution. The PDGF, first eluate, was obtained by eluting the column with two column volumes of 1 molar NaCl. Traysylol was added to the eluate to provide a final concentration of 3%, and the eluate was dialyzed against the above NaCl-phosphate ion solution.

The above-produced lysed cell pellet was extracted with a 1 molar NaCl solution for 24 hours at 4 degrees C., and centrifuged. The supernatant was dialyzed against the above NaCl-phosphate ion solution, admixed with the above Sephadex, and made into a column. The column was washed and eluted as above to provide a second eluate that was dialyzed as above. The pellet prepared in this procedure was treated the same way to provide a third eluate that was again dialyzed as discussed before.

The three dialyzed eluates were pooled and concentrated to a few milliliters of volume using an Amicon ultrafiltration apparatus (Amicon, Lexington, Mass.) and a filter having a 10K dalton exclusion. The PDGF so purified was then treated as discussed for FIG. 5.

Purified PDGF extract from approximately 2.5 units of platelets were mixed with a minimal volume of solution containing 0.5 percent sodium dodecyl sulfate (SDS) and 5 percent of 2-mercaptoethanol. The resulting mixture was boiled for two minutes and then electrophoresed therethrough a 5–17 percent polyacrylamide gel. The protein was thereafter electrophoretically transferred to nitrocellulose. (Niman and Elder, supra.) that was thereafter cut into strips, following the Western blot procedure.

The nitrocellulose strips so prepared were then treated with a solution containing 3 percent bovine serum albumin (BSA), 0.1 percent polyoxyethylene-9-octyl phenyl ether (Triton® X-100) in phosphate buffered saline to inhibit non-specific protein binding. Four milliliters of mouse antiserum diluted 1:200 were then incubated with the nitrocellulose strips.

After washing three times with a solution of 0.1 percent Triton® X-100 in PBS, the nitrocellulose strips were incubated either with $10^6$ counts per minute of $_{125}$I-labeled *Staphylococcus aureus* protein, or a 1:1000 dilution of peroxidase-conjugated goat anti-mouse serum (Tago), and again washed with 0.1 percent Triton® X-100 in PBS. The peroxidase conjugate was developed with a solution containing 0.0009 percent $H_2O_2$, 0.0025 percent 3,3'-dimethoxybenzidine dihydrochloride (Eastman-Kodak, Co.,) in a 10 millimolar Tris buffer having a pH value of 7.4. The $^{125}$I labeled strips were developed by exposure on XRP-1 film (Eastman-Kodak Co.) using Cronex Hi-Plus (E.I. DuPont de Nemours & Co.) intensifying screens at minus 70° C. for 48 hours.

H. Urine Assay

Urine from donors (patients) as noted in the description of the Figures was collected and used as collected or concentrated to 40-fold using an Amicon ultrafiltration apparatus. This fluid was employed as the body fluid sample aliquot in the assay for proteins encoded by or related to sis, fes and ras oncogenes.

The concentrated urine sample was prepared in the following manner. The urine was clarified at 6000 r.p.m. at 4° C. for 10 minutes. The supernatant was then concentrated using an Amicon filter having a 10,000 dalton exclusion. This concentrated urine was then dialyzed to separate protein fractions.

Concentrated urine was electrophoresed at 25 microliters per lane into a 5–17% polyacrylamide gel to provide the equivalent of protein from one ml of collected urine, and then electrophoresed onto nitrocellulose. The nitrocellulose filter was then probed with a 1/200 dilution of, for example, mouse antiserum in a solution 3% bovine serum albumin, 0.1% Triton® X-100 and PBS. The nitrocellulose filter was then washed three times and incubated with $10^6$ cpm of $^{125}$I-labeled protein A.

Binding was visualized with intensifying screens at −70° Centigrade as described in FIG. 6, supra.

I. Oncoproteins and Transformed Cells

NRK and SSV-transformed NRK cells were provided by S. A. Aaronson and K. C. Robbins of the Center for Cancer Research, National Institutes of Health, Bethesda, Md. The cells were grown in Dulbecco's minimal essential medium supplemented with 10% fetal calf serum, 2 millimolar L-glutamine, 100 IU per milliliter of penicillin and 100 micrograms per milliliter of streptomycin.

Parallel cultures of NRK and SSV-transformed NRK cells were washed 3 times for 2 hours intervals, and were then incubated for 18 hours in medium without serum at 15 milliliters per T75 centimeter$^2$ flask. The medium so conditioned was then centrifuged, and was stored frozen at −70° C.

The conditioned medium was thawed, concentrated 500-fold using dialysis in i molar acetic acid and was thereafter lyophilized. After solubilization and reduction with 10% 2-mercaptoethanol, 50 microliters of concentrated, conditioned media were electrophoresed into a 5–17% sodium dodecyl sulfate polyacrylamide gel. Secreted proteins were then electrophoretically transferred and bound to nitrocellulose. Nonspecific binding was blocked by preincubation of the cell extract with a solution containing 3% of bovine serum albumin and 0.1% polyoxyethylene octyl phenyl ether in phosphate buffered saline at a pH value of 7.4.

Prior to carrying out the immunological assays, 20 microliters of mouse antisera induced by PDGF-2(1–18) or PDGF-2(73–89) (described before) were preincubated with 100 micrograms of an appropriate polypeptide for 1 hours at 37° C. The oligoclonal antibody-containing/polypeptide reaction mixture was then diluted 1:500 with the above preincubation solution. The diluted solution so prepared was then contacted at 4° C. with the nitrocellulose-bound conditioned media, and that contact was maintained (incubated) for a time period of 15 minutes, a time sufficient for the immunoreaction of the antibody (receptor) and protein bound on the nitrocellulose. The nitrocellulose was thereafter washed.

The washed nitrocellulose was then contacted with affinity-purified rabbit anti-mouse $IgG_1$ antibodies (Litton) diluted 1:500 at 25° C. The contact was maintained for a time period of 2 hours sufficient for the anti-mouse $IgG_1$ antibodies to immunoreact with antibodies from the antisera that had bound to the nitrocellulose-bound secreted proteins of the conditioned media. The nitrocellulose was then washed again.

Immunoreaction (binding) was visualized with $10_6$ counts per minute of 125I-labeled *Staphylococcus aureus* protein A as described in Niman, *Nature*, 307, 180–183 (1984).

J. Oncoproteins in the Urine Samples of Newborns and Pregnant Mothers

The monoclonal receptors utilized were prepared as described previously. One ml of urine from each of the newborns was admixed with sufficient 2-mercaptoethanol to make a 10 volume percent solution. The resulting solution was boiled for 2 minutes. Upon cooling, aliquots of the resulting reduced solution were electrophoresed on 5–17 percent polyacrylamide gels. The proteins of the resulting gels were transferred to nitrocellulose following standard procedures. Nitrocellulose blots for each urine sample were individually screened for immunoreactivity with each of the antibody probes following standard procedures for such Western blots. Autoradiography was for 4 hours at −70° C. using Cronex intensifying screens. The relative intensities of immunoreaction were thereafter determined.

Urine samples from pregnant (expectant) mothers were concentrated prior to electrophoresis. Here, proteins from serial urine collections taken in a time period 16–20 weeks into the pregnancy (based upon the last menstrual cycle) were first precipitated from the urine samples by admixture with 2 volumes (based on the urine volume) of acetone and maintenance at 4° C. The precipitated proteins were collected and resuspended using 1/20 of the original sample volume of PBS. The sex of the fetuses being carried was determined either by amniocentesis or visual inspection after birth.

The United States Government has rights in this invention pursuant to Public Health Service Contract NO1-CP-41009, Public Health Service Grants CA 38160 and CA25803.

The foregoing is intended as illustrative of the present invention but not limiting. Numerous variations and modifications may be effected without departing from the true spirit and scope of the novel concepts of the invention.

We claim:

1. A method of assaying a body sample from a host for an indicant of exposure to a carcinogen prior to clinical symptoms of cancer, comprising the steps of:

(a) contacting said body sample with a receptor molecule, wherein said receptor binds to both (i) an onco-protein to form an onco-protein/receptor complex and ii) a peptide having an amino acid residue sequence containing about 7 to about 40 amino acids corresponding to a portion of said onco-protein, and, (b) determining the level of said onco-protein in said body sample by detecting the amount, if any, of said onco-protein/receptor complex;

wherein an elevated level of said onco-protein, relative to said level in a normal sample, is indicative of exposure of said host to at least one carcinogen.

2. A method of claim 1 wherein said body sample is selected from the group consisting of blood, tissue, and urine.

3. A method of claim 1 wherein said assay is an immunoblot.

4. A method of claim 1 wherein said receptor molecule is selected from the group consisting of a polyclonal antibody, an oligoclonal antibody, a monoclonal antibody and a fragment thereof.

5. A method of claim 1 wherein said receptor molecule binds to both (a) H-ras oncogene-related p21 and (b) a polypeptide having an amino acid residue sequence, from left to right and in the direction, from amino terminus to carboxy terminus represented by a formula selected from the group consisting of:

Y R E Q I K R V K D S D D V P M V L V G N K C, and
   Y T L V R E I R Q H K L R K L N P P D E S G P G C.

6. A method of assaying a body sample from a host for an indicant of exposure to a carcinogen prior to clinical symptoms of cancer, comprising the steps of:

(a) contacting said body sample with a receptor molecule, wherein said receptor binds to both (i) H-ras oncogene-related p21 protein to form a p21 protein/receptor complex, and (ii) a peptide having an amino acid residue sequence, from left to right and in the direction from amino terminus to carboxy terminus, represented by a formula selected from the group consisting of:

Y R E Q I K R V K D S D D V P M V L V G N K C, and
   Y T L V R E I R Q H K L R K L N P P D E S G P G C, and, (b) determining the level of said p21 protein by detecting the amount, if any, of said p21 protein/receptor complex;

wherein an elevated level of said p21 protein, relative to said level in a normal sample, is indicative of exposure of said host to at least one carcinogen.

* * * * *

UNITED STATES PATENT AND TRADEMARK OFFICE
CERTIFICATE OF CORRECTION

PATENT NO.   : 5,733,738
DATED        : March 31, 1998
INVENTOR(S)  : Niman et al.

Page 1 of 1

It is certified that error appears in the above-identified patent and that said Letters Patent is hereby corrected as shown below:

<u>Column 1,</u>
Line 4, insert:
-- This invention was made with government support under Contract Nos. NO1-CP-41009, CA 38160 and CA 25803 by the National Institutes of Health. The government has certain rights in the invention. --

Signed and Sealed this

Nineteenth Day of March, 2002

Attest:

JAMES E. ROGAN
*Director of the United States Patent and Trademark Office*

*Attesting Officer*